US012272099B2

(12) United States Patent
DiMarco et al.

(10) Patent No.: US 12,272,099 B2
(45) Date of Patent: Apr. 8, 2025

(54) SYSTEM AND METHOD FOR EVALUATING PATIENT DATA

(71) Applicant: Phyxd Inc., New York, NY (US)

(72) Inventors: Anthony DiMarco, New York, NY (US); Jeffrey Burde, New York, NY (US); Robin Galaskewicz, New York, NY (US); Shih Wei Wong, New York, NY (US); Jedrek Fulara, New York, NY (US); Christopher Merritt-Lish, New York, NY (US)

(73) Assignee: Phyxd Inc., New York, NY (US)

( * ) Notice: Subject to any disclaimer, the term of this patent is extended or adjusted under 35 U.S.C. 154(b) by 50 days.

(21) Appl. No.: 17/975,343

(22) Filed: Oct. 27, 2022

(65) Prior Publication Data

US 2023/0139841 A1 May 4, 2023

Related U.S. Application Data

(60) Provisional application No. 63/402,689, filed on Aug. 31, 2022, provisional application No. 63/273,039, filed on Oct. 28, 2021.

(51) Int. Cl.
*G06T 19/00* (2011.01)
*A61B 5/00* (2006.01)
(Continued)

(52) U.S. Cl.
CPC .............. *G06T 7/75* (2017.01); *A61B 5/1077* (2013.01); *A61B 5/1079* (2013.01);
(Continued)

(58) Field of Classification Search
CPC ... A61B 5/1116; A61B 5/4561; A61B 5/7275; G06T 7/0014; G06T 19/00; G06T 2200/24; G06T 2207/30012; G06T 2210/41
See application file for complete search history.

(56) References Cited

U.S. PATENT DOCUMENTS 9,161,019 B2 10/2015 Millett
10,244,228 B2 3/2019 Millett
(Continued)

FOREIGN PATENT DOCUMENTS

EP 4272650 A1 * 11/2023 ........... A61B 5/1113
KR 10-2019-0057566 A 5/2019
(Continued)

OTHER PUBLICATIONS

International Search Report and Written Opinion on PCT Appl. Ser. No. PCT/US2022/048076 dated Feb. 28, 2023 (9 pages).

*Primary Examiner* — Chante E Harrison
(74) *Attorney, Agent, or Firm* — Foley & Lardner LLP

(57) ABSTRACT

A method of extracting and displaying postural measurements from patient data includes retrieving, by a processor of a computing device, the patient data from memory. The patient data includes a geometric mesh representation of a patient, including a plurality of data points corresponding to spatial coordinates of a plurality of vertices in three dimensions. The method also includes determining, by the processor, a reference geometry along the geometric mesh representation in a fixed position with respect to the spatial coordinates; determining, by the processor, a landmark corresponding to one of skeletal or soft tissue anatomy for the patient; and determining, by the processor, a postural deviation of a body portion of the patient by comparing the reference geometry and the landmark. The method further includes displaying, by a display of the computing device, a graphical user interface indicating a characteristic related to the postural deviation.

19 Claims, 39 Drawing Sheets

(51) Int. Cl.
    *A61B 5/107*     (2006.01)
    *A63B 24/00*     (2006.01)
    *G06T 7/00*     (2017.01)
    *G06T 7/62*     (2017.01)
    *G06T 7/73*     (2017.01)

(52) U.S. Cl.
    CPC .......... *A61B 5/4561* (2013.01); *A61B 5/7267* (2013.01); *A61B 5/7275* (2013.01); *A63B 24/0075* (2013.01); *G06T 7/0014* (2013.01); *G06T 7/62* (2017.01); *G06T 19/00* (2013.01); *G06T 2200/24* (2013.01); *G06T 2207/30012* (2013.01); *G06T 2210/41* (2013.01)

(56) References Cited

U.S. PATENT DOCUMENTS

| | | | |
|---|---|---|---|
| 10,327,697 B1 * | 6/2019 | Stein | A61B 5/1116 |
| 10,682,093 B1 | 6/2020 | Stein et al. | |
| 11,763,235 B1 * | 9/2023 | Penfield | G06F 40/30 |
| | | | 704/9 |
| 11,922,358 B1 * | 3/2024 | Penfield | G06Q 10/0635 |
| 2010/0022351 A1 | 1/2010 | Lanfermann et al. | |
| 2013/0178960 A1 | 7/2013 | Millet | |
| 2014/0071234 A1 | 3/2014 | Millett | |
| 2016/0110595 A1 | 4/2016 | Wang et al. | |
| 2016/0148132 A1 * | 5/2016 | Aqlan | G06Q 10/0635 |
| | | | 705/7.16 |
| 2016/0234476 A1 | 8/2016 | Millett | |
| 2016/0247017 A1 * | 8/2016 | Sareen | A61B 5/7475 |
| 2019/0222826 A1 | 7/2019 | Millett | |
| 2023/0267637 A1 * | 8/2023 | Tan | G06V 10/764 |
| | | | 382/103 |

FOREIGN PATENT DOCUMENTS

| | | |
|---|---|---|
| KR | 20230003555 A * | 1/2023 |
| WO | WO-2014/040081 A1 | 3/2014 |

* cited by examiner

| Field Label | Field Type | Format |
|---|---|---|
| Last Name | open text | open text field |
| First Name | open text | open text field |
| Email | open text | open text field |
| Phone Number | open numerical | xxx-xxx-xxxx |
| Date of Birth | date select, scroll | MM-DD-YYYY |
| Gender | dropdown | text |
| Height (ft in") | xx'xx" | xx'xx" |
| Weight (lbs) | open numerical | xxx |
| Relevant Medical/Injury History | open text | open text field |
| Provider | dropdown - PhyCoach Name | |
| Source | dropdown | |
| Level of Activity | | |
| Activity Type | Dropdown of discrete options (s | text |
| Level | dropdown | text |
| Comments | open text | open text field |
| Date | date select, scroll | MM-DD-YYYY |
| Level of Discomfort | | |
| Zone | dropdown | text |
| Condition | dropdown | text |
| Value | dropdown | numerical, text |
| Duration of Main Discomfort | dropdown | text |
| Note | open text | open text field |
| Date | date select, scroll | MM-DD-YYYY |

View user

| User | Level of Activity | Level of Discomfort | Scan | PDF | 3D Model | Notes | History | Movement Plan | Bookings | Payment |

ID: d8aca65bb-b128-4f23-a950-e168b8ca9c18
Name: Name 1
Email: Name1@user.com
Phone Number: 999-999-9999
Weight: 220
Height: 06'0"
Relevant Medical & Injury History: Heart injured by shrapnel
Gender: Male
Date of Birth: 05-29-1970
Status: Active
Scan option: Default scan
Provider: Provider 1
Clinic: Clinic 1
Credits: 0
Source: OTC

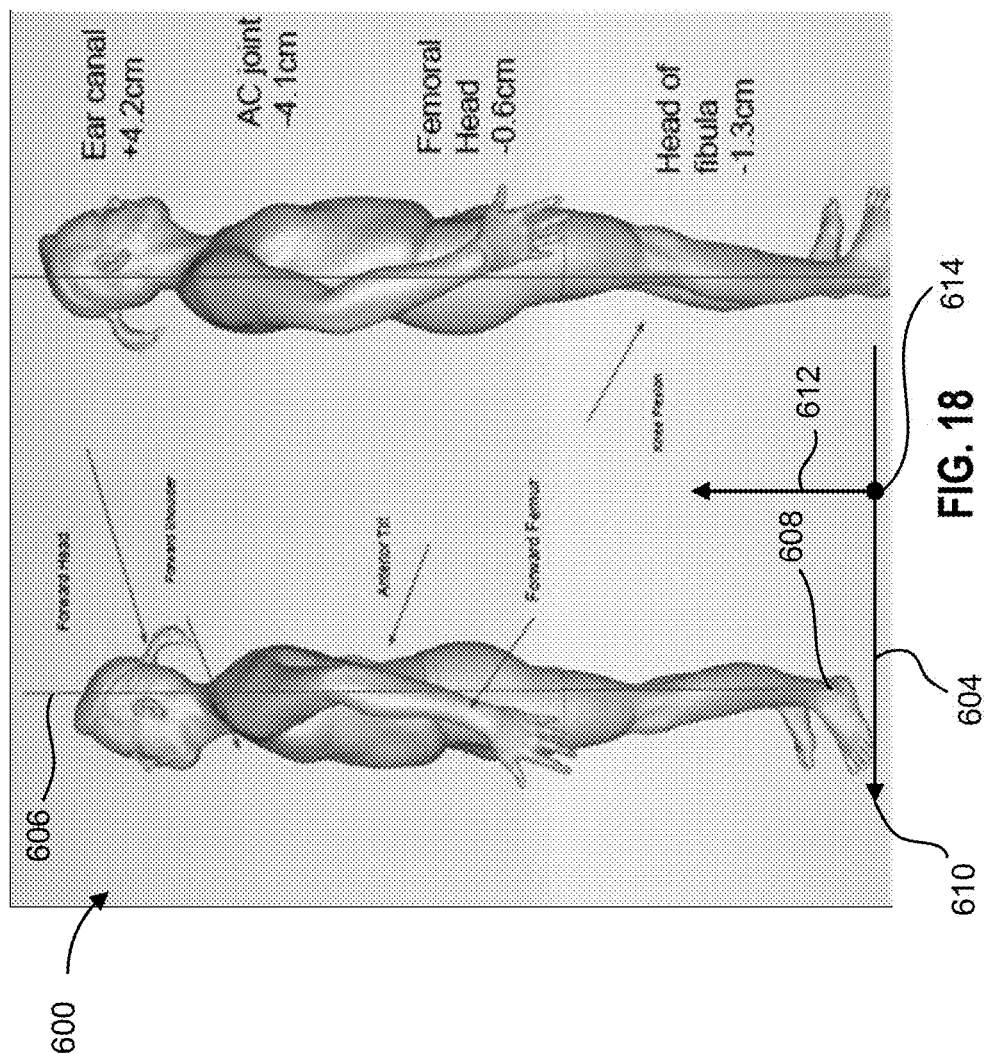

Shoulders

| Analysis | Result | Unit | Risk |
|---|---|---|---|
| Height difference | 14 | mm | NEEDS ATTENTION |

*The left shoulder is 14mm above the right shoulder.*

| LANDMARK ANGLES | LEFT SIDE | RIGHT SIDE | DIFFERENTIAL |
|---|---|---|---|
| ASIS-PSIS-GREATER TROCHANTER | 18° | | 4° (R) |
| ASIS-PSIS | 3° | 1° | 2° (L) |
| DATA SUMMARY | Left pelvis is more forward and tilted. | Right femur is in a less optimal position. | |

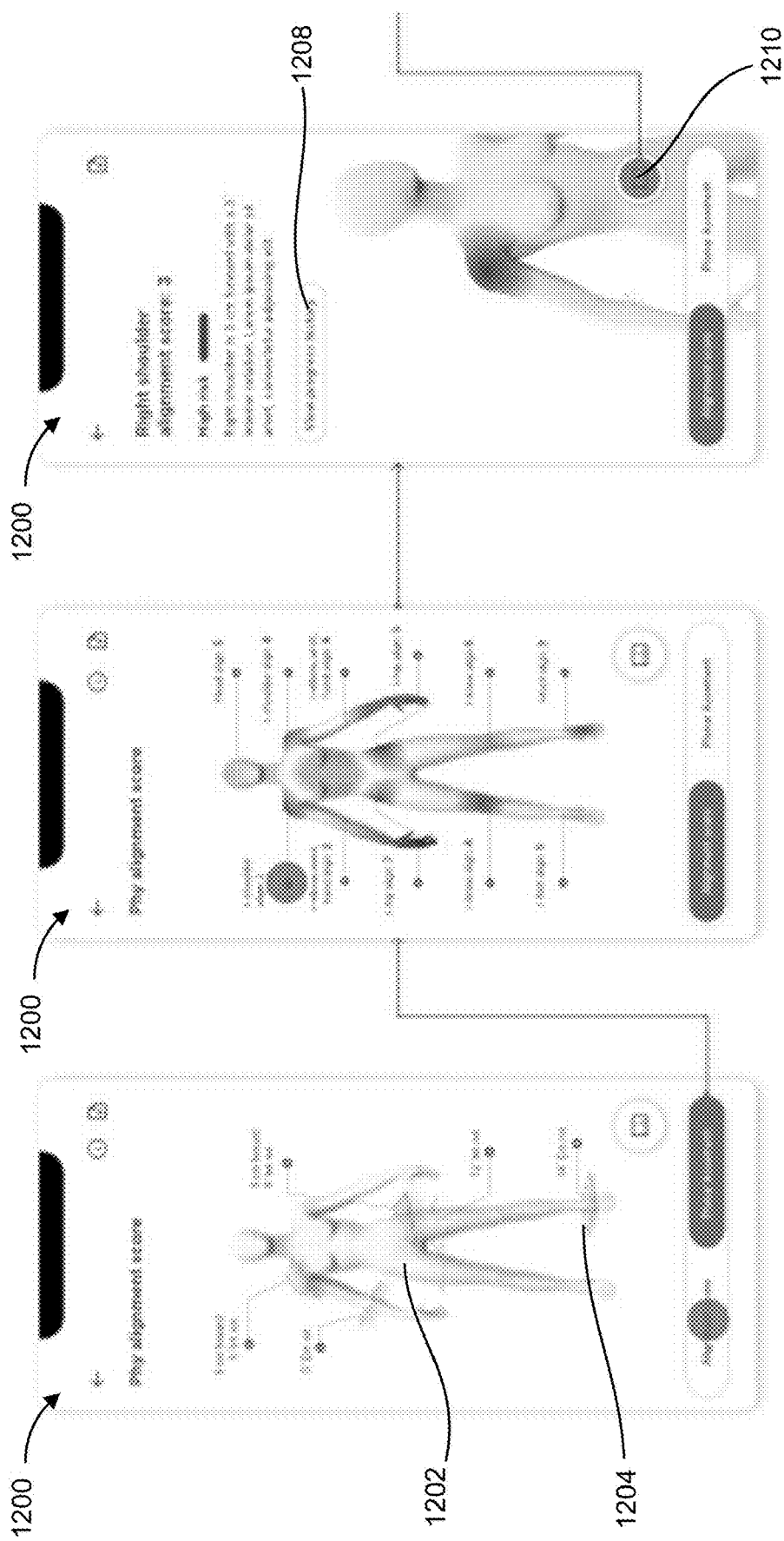

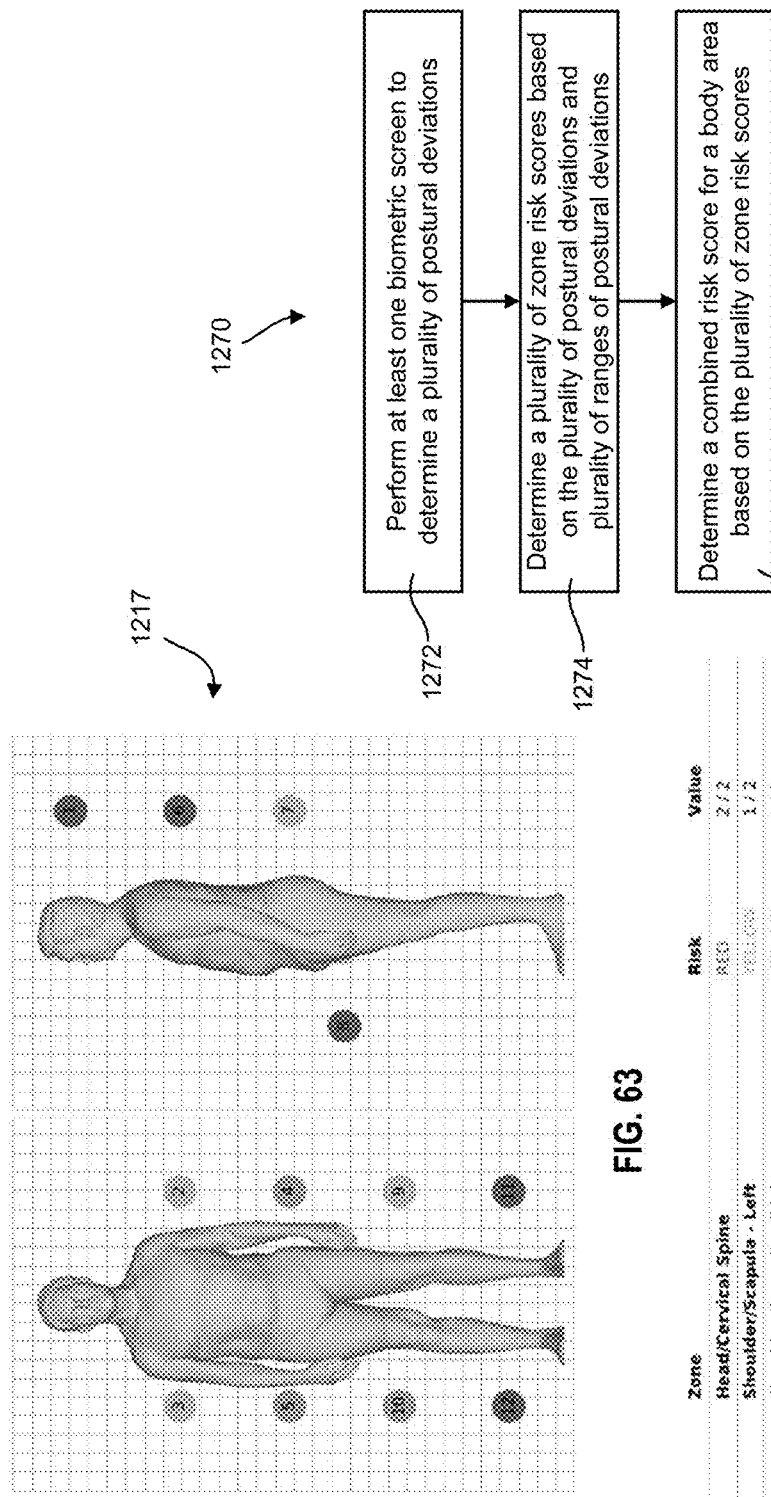

SYSTEM AND METHOD FOR EVALUATING PATIENT DATA

CROSS-REFERENCE TO RELATED PATENT APPLICATIONS

The present application claims the benefit of and priority to U.S. Provisional Patent Application No. 63/273,039, filed Oct. 28, 2021 and U.S. Provisional Patent Application No. 63/402,689, filed Aug. 31, 2022, the contents of which are hereby incorporated by reference in their entirety.

BACKGROUND

The present disclosure relates generally to clinical screenings and evaluating patient data such as skeletal and soft tissue anatomy data of a human body. More specifically, the present disclosure relates to systems and methods for evaluating postural deviation in a human body, prescribing exercises and routines to reduce pain and improve patient posture, and predicting vulnerability to injury based on changes in patient data over time.

SUMMARY

At least one embodiment of the present disclosure relates to a method of extracting and displaying postural measurements from patient data. The method includes retrieving, by a processor of a computing device, the patient data from memory. The patient data includes a geometric mesh representation of a patient, including a plurality of data points corresponding to spatial coordinates of a plurality of vertices in three dimensions. The method also includes determining, by the processor, a reference geometry along the geometric mesh representation in a fixed position with respect to the spatial coordinates; determining, by the processor, a landmark corresponding to one of skeletal or soft tissue anatomy for the patient; and determining, by the processor, a postural deviation of a body portion of the patient by comparing the reference geometry and the landmark. The method further includes displaying, by a display of the computing device, a graphical user interface indicating a characteristic related to the postural deviation.

Another embodiment of the present disclosure relates to a system for evaluating patient data. The system includes memory storing the patient data, a display, and a processing circuit. The patient data includes a geometric mesh representation of a patient. The geometric mesh representation may include a plurality of data points corresponding to spatial coordinates of a plurality of vertices in three dimensions. The processing circuit is communicably coupled to the memory and the display. The processing circuit is configured to: (i) determine a reference geometry along the geometric mesh representation at a fixed position with respect to the spatial coordinates; (ii) determine a landmark corresponding to one of skeletal or soft tissue anatomy for the patient; (iii) determine a postural deviation of a body portion of the patient by comparing the reference geometry to the landmark; and (iv) presenting, on the display, a characteristic related to the postural deviation.

Yet another embodiment of the present disclosure relates to a non-transitory computer-readable medium having instructions stored thereon that, upon execution by a computing device, cause the computing device to perform operations comprising: (i) retrieving patient data comprising a geometric mesh representation of a patient, the geometric mesh representation including a plurality of data points corresponding to spatial coordinates of a plurality of vertices in three dimensions; (ii) determining a reference geometry along the geometric mesh representation at a fixed position with respect to the spatial coordinates; (iii) determining a landmark corresponding to one of skeletal or soft tissue anatomy for the patient; and (iv) transmitting, to a display of the computing device, a characteristic related to the postural deviation.

This summary is illustrative only and should not be regarded as limiting.

BRIEF DESCRIPTION OF THE FIGURES

The disclosure will become more fully understood from the following detailed description, taken in conjunction with the accompanying figures, wherein like reference numerals refer to like elements, in which:

FIG. 3 is a survey form for a clinical screening and assessment system, according to an embodiment.

FIGS. 7-10 are display screens of an administrative GUI showing profile data associated with data review and analysis, according to various embodiments.

FIG. 11 is a display screen of an administrative GUI showing profile data associated with a user of the clinical screening and assessment system, according to an embodiment.

FIG. 12 is a display screen of an administrative GUI for specifying level of activity data for a user, according to an embodiment.

FIG. 13 is a display screen of an administrative GUI for specifying level of discomfort data for a user, according to an embodiment.

FIG. 18 is a side view of a 3D mesh of a human body, according to an embodiment.

FIGS. 56-62 are display screens of a GUI that summarizes the results of a clinical assessment, according to at least one embodiment.

FIG. 63 is a display screen of another GUI that summarizes the results of a clinical assessment, according to at least one embodiment.

FIG. 64 is a display screen of a risk score summary table, according to at least one embodiment.

FIG. 65 is a flow diagram of a method of determining a combined risk score for a body area of a patient, according to at least one embodiment.

DETAILED DESCRIPTION

Figure 1:
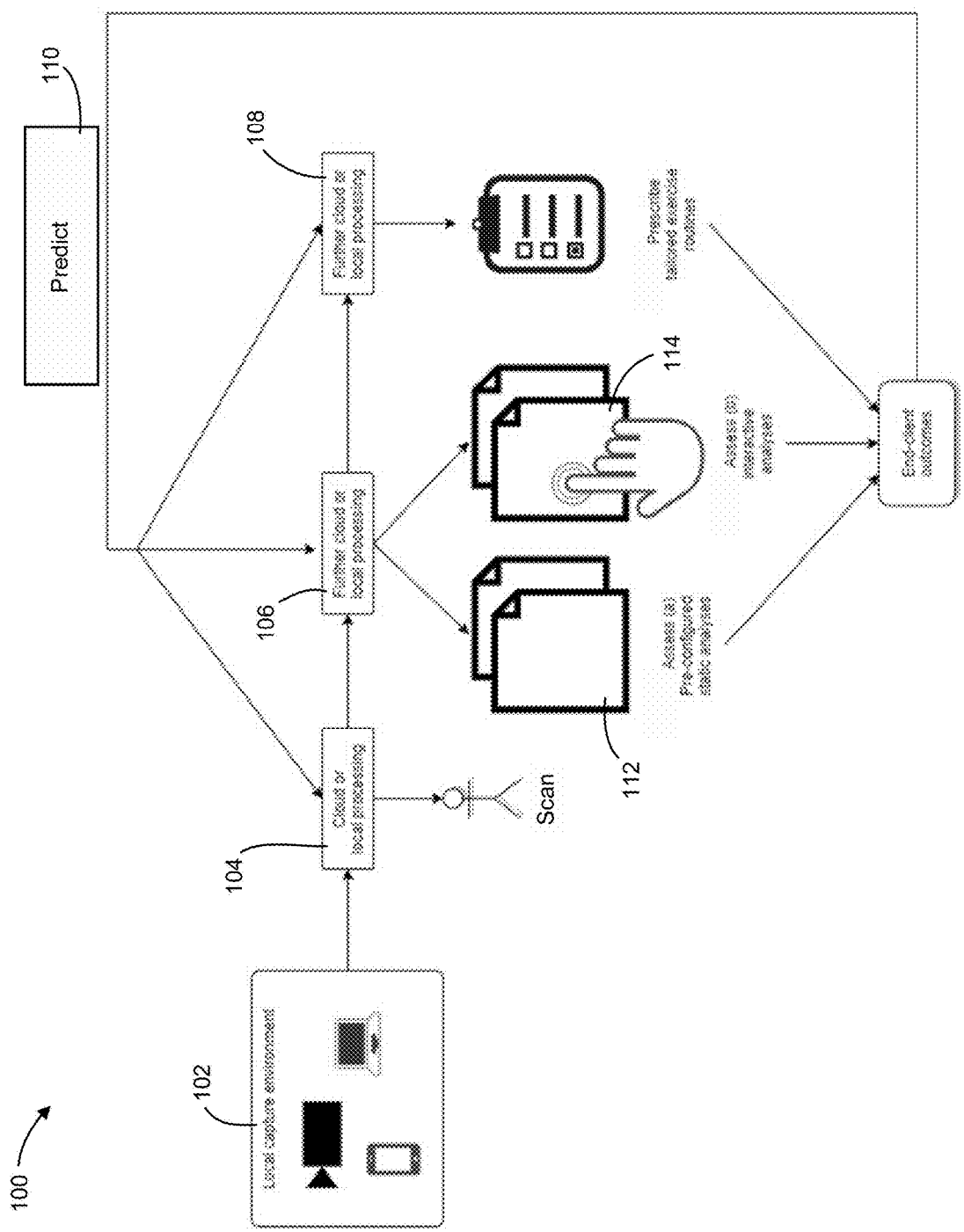
FIG. 1 is a block diagram of a clinical screening and assessment system, according to an embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Many individuals experience body pain (e.g., joint pain, muscle aches, etc.), limited range of motion, and other physiological issues at some point in their lifetimes. This pain may be caused by various underlying conditions including, for example: hereditary issues such as skeletal misalignment; physical injury; low muscle strength; tissue damage; and poor posture, among other factors. Left unchecked, the pain and suffering resulting from these underlying conditions can worsen, leading to additional injuries and reducing the individual's overall quality of life. These underlying conditions can also limit a person's athletic performance and prevent them from reaching their full potential.

In many instances, these underlying physiological conditions can be improved through rehabilitative therapies (e.g., occupational therapy, physical therapy, sports therapy, etc.), for example, by exercising specific muscle groups to improve posture, balance, and form. To diagnose the underlying conditions, a physical therapist may perform an in-person examination and may use tools, such as a goniometer to measure the range of motion of different parts of the body. However, the measurements obtained through goniometry and other measurement techniques may be inconsistent between users, and may be prone to human error. For example, in goniometry, the starting position of the goniometer, the center of rotation, the long axis of the limb and the true vertical and horizontal positions can only be visually estimated, which leads to uncertainty in and inconsistency between measurements. Methods of treating these physiological conditions may also vary between practitioners, based on their experience level and the interplay between various underlying conditions, which some practitioners may be unaware of. Furthermore, the efficacy of existing treatment methods may be difficult to quantify.

Referring generally to the figures, systems and methods for clinical screening and assessment are shown, according to various embodiments. In some embodiments, the system includes software (e.g., an application, etc.) that can be installed on a computing device (e.g., a user device, mobile device, and/or another computing device). The software is configured to use existing hardware on the computing device to capture patient data. In some embodiments, the patient data includes a geometric mesh representation of a body of the patient generated from images and/or scans of the patient (e.g., images taken from a mobile phone and/or other computing device). The mesh may include spatial data in three dimensions, and may include data points corresponding to specific body geometry (e.g., data points extending along vertebrae and/or between vertebrae along the spine, etc.). The system may be configured to analyze the data from the user's device and/or remotely using a cloud computing device. The system may include a graphical user interface (GUI) configured to allow a user to manipulate the data points, specify landmarks in different body areas using skeletal or soft tissue anatomy, and/or otherwise manipulate the mesh through the interactive GUI. Beneficially, the system generates and analyzes a volumetric mesh of the patient, using analysis techniques that are reliable and reproducible.

As used herein, a "mesh" refers to a collection of vertices, edges and faces that define the shape of a patient or a user. "Volumetric mesh" refers to a collection of vertices, edges, and faces that together provide a three dimensional representation of the patient. For example, the volumetric mesh of the patient may include exterior vertices along both the outer surface of a patient's skin as well as interior vertices contained within the outer surface to approximate the location of skeletal or soft tissue geometry throughout the patient's body. Faces of the mesh may be surfaces formed by at least three vertices (e.g., exterior vertices, interior vertices, or a combination thereof).

In at least one embodiment, the system is configured to evaluate the posture and movement of the scanned patient in (1) a pre-configured mode in which the mesh and pre-defined landmarks are analyzed to identify deviations from nominal alignment of the body structure (e.g., acceptable, neutral, healthy, etc.) and/or range of motion, and (2) an interactive data analysis mode in which manually analysis of the mesh can be performed to determine targeted metrics defined by the patient and/or practitioner. The system may be configured to determine a health and/or performance rating for various body areas based on analysis of the mesh, and an omnibus (e.g., overall) rating that is indicative of the combined deviations measured for different body areas (e.g., a posture assessment rating indicative of an overall level of postural deviation, a range of motions assessment rating indicative of an overall range of motion of the body, or of different regions of the body, etc.). In at least one embodiment, the system includes a GUI that is structured to facilitate identification of problem areas, and to allow users to determine additional information based on their own analysis of the mesh and measurement information.

In at least one embodiment, the system is configured to determine a sequence of exercises and/or therapeutic regimens based on measured deviations in the patient's posture, range of motion, and/or other measured physiological conditions. The sequence of exercises may be customized to each individual, based on their unique combination of deviations, patterns of deviations, vulnerabilities, and needs. In some embodiments, the system may be configured to provide targeted relief to the patient based on a priority order of exercises and/or routines. For example, to system may be configured to prioritize structural deviations causing pain or discomfort prior to engagement with a more holistic routine to improve overall structural misalignment and performance potential.

In at least one embodiment, the system is configured to track a patient's progress over time, using exercise tracking (e.g., to determine how well the patient has adhered to their prescribed exercise regimen, etc.), by performing multiple scans of the patient's body during treatment, by surveying the patient, or through a combination of these techniques. The system may also be configured to make predictions of how postural deviations and/or other physiological conditions will change over time, based on historical trends, and/or through analysis of data from multiple patients. The system may also be configured to predict susceptibility to injury, and to tailor the exercise regime to reduce the risk of injury. The aggregate data and historical trends may also be used to improve the efficacy of exercise prescriptions, for example, by introducing variability into the exercise regimens and iteratively tracking progress across multiple patients (e.g., using machine learning techniques, design of experiments, etc.).

In at least one embodiment, a method of evaluating patient data includes determining a postural deviation of a body portion based on patient data that includes a geometric mesh representation of a body surface. The geometric mesh representation includes data points in three spatial dimensions. The method further includes generating a graphical user interface indicating an amount of the postural deviation.

Another embodiment of the present disclosure relates to a method of evaluating patient data. The method includes determining a postural deviation of a body portion based on patient data that includes a geometric mesh representation of a body surface. The geometric mesh representation includes data points in three spatial dimensions. The method further includes generating a graphical user interface indicating an amount of the postural deviation.

Yet another embodiment of the present disclosure relates to a method of determining a postural rating of a body portion of a human body. The method includes determining a first structural alignment of a first body portion based on patient data that includes a geometric mesh representation of a body surface. The method further includes determining a first postural rating of the first body portion based on a deviation of the first structural alignment from a first nominal value.

Yet another embodiment of the present disclosure relates to a method of exercise prescription. The method includes determining an exercise routine based on patient data that includes at least one of pain pattern data indicative of an amount of pain associated with a body portion of a patient or a postural deviation of the body portion.

Yet another embodiment of the present disclosure relates to an apparatus. The apparatus includes a control unit including memory storing machine readable instructions and a processor. The machine readable instructions are configured to cause a processor to perform operation. The operations include placing a first anatomical landmark on a geometric mesh representation of a body surface, where the geometric mesh representation includes data points in three spatial dimensions.

Among other benefits, the systems and methods described herein improve accuracy in the diagnosis of physiological conditions that are difficult to detect and quantify using existing methods. Additionally, and as opposed to conventional computational data analysis methods, the systems described herein can reduce processing time to identify issue areas in need of attention or treatment. Moreover, patient data is captured from scans of the body that can be obtained remotely, without requiring the patient to interact with a clinician or visit a hospital or clinic in person. The scans and assessment methodology employed by the system ensures accurate measurement results that are reproducible across multiple users. In contrast to traditional, in-office measurement techniques or surface analyses, the system of the present application can take measurements from anywhere along the patient's body, and is not limited to individual measurements with respect to only two or three points along a patient's body. The system utilizes pre-configured and interactive data analysis techniques to rate and/or score overall performance and highlight problem areas to the patient and clinician in a manner that is not achievable through in-person treatment methods or existing automated techniques. These ratings are reported to the patient using advanced visualization techniques through an interactive GUI. The system also generates targeted exercise prescriptions based on the data analysis, enhancing consistency in treatment between different patients and improving the reliability of the results. Finally, the system uses the patient data from assessments to predict improvements and patient vulnerabilities, which can also be used to inform and encourage patients during the course of treatment.

Example Clinical Screening and Assessment System

Figure 2:
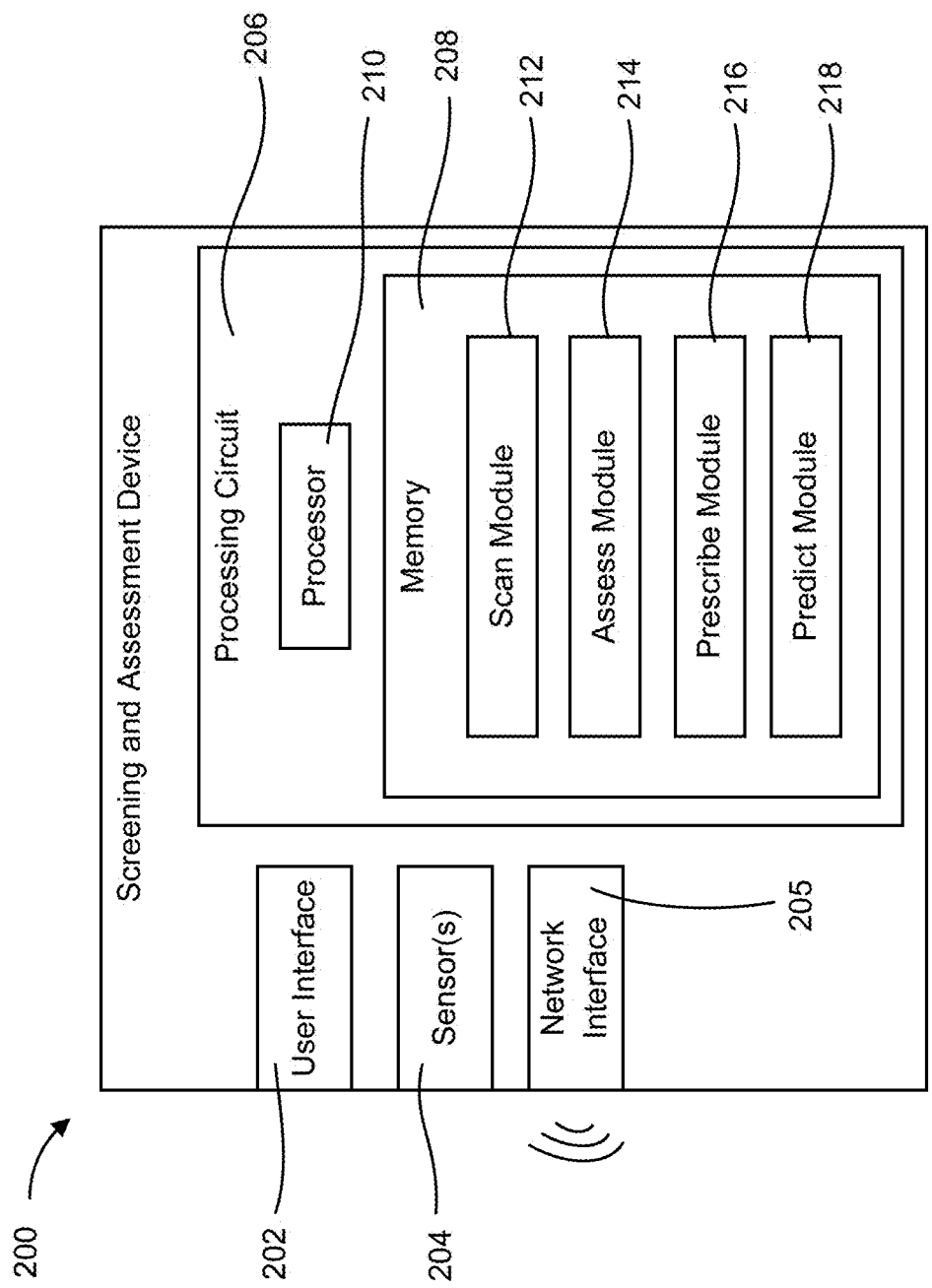
FIG. 2 is a block diagram of a clinical screening and assessment device, according to an embodiment.

Referring to FIG. 1, a schematic diagram of a system 100 for clinical screening and assessment is shown, according to an embodiment. The system 100 may be implemented as software (e.g., application, program, etc.) on a stand-alone computing device or using multiple devices that are connected through a network (e.g., a cloud computing environment, including a remote computing device and a network and/or cloud server, etc.). For example, FIG. 2 shows a block diagram of a clinical screening and assessment device, shown as device 200, that implements the system 100 of FIG. 1. The device 200 may be a mobile phone, tablet, a laptop or desktop computer, a scanning device (e.g., a digital camera), or any other portable or non-portable computing device. As shown in FIG. 2, the device 200 includes a user interface 202 (e.g., a touchscreen display, keypad, a microphone, a speaker, or another form of input/output device or human-machine interface, etc.) configured to receive user inputs and/or present information to a user; at least one onboard sensor 204 configured to capture images (e.g., an optical sensor, camera, etc.); a network interface 205 (e.g., a communications interface such as a transceiver, etc.) configured to receive and/or transmit data from the device 200 to other computing devices or systems; and a processing circuit 206 including memory 208 and a processor 210. The device 200 also includes a power source (not shown), which may be any wired or wireless power supply. In other embodiments, the device 200 may include additional, fewer, and/or different components.

As shown in FIG. 1, the system 100 includes a scan device 102, a scan block 104, an assess block 106, a prescribe block 108, and a predict block 110. In other embodiments, the system 100 may include additional, fewer, and/or different blocks. As shown in FIG. 2, each of the scan block 104, the assess block 106, the prescribe block 108, and the predict block 110 may be implemented as separate modules in memory 208 (e.g., as modules with computer-readable instructions that implement the functionality of each block) of the device 200, shown as scan module 212, assess module 214, prescribe module 216, and predict module 218, respectively. As such, the terms "block" and "module" are used interchangeably herein to describe the various functionalities provided by different aspects of the system 100. In other embodiments, at least one of the scan block 104, the assess block 106, the prescribe block 108, and/or the predict block 110 may form part of a separate control circuit that is communicably coupled to the processing circuit 206, or part of a separate computing device that is communicably coupled to device 200, or another system configuration that implements the methods and functionality described herein. In still further embodiments, two or more modules may be encompassed in a single computing device, control circuit, or processing unit/block.

It will be appreciated that the hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor (e.g., processor 210) may be a microprocessor, or, any conventional processor, controller, microcontroller, or state machine. The processor 210 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory 208 (e.g., memory, memory unit, storage device, database, etc.) may include one or more devices (e.g., RAM, ROM, Flash memory, hard disk storage) for storing data and/or computer code for completing or facilitating the various processes, layers and modules described in the present disclosure. The memory 208 may be or include volatile memory or non-volatile memory, and may include database components, object code components, script components, or any other type of information structure for supporting the various activities and information structures described in the present disclosure. According to an exemplary embodiment, the memory 208 is communicably connected to the processor 210 via a processing circuit 206 and includes computer code for executing (e.g., by the processing circuit or the processor) the one or more processes described herein.

As shown in FIG. 1, the scan device 102 is configured to capture patient data including scan data of a body surface and/or survey data from the patient. The scan data may include images of a person's body (e.g., a front image, a rear image, a side image, etc.) and/or video data (e.g., multiple images distributed in time) of the person's body in motion. The scan data is captured using the software on the scan device 102 and processed by the scan device 102 and/or another computing device (e.g., device 200 of FIG. 2) to generate an accurate geometric mesh representation of the patient's body from the captured data. In some embodiments, the scan data is transmitted to a second computing device (e.g., a network server, etc.) that is remote from the scan device 102 for further processing. In at least one embodiment, the mesh includes data points distributed spatially in three dimensions, with various data points corresponding to key landmarks along the patient's body (e.g., points along the surface of the skin at different locations along the body, etc.) and/or skeletal locations within the body (e.g., joints, vertebrae, etc.).

As shown in FIG. 1, the scan block 104 generates the mesh from the scan data and transmits the mesh, along with any survey data, to the assess block 106 for further processing. The assess block 106 includes algorithms to evaluate the posture and movement of the scanned individual from the mesh. The algorithms may be pre-configured 112 or may be specified interactively 114 by the user (e.g., by the patient or clinician through the user interface 202, etc.). For example, a pre-configured algorithm may be used to determine an amount of spinal misalignment (e.g., a straightness of the spine) by determining certain points along the mesh, particular spatial positions along the body, and comparing the discrepancy between these points (or curves generated therebetween) with values that are indicative of a nominal/healthy spinal alignment. These algorithms may also use responses from patient surveys to facilitate calculations (e.g., to identify focus areas, areas of the body where the user is experiencing pain, levels of pain, etc.). In some embodiments, interactive algorithms (e.g., user-specified algorithms) may be specified by the user, by selecting individual data points and/or landmarks along the mesh, through the user interface, and specifying calculations to be performed on the selected data.

The assess block 106 may use the pre-configured 112 and interactive 114 algorithms to determine health ratings and/or scores that are indicative of an amount of structural misalignment, limits on range of motion, and/or general performance of a body component/area. For example, the assess block 106 may be configured to determine a postural alignment and stability rating for a specific body area (e.g., spinal misalignment, shoulder elevation, head posture, etc.) that is indicative of an amount of postural deviation (e.g., structural misalignment) relative to neutral values. The assess block 106 may be configured to combine these ratings from different body areas to determine an overall health rating and/or score for the patient.

The assess block 106 may be configured to generate reports summarizing key outputs from the pre-configured 112 and interactive 114 algorithms. In particular, the assess block 106 may be configured to overlay health ratings, amounts and/or levels of measured postural deviation, and other health metrics onto a visual representation (e.g., visualization) of the patient's body. The user (e.g., patient or clinician) may interact with the visualization via the user interface to understand and engage with static and/or dynamic patterns of the patient's body.

The prescribe block 108 determines an exercise regimen based on data from the assess block 106 (and/or scan block 104). The prescribe block 108 may include a database (e.g., accessible from memory 208 of device 200 of FIG. 2) storing a library of exercises that the system can prescribe to treat the patient's physiological conditions. The prescribe block 108 may implement detailed prescription algorithms (e.g., routine selection logic) to select and prioritize exercises based on the patient's unique combination of measured deviations, vulnerabilities, and needs. The prescribe block 108 outputs a set of routines to be practiced by the patient to improve their underlying conditions (e.g., reduce pain, improve posture, improve range of movement, etc.). In at least one embodiment, the outputs may be provided to a clinician for assessment, revision, and approval before being prescribed to the patient.

The predict block 110 is communicably coupled to the assess block 106 and the prescribe block 108 and receives data from the assess block 106 and the prescribe block 108. The predict block 110 is configured to tabulate changes in patient measurements over time to track changes and improvements in patient posture and performance (e.g., reductions in pain levels, changes in range of motion, etc.). The predict block 110 is also configured to approximate future performance based on historical trends and/or data from similar treatment regimens experienced by other patients. In some embodiments, as shown in FIG. 1, the predict block 110 may be configured to adjust exercise prescriptions based on historical data (e.g., observed outcomes as treatment progresses, data from other patients participating in similar treatment regimens, etc.). In particular, the predict block 110 may be configured to implement machine learning to continuously optimize algorithms for issue diagnosis and exercise prescription. The predict block 110 may feed this information back into at least one of the scan block 104 (e.g., by requesting additional information from the scan block such as body surface images during range-of-motion exercises to improve exercise prescription), the assess block 106, and/or the prescribe block 108.

The details of the various operational blocks of the system 100 are described in further detail below.

Scan Operations

As shown in FIG. 1, in the scan block 104, the scan device 102 receives survey data from the patient. The survey data may include personal information (e.g., reference information) for the patient (e.g., phone number, email, date of birth, etc.). The survey data may also include the patient's physical information (e.g., age, height, weight, gender, activity level, problem/focus areas, areas of discomfort/pain, pain levels and duration, type of pain/discomfort, current medications, past treatments, etc.) to enable accurate scaling of the 3D mesh, identify problem areas, and establish levels of discomfort and/or pain in different body areas and/or zones. In at least one embodiment, the scan block 104 receives survey data from user (e.g., patient) input into the scan device 102. The scan device 102 may present the user with an interactive GUI that may query the user for patient information. For example, FIG. 3 shows an example of a patient intake form that may be presented to the user by the GUI. In at least one embodiment, the intake form is a single document that the user may scroll through and specify the requested information (e.g., using a keypad, touch screen, and/or verbal commands input via the user interface of the scan device 102). In another embodiment, the GUI may provide a curated walkthrough to assist the user in specifying the correct information.

Note that the systems and methods of the present application may be integrated in partnership with a clinical institution, or via an independent business associate. Regardless of the relationship and/or status, the system (and business implementing and/or maintaining the system) shall make every reasonable effort to comply with the Privacy and Security Rules under the Health Insurance Portability and Accountability Act of 1996 (HIPAA), the Health Information Technology for Economic and Clinical Health (HITECH) Act of 2009, and the regulations promulgated thereto. The system and/or business associated therewith complies with these federal laws, applicable state laws, including but not limited to the California Privacy Rights and Enforcement Act of 2020 (the "CPRA"), the California Consumer Privacy Act of 2018 (the "CCPA"), and the European Union General Data Protection Regulation ("GDPR") regarding the privacy and security of protected health information.

Additionally, the scan device 102 captures scan data, including image data (e.g., video, truecolor image data, red-green-blue (RGB) color model images, etc.) and/or active or computed depth sensing information for a patient's body. The scan data may include individual images (e.g., pictures, etc.) of the patient from different sides of the patient to obtain volumetric data of the patient's body. The scan data may also include video data (e.g., multiple images spaced in time) to capture the patient's movement (e.g., range of motion, etc.). The scan data may be captured by a camera or another optical sensor, which may form part of a mobile computing device (e.g., mobile phone, tablet, or another computing device) and/or the screening and assessment device 200 of FIG. 2. In at least one embodiment, the scan data may be captured using multiple capture devices. The scan data from the capture devices may be combined to improve image quality and/or capture different aspects of the body geometry or movement. For example, a first set of scan data may be captured using a camera that is integrated with a user's mobile computing device (e.g., a camera on a mobile phone). This first set of scan data may include colored photographs (e.g., RGB data, etc.) of the user and may be used to identify the location of the user's joints, for example, or other landmarks of interest. The camera may be stationary or in motion. A second set of scan data may be captured using a light detection and ranging device (LiDAR or time of flight or depth sensors, such as Azure Kinect; 3D laser scanning; etc.) that uses light in the form of a pulsed laser to measure ranges (variable distances) to different parts of the user's body. The second set of scan data can be used to produce an accurate 3D representation of the imaged patient without having to capture the user from different perspectives and/or angles.

The LiDAR data and RGB images may be combined (e.g., stitched together and synched) to generate a 3D mesh of the patient from a single perspective and/or angle that includes depth information (e.g., volumetric information about a person's body in three dimensions) that could not be as accurately obtained using only a single RGB image.

The scan device 102 may include a GUI that curates the capture of patient data using the camera onboard the scan device 102. The GUI may include a list of instructions (e.g., readable text) that the patient can follow to obtain the required scans (e.g., images) of their body. The instructions may also be transmitted to the user through speakers on the scan device 102 while the images and/or video are being captured (e.g., "turn so that the left side of your body faces the camera," etc.).

Scan data may be processed by the scan device 102, via software on the scan device 102 (e.g., scan module 212), and/or transmitted to a remote server for further processing. The software produces an accurate geometric mesh representation of the body surface from the captured scan data. The geometric mesh representation (e.g., mesh, etc.) may include data points in three spatial dimensions (3D) of the patient's body along an outer surface and interior to the patient's body. In some embodiments, the mesh may be animated to match a movement performed by the patient. The 3D volumetric mesh is representative of the person's body structure (e.g., posture, skeletal alignment, form during movement, etc.). Additional details regarding the capture and processing of scan data (e.g., image and/or video data) may be found in U.S. Pat. Nos. 9,161,019 and 10,244,228, the entire disclosures of which are incorporated by reference herein.

An example method of capturing scan data includes receiving, via the user interface of the scan device 102, a request to perform a scan (e.g., to create a new patient/user). The method may include presenting the user, via the GUI, with a patient intake form, and receiving personal and physical information from the user. This may include receiving an indication of pain-levels associated with various zones and/or other demographic information from the user (e.g., information that can be used as a training set for a machine learning algorithm to facilitate automatic generation of a 3D model and patient profile).

The method may also include initiating, via the scan module 212, in response to user input, a scan capture of a surrounding environment in which the user and/or patient will be scanned. The scan capture may include taking an image via a camera onboard the scan device 102 and/or using a separate camera and/or sensor that is communicably coupled to the scan device 102. The method may include establishing the environment for the 3D model by determining a ground plane and/or other reference geometry from the background scan capture.

Figure 4:
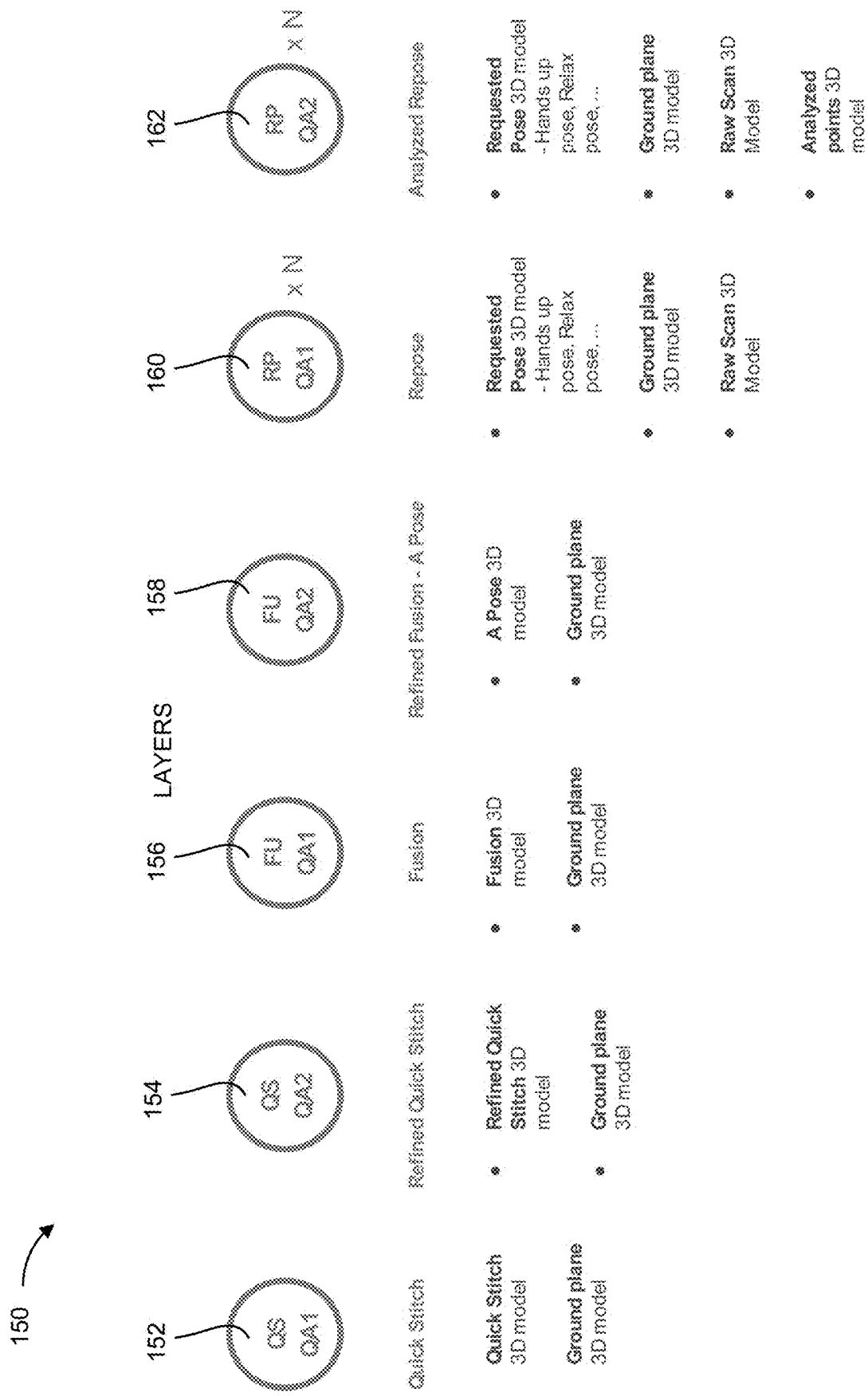
FIG. 4 is a flow diagram of a method of generating a 3D model from scan data, according to an embodiment.

The method may also further include initiating, in response to user commands and/or a preprogrammed sequence, a scan capture of the patient. Referring to FIG. 4, a portion of method 150 of scanning a patient is shown, according to an embodiment. The method 150 includes performing a first scan capture of the user (e.g., patient) in the background environment in a first pose (e.g., position). For example, the method 150 may include scanning the user in an A-pose (e.g., standing straight up, with arms to the side but not touching the body) from multiple angles around the user. The method 150 may include commanding the user, via the GUI and/or by generating audible cues, to reposition his/herself (e.g., rotating in 90 degree increments) every couple of seconds to obtain a full 360 degree scan of the patient in the A-pose. In another embodiment, the method 150 may include scanning the patient from at least one angle using a combination of RGB images and LiDAR, so as to develop a volumetric image of the patient from at least one side. The initial scan capture of the patient provides foundational data (e.g., topological data) that may be used to complete a dynamic fusion for the initial 3D model and to facilitate the generation of 3D models of the user in other poses.

The method 150 further includes performing an initial stitch operation, at 152, to generate an initial 3D representation of the topological data from the scan data within moments of the scan being performed. The initial 3D representation may be a first draft of the 3D mesh and/or model data. At 154, the mesh is refined to generate a refined, second version of the initial the 3D representation while processing continues. In some embodiments, this second version of the model may be an output from at least one iteration of a quality assurance and/or review process (e.g., expert review, automatic calculations and/or checks by the scan block 104, etc.). At 156, the topological data goes through dynamic fusion to form a foundational model, which may serve as a starting point for all reposes of the model scan session (e.g., to facilitate generation of the mesh in different poses and/or user positions). At 158, the 3D model from the dynamic fusion operation is refined to generate a final baseline model which can be used for the remaining reposes.

Operations 160 and 162 are the initial and final parts, respectively, of the processing pipeline that produces the remaining poses (e.g., 3D models of the patient in different positions). At 160, the foundational elements from the topological model are used to produce a semi-final 3D volumetric model of a specified position (e.g., pose). At 162, the semi-final 3D model is processed through a final quality assurance check resulting in a finalized, high quality 3D volumetric model of the specified position.

The method may be repeated to capture another pose (e.g., a second, third, etc.) of the user, by repeating the scan capture with the user positioned in different poses (e.g., relaxed pose with the patient's arms down at their sides, an arms overhead pose, a squat pose, etc.). The method may include providing the user with an instruction to alter their position after completing a scan capture for each pose, and/or the position of the scan device. The instruction may be provided via a text box through the GUI, and/or via audio commands from the user interface. For example, the scan device 102 may generate an audible message instructing the user to "please raise your hands above your head," to "move to a relaxed pose," to "perform a squat," repose, and/or another suitable command. The GUI may also allow present visually-perceptible icons or links that redirect the user to a page that provides more detail about each command and the requested pose (e.g., a page that clarifies how to perform each pose). Alternatively, or in combination, the user may request further instructions and/or clarification by speaking into the microphone and, in response, the GUI may be configured to present a page with additional information about the requested pose (and/or an audible output that clarifies how the user should reposition themselves). During the scan capture, the patient may again be instructed to rotate in 90 degree increments to obtain a full 360 degree view of each pose.

In some embodiments, the method may include using topological data from the initial scan capture (e.g., in the A pose) to facilitate the generation of the 3D model in each pose. For example, the method may include translating portions of the initial 3D model, particular landmarks and/or mesh points from the initial 3D model, based on the measured range of movement during repose (e.g., while performing an exercise, etc.). Among other benefits, the scan data obtained from the repose operations can be used to determine the patient's range of motion. The combination of scanned movements and poses will be used to perform various different assessments and biometric screens, as will be further described.

After generating the mesh, the software (e.g., the scan module 212) is configured to place anatomical landmarks onto the mesh to facilitate analysis of the data for various portions of the body in the assess block 106. The scan module 212 may be configured to upload and/or transmit the mesh—along with various layers of scan data, RGB images, etc.—to a cloud management service (e.g., cloud, scan data processing server, remote and/or network computing device, etc.). For example, the scan module 212 may make an application programming interface (API) call to the cloud management service including the scan data. In other embodiments, placement of landmarks may be performed via the scan device 102 itself.

The landmarks correspond with specific features of the patient's body (e.g., the location of the patient's spine, shoulder location, and the location and orientation of other body features). In at least one embodiment, the landmarks are automatically placed onto the 3D mesh by the scan module 212 or the assess module 214, as will be further described with respect to various assessment screens of different body areas. The landmarks may be specified using skeletal and/or soft tissue anatomy that may be identified from the scan data using algorithms in the software. The methods of automatic landmark placement described herein can improve landmark placement accuracy, repeatability between different patient scans, and can also reduce computational/processing time (for example, as compared to iterating through individual vertex positions along the geometric mesh representation of the patient). The landmarks may include primary landmarks that are identified using topological and geometric relationships along the mesh and/or from at least one reference set of patient data, and/or secondary landmarks that are defined based on the location of the primary landmarks. For example, the secondary landmarks may include body features that are related to the placement and orientation of different body parts of the patient. Beneficially, the landmarks facilitate comparison of measurements, structural alignment, and the like, between individuals.

In some embodiments, the scan module 212 may be configured to access landmark tables that detail the different landmarks that may be identified by the scan module 212 and/or the assess module 214 from the 3D mesh (e.g., from the geometric mesh representation of a patient). A first column of each table may indicate the body element corresponding to each landmark. A second column of each table may indicate how the body element may be located automatically by the system (e.g., based on a position of other landmarks, machine learning, etc.).

Landmark identification may be repeated for a plurality of patients based on similar sets of scan data (images taken with the scan device of the same pose for different patients). This data, including scan data for multiple patients, may be collected and used by the scan block 104 and/or a separate scan feedback block as inputs (e.g., a training set) to a machine learning algorithm. The machine learning algorithm may analyze the data to identify similarities between the selected data points and corresponding features in the scan data that are the same or similar for each patient. For example, the machine learning algorithm may correlate changes in color (e.g., color gradient, etc.), another commonality and/or combination of commonalities in an RGB image (or multiple scan or image types) to the location of specific landmarks (e.g., a patient's eyes, etc.). The machine learning algorithm may then use this data to recognize the location of the specific landmarks in scan data from other patients automatically. The machine learning algorithm may also take into account changes in depth with color by comparing the scan data with depth information from LiDAR scans of the patient in the same pose (e.g., position). In this way, the machine learning algorithm may be trained to recognize landmark positions in a similar manner as is done during a visual identification of body elements by a clinician or third party operator. In some embodiments, the clinician, third-party operator, and/or user may also be able to manually specify tabular information for additional landmarks beyond the pre-configured landmarks. The landmark definitions may be stored in system memory (e.g., the scan module 212 in FIG. 2).

In at least one embodiment, the scan module 212 is configured to automatically determine the location of landmarks by averaging data across multiple patients and/or users that have been scanned. The scan data for each patient may be added to a reference set of patient data stored in memory. The scan module 212 may be configured to retrieve and analyze the reference set to determine, for example, an average height of a skeletal or soft tissue anatomy of a patient, such as a patient's knee, elbow, shoulder, and/or other landmark as measured from a ground plane based on the reference set, as will be further described.

Figure 5:
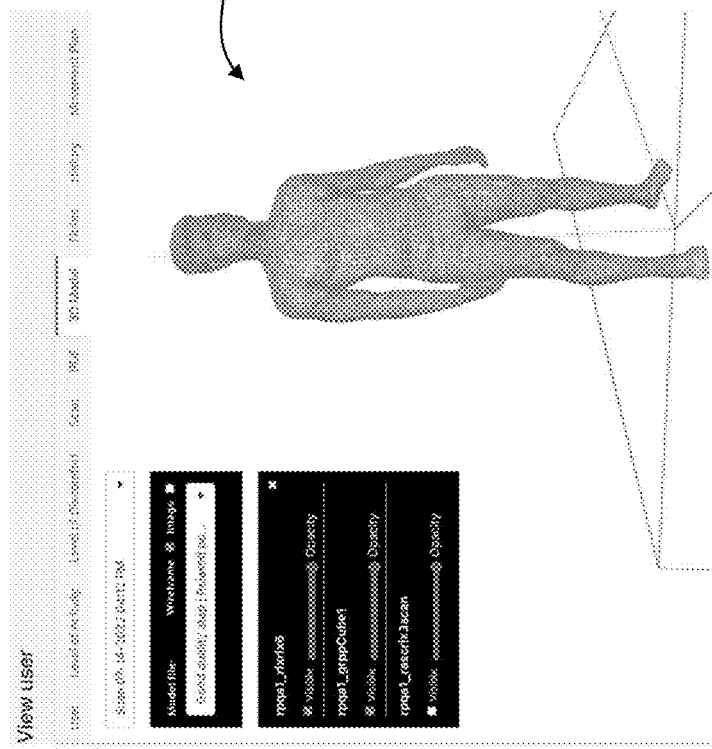
FIG. 5 is a display screen of a 3D volumetric mesh of a user, according to an embodiment.
Figure 6:
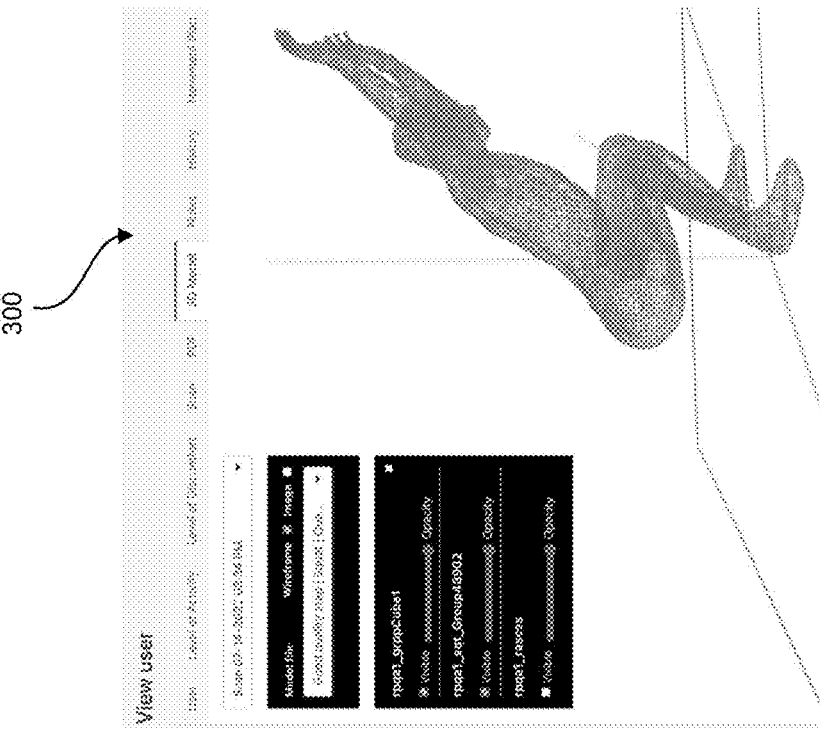
FIG. 6 is a display screen of a rotated 3D volumetric mesh of a user, according to an embodiment.

FIGS. 5 and 6 show example views of the volumetric mesh generated by the scan module 212 and/or the assess module 214. In contrast with existing forms of patient analysis and treatment, the system of the present disclosure is configured to generate a full 3D volumetric mesh from the images of the patient's body. The mesh extends in a transverse direction through the core region of the body, which allows for identification and accurate assessment of features that are interior to the patient's body. As shown in FIG. 6, and in addition to the static screens of the patient in fixed position, the 3D mesh can be used to accurately identity joints and other interior features of the patient's body during patient movement (e.g., a squat as shown in FIG. 6).

In another embodiment, the scan module 212 and/or the assess module 214 is configured to place user-specified landmarks onto the mesh via the GUI 300 on the scan device 102 and/or remotely at the cloud management service (e.g., by a clinician, third-party operator, etc.). For example, the user and/or operator of the cloud management service, via the GUI 300, may select specific points from the volumetric mesh and/or pixels from the image data to form a group, and different measurements and monitoring tools can be applied to the group to quantify changes to these user-specified body features over the treatment period.

The scan module 212 and/or the assess module 214 may display, via the GUI 300, the 3D model of the patient and interactive tools to facilitate manipulation of the model and manual specification of landmarks along the 3D model. The GUI 300 may also be configured to filter patient models, for example, by name, session, operator and/or reviewer (e.g., the person placing and/or reviewing landmark position), patient, data source, date of model creation or upload, and the like.

The GUI 300 may also allow the user to manipulate the 3D model, for example, to adjust the visibility of, or otherwise modify, different layers of the 3D model (e.g., to adjust the transparency of a layer, to toggle between different layers such as between the solid 3D model and the mesh, to overlay RGB images onto the 3D model, etc.). The GUI 300 may also include tools (e.g., visually-perceptible icons, selectable tabs or other groupings, adjustable graphical indicators, etc.) that allow the user to rotate the model, zoom in or out, and to view different poses.

In some embodiments, the software is configured to determine (e.g., automatically based on past analysis information or from the patient survey data) initial vulnerabilities (e.g., vulnerability levels, etc.) for different body areas and/or zones based on their analysis of the patient's posture from the 3D model. The software may also specify scores (e.g., initial risk scores based on algorithms or initial point-to-point determinations from the 3D model, etc.) for different body areas, which may correspond with vulnerability levels, and may be used by the scan module 212 and/or the assess module 214 to facilitate determination of the exercises that are prescribed to the patient.

Figures 7, 8:
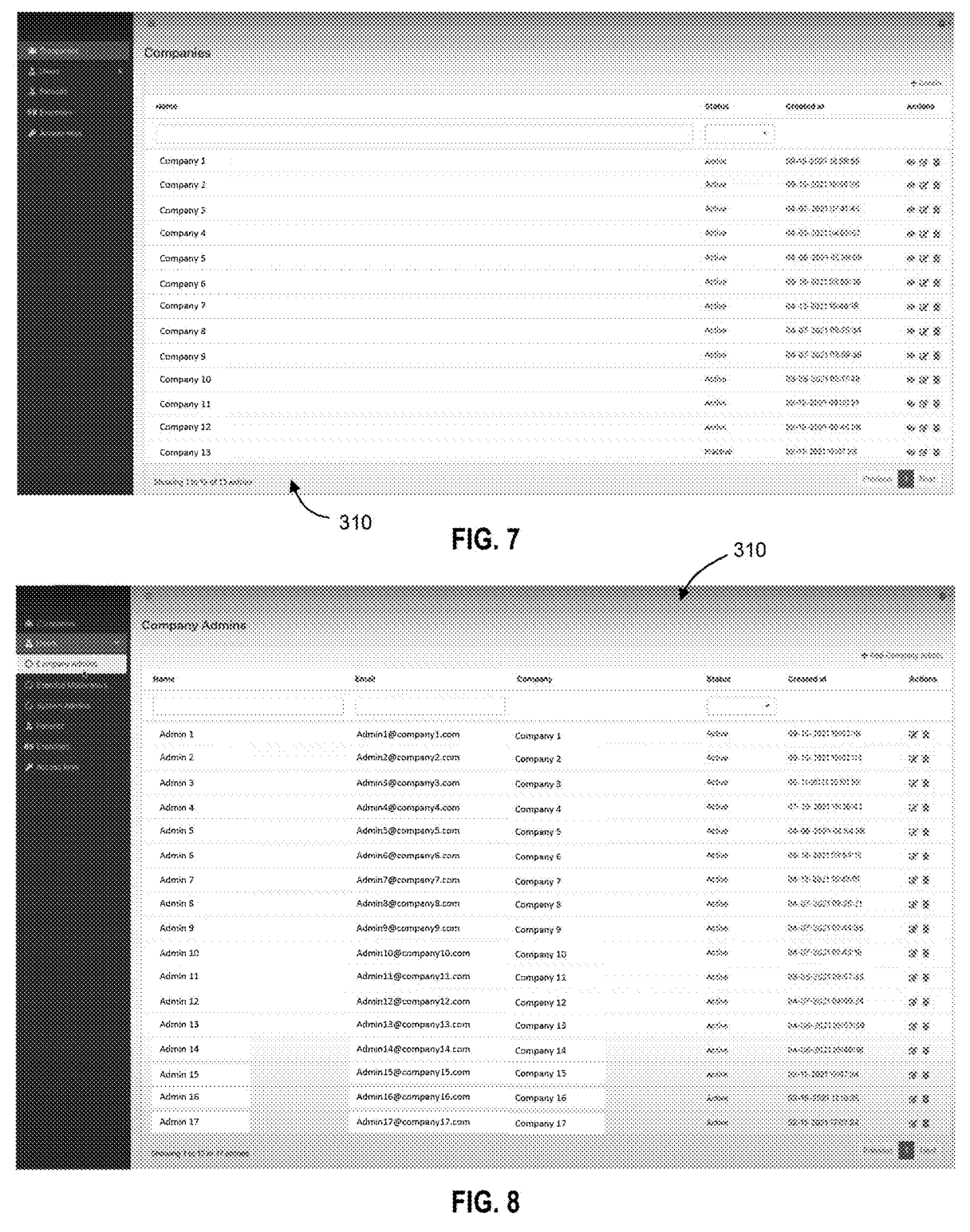
Figure 9:
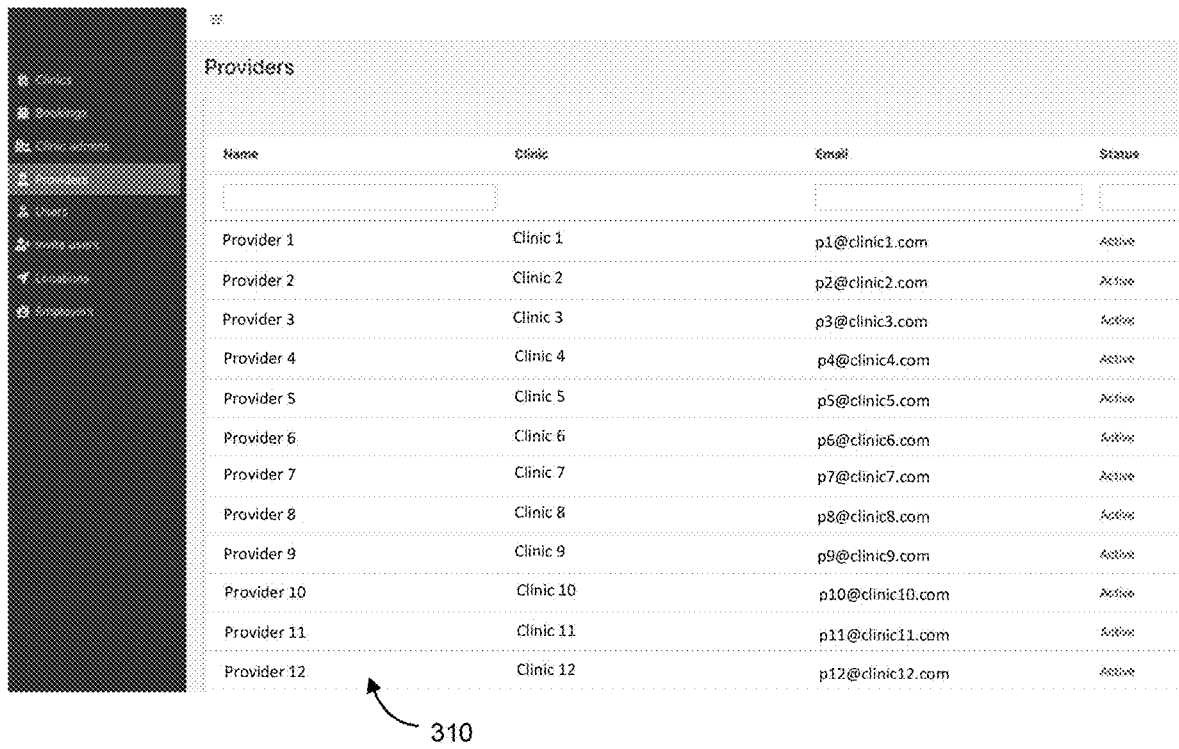
Figure 10:
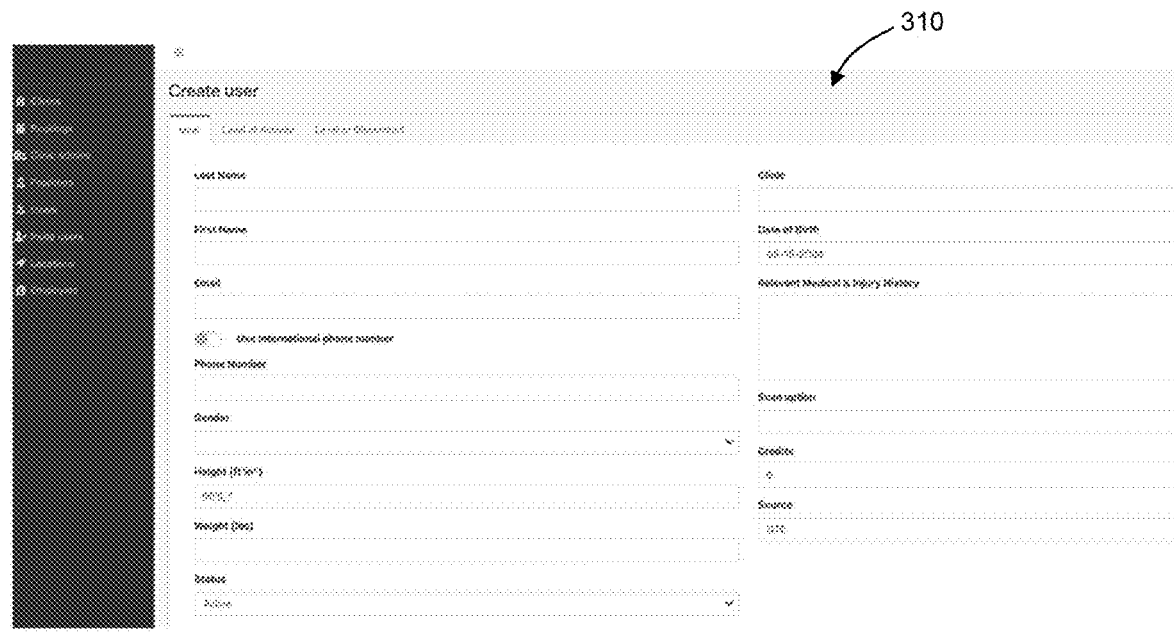
Figures 12, 13:
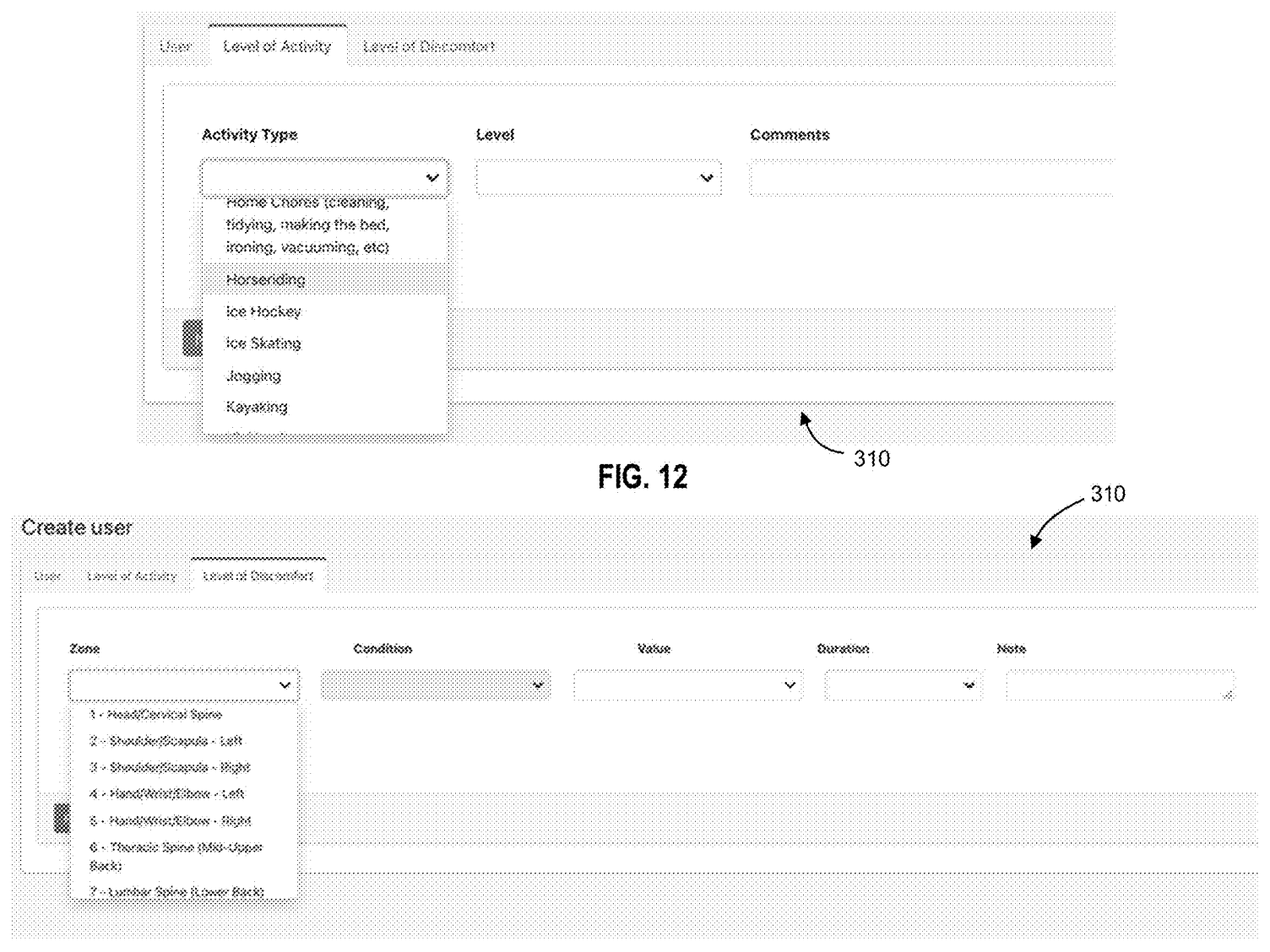

The GUI 300 may be included as part of a full web interface that is accessible through the internet and/or software application from a computing device (e.g., mobile phone, personal computer, etc.). The GUI 300 may also integrate administrative tools to manage access to and sharing of patient data. Referring to FIGS. 7-13, an administrative GUI 310 is shown, according to an embodiment. The administrative GUI 310 allows an operator to specify which companies (e.g., clinics, etc.) have access to patient data, and patient-specific access preferences. As shown in FIGS. 7-9, the administrative GUI 310 may be used to specify a list of clinicians (e.g., doctors, physical therapists, providers, etc.) within each clinic and patient-specific access preferences and details (e.g., for each clinician, clinic, etc.). The scan module 212 and/or the assess module may also allow a user to activate or deactivate companies through the administrative GUI 310. The administrative GUI 310 may also allow a user to specify relationships between patients and their clinics to ensure that patient data and records are secured stored.

Figure 14:
FIG. 14 is an application programming interface (API) library for a clinical screening and assessment system.

The administrative GUI may also include survey data from the patient to facilitate analysis and review of the scan data. For example, as shown in FIGS. 9-13, the administrative GUI 310 may include details regarding areas of discomfort for the patient, pain levels, areas of discomfort, and the like. The functionality of the administrative GUI 310 may be accessible from the scan device and/or another remote computing device through API calls, which facilitate transfer of scan data and retrieval of analysis results. For example, the administrative GUI 310 may include a library of API calls to facilitate data transmission and interaction with other computing devices. As shown in FIG. 14, the library may form part of a software development kit (SDK) that may be distributed to the scan device when downloading the software application. It will be appreciated that the API calls provided in FIG. 14 are shown for illustrative purposes only. Many other API calls may be implemented to integrate backend systems with the scan device, clinician device, remote server, and/or other computing devices.

In at least one embodiment, the primary landmarks may be used to optimize the accuracy of the volumetric mesh by providing corresponding points between raw frames and the completed mesh. For example, after collecting an image and/or set of images of the user's body, the GUI may be configured to present the collected images to the user and may request that (e.g., query) the user to identify specific landmarks along the image. For example, the GUI may present an image of the front of the patient's body in a first pose. The software may be configured to present, via the GUI, a dialog box and/or audible notification that prompts the user to select (e.g., using a touchscreen interface or another human-machine interface) a first location along the image that corresponds with the user's belly button, shoulder joint, elbow, and/or any other body element. The software may be configured to generate the mesh, in part, based on the location of the manually specified body elements. For example, the software may be configured to seed the mesh starting at certain body elements, to alter the mesh shape and/or number of points in different areas of the body to improve mesh resolution in certain body areas, or otherwise structure the mesh based on the user-specified body elements.

The software is also configured to perform various quality assurance operations during processing of the mesh to ensure that the patient's body is accurately captured and that the placement of anatomical landmarks is consistent between scans. For example, as described above, multiple cameras or sensors may be used to improve the quality of the scan data. Scan data from a mobile computing device (e.g., iPhone, etc.) may also be up-sampled using a higher resolution device (e.g., close-up images at different spacing from a user, etc.), or through interpolation techniques to up-sample an image to higher quality. For example, an initial scan be performed based on a first image of the patient's body. Portions of the image may then be refined using close up images of the user's body in specific regions of the mesh (e.g., a close up image of a user's shoulders may be used to generate a mesh of the user's shoulders, and the refined mesh may be applied over top of the first image and/or used to improve detection of landmark locations for the first image). In another embodiment, interpolation may be used to add pixels and adjust for color variations to increase the resolution of the image. In another embodiment, the scan block 104 may be configured to use machine learning (e.g., via a convolutional neural network, a recurrent neural network, or another form of deep neural network) to account for how similar images have been up-sampled, and to automatically adjust the scan based on past operations. A LiDAR device may also be used to confirm how depth changes between pixels and the LiDAR data may be used as an input to the machine learning algorithm to improve accuracy of the resulting scan and/or image. The output from the scan block 104 is a highly accurate 3D representation of the surface of the patient's body, including the placement of anatomical landmarks.

Assess Operations

Referring to FIG. 1, in the assess block 106, the system 100 (e.g., device 200 of FIG. 2) is configured to analyze the mesh and landmarks, determine deviations of the mesh and anatomical landmarks from neutral values (e.g., healthy values, acceptable values, average values, values at neutral balance, etc.), determine health and/or performance ratings or ratings for various body areas based on the deviations, and provide a curated summary of patient data to facilitate user review and understanding of the results.

The system 100 (FIG. 1) is configured to evaluate posture and movement of the scanned patient using biometric data from direct measurements on landmarks and the volumetric mesh. In at least one mode of operation (e.g., a preconfigured assessment mode), the system 100 is configured to perform a biometric screen that analyzes specific body areas of the static mesh (e.g., primary landmarks and/or secondary landmarks, data points, etc.) to determine deviations in structural alignment from neutral (e.g., average) values in each body area and/or discrepancies in structural alignment between different body areas.

The specific body areas of interest, and the neutral values used to determine the deviations, may be predefined values in system memory (e.g., memory 208 of FIG. 2), and may be automatically applied to the scan data (e.g., 3D model with landmarks) received from the scan block 104. In some embodiments, the neutral values of structural alignment may be developed in consultation with professionals in the musculoskeletal (MSK) health field. In other embodiments, the neutral values of structural alignment may be average values across a plurality of patients (e.g., empirical data for average values of structural alignment). In the embodiment of FIG. 1, biometric screens may be performed to assess at least the following static patterns of the patient's body: (i) vertical load; (ii) head position; (iii) spinal mapping; (iv) scapular position; (v) thoracic position; (vi) pelvic position; (vii) leg length discrepancy; (viii) Q angle; (ix) calcaneal position; (x) stance; and (xi) cross pattern postural vectors, among others. The user (e.g., operator, clinician, patient, etc.) may also optionally use the software to measure distances and angles from the scan data, via a GUI, and/or select predefined measurement screens in the assess module 214 to display key angles and differentials. The user may also view, through the GUI, summaries of the calculations with indicators as to which differentials show the greatest potential for abnormality and/or possible pain points for the patient, as will be further described.

Figure 15:
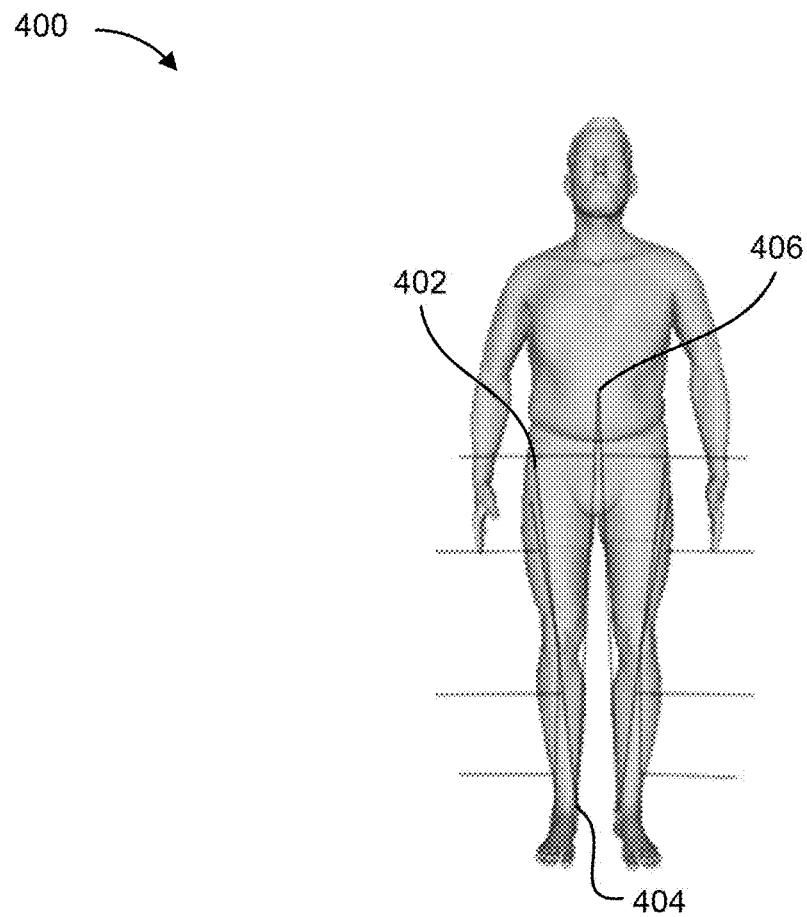
FIG. 15 is a display screen of a method of computing leg length using a clinical screening and assessment system, according to at least one embodiment.

By way of example, a biometric assessment 400 to evaluate a patient's leg length is shown in FIG. 15. The assessment 400 determines the true and perceived leg length of the patient's right and left leg, and assists in determining if a discrepancy in length is caused by imbalance or an underlying genetic condition. As shown, the system uses the landmarks in the geometric mesh representation of the patient to identify the body features of interest. In this example, the landmarks include points corresponding to the patient's umbilicus, medial malleolus, lateral malleolus, and knee. In other embodiments, the landmarks may include any other MSK features of the patient's body. The system is configured to determine a length between each of these landmarks (e.g., along a straight line between landmarks). In particular, the system is configured to calculate (1) a true length from ASIS to medial malleolus, (2) a perceived length from the umbilicus to medial malleolus, and a difference between these measurements. In the embodiment of FIG. 15, the system measures a straight line distance between two points on a first side of the 3D model (e.g., the ASIS to medial malleolus—point 402 to point 404—and the umbilicus to the medial malleolus—point 406 to 404) and then repeats these two measurements on a second side of the 3D model. The system may also be configured to compare lengths of each leg on opposing sides of the body to determine any discrepancies in leg length, and to display the actual leg length discrepancy measurement. For example, the system may be configured to calculate the difference between the two points on the first and second side of the body and to provide an indication to the user of the relative difference in leg length. In at least one embodiment, the software is configured to populate the results into a tabular summary that may be presented to a user through a GUI on a user device. The differentials presented in the tabular summary may be color coded to indicate a level of concern based on the calculated differential (e.g., how significant the disagreement is between measured values, etc.).

The tabular summary may be a guide table that provides additional detail about relevant landmarks for the analysis, which values are measured from the landmarks, how the calculation is performed, and the acceptable and unacceptable ranges for the calculated differential. The guide table may also be accessed by a user, via the GUI, to improve their understanding of the analysis results and to help them gage progress throughout the treatment regimen.

Figure 16:
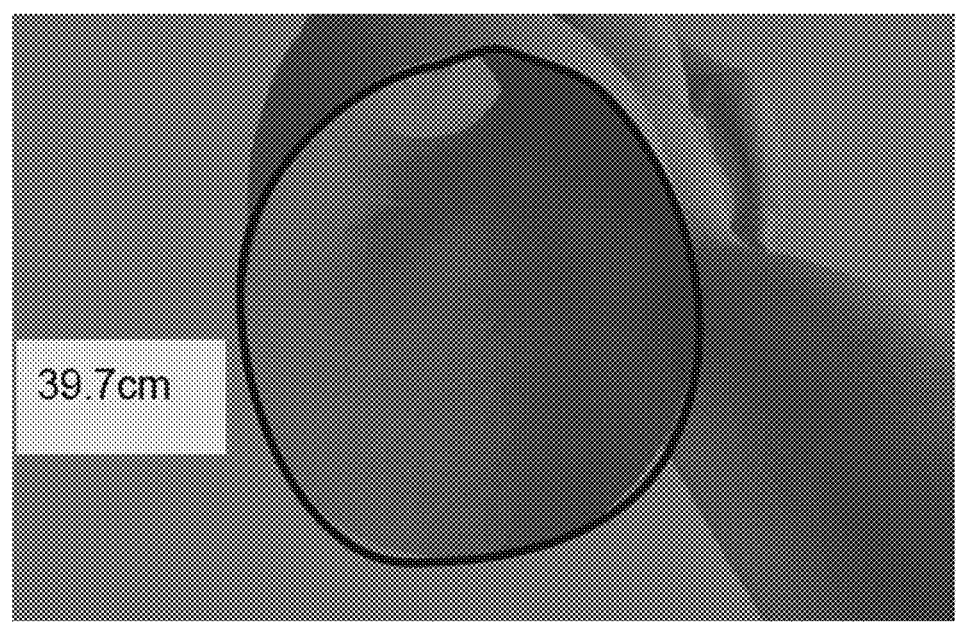
FIG. 16 is a display screen of a method of computing leg circumference using a clinical screening and assessment system, according to at least one embodiment.

As shown in FIG. 16, the system and/or software may also be configured to determine measurements of body features in 3D from the volumetric mesh. For example, the system may be configured to retrieve and analyze mesh data points on opposing sides of a patient's leg to determine a circumference and/or diameter of a patient's leg (e.g., a diameter of the leg at a central position along the patient's calf muscle, etc.). In this way, the system can determine areas of poor muscle development on different sides of the patient's body, and areas where exercises may be needed to develop the muscle and to improve patient posture and form.

Figure 17:
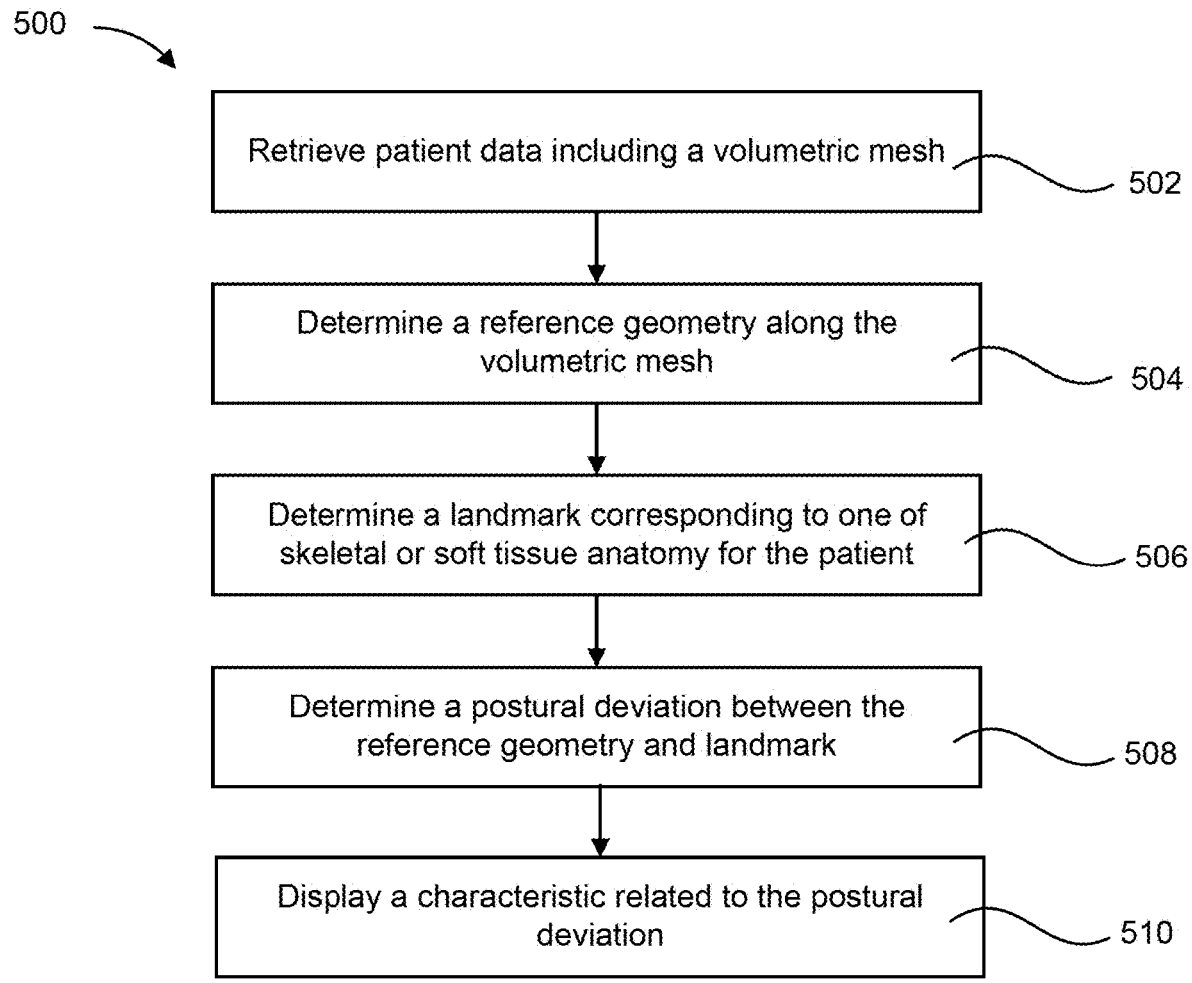
FIG. 17 is a flow diagram of a method of determining postural deviations for a human body, according to an embodiment.

Referring to FIG. 17, a flow diagram of a method 500 of determining postural deviations (e.g., measured deviations in posture from healthy/neutral values) is shown, according to an embodiment. The method 500 may be implemented by the device 200 of FIG. 2, for example, through a software application installed on the device 200 (e.g., through the assess module 214). As such, reference will be made to the device 200 when describing method 500. In another embodiment, the method 500 may include additional, fewer, and/or different operations. It will be appreciated that the use of a flow diagram and arrows is not meant to be limiting with respect to the order of flow operations. For example, in one embodiment, two or more of the operations of method 500 may be performed simultaneously.

At 502, the assess module 214 receives patient data including the volumetric (3D) mesh (e.g., of a patient's body, etc.), along with any survey data needed to establish parameter measurements using the mesh. The volumetric mesh may be generated by the scan module. Operation 502 may include retrieving, from memory (e.g., the scan module 212), patient data including a geometric mesh representation of a patient that is generated from scan data (e.g., images, RGB values, etc.) of a patient's body including a plurality of images of the patient from at least two sides of the patient. For example, operation 502 may include retrieving a geometry definition file that is representative of the geometric mesh representation. The geometry definition file may be an .obj file, an .stl file, or another type of 3D geometry exchange format. The geometry file may contain a three-dimensional object and all associated geometry, including the positions of each vertex, texture vertices, polygonal faces, free-form curves, etc. In at least one embodiment, the geometry definition file may include a plurality of data point corresponding to spatial coordinates of a plurality of vertices of the geometric mesh representation in three dimensions. The geometry definition file may also include a list of a plurality of faces forming the three dimensional geometric representation of the patient including both interior surface elements forming an outer surface of the geometric mesh representation and interior surface elements forming a body within the outer surface. Each face of the plurality of faces may include three vertex indices corresponding with the vertices that bound each face. Operation 502 may include interacting with the geometry definition file, for example, using a 3D mesh manipulation library to manipulate the mesh. The 3D mesh manipulation library may include a plurality of call function operations to generate new reference planes or coordinate axis to facilitate calculations. The library may also include call functions to cut or separate portions of the mesh, to approximate body geometry along references planes, to determine a volumetric slice through portions of the mesh, or otherwise interact with the geometry definition file. The call functions may manipulate the geometry file directly using pre-existing data, and without requiring regeneration of the mesh from scan data or image files, which can reduce processing times while maintaining calculation accuracy.

Operation 502 may further include generating and/or rendering a visual representation of the geometric mesh representation using the geometry definition file. For example, operation 502 may include decoding, by the processor of device 200, vertices and/or faces of the geometric mesh representation from the geometry definition file, and rendering an image corresponding with the geometric mesh representation on the GUI.

In some embodiments, operation 502 may also include receiving scan data from a patient and generating a geometry definition file corresponding to the geometric mesh representation. In such instances, operation 502 may further include generating the geometry definition file by determining a list of spatial coordinates (e.g., including an x-axis position, a y-axis position, and a z-axis position) of each vertex and/or a list of faces formed by the vertices (e.g., a list of polygonal faces, where each entry in the list includes at least three vertices from the list of spatial coordinates).

Operation 502 may also include retrieving data regarding the scale and/or resolution of the mesh from the geometry definition file. For example, operation 502 may include retrieving height information for the patient, and/or other reference data to calibrate measurements that are obtained using data from the geometry definition file.

At 504, the assess module 214 (and/or the scan module 212) defines a coordinate system for the mesh. Operation 504 may include defining coordinate axes for the mesh to facilitate calculations. The coordinate axis may be a Cartesian coordinate system as shown in FIG. 18. The coordinate axes may be defined based on patient orientation; for example, by aligning a first coordinate axes with a surface upon which the patient is positioned. Operation 504 may also include establishing a reference plane for the mesh. Referring to FIG. 18, a scan 600 (e.g., mesh) of an example patient is shown from the left and right sides of the patient, according to an embodiment. As shown, the mesh includes an array of points defining a body surface of the patient. Operation 504 may include identifying a ground plane 604 (e.g., ground surface, floor, etc.) of the mesh to orient the mesh and simulate the actual orientation of the patient relative to the ground plane 604. The ground plane 604 may be an anatomical plane (e.g., a transverse anatomical plane, a horizontal anatomical plane, etc.) that transects the body or that extends through a lowest or highest point along the volumetric mesh. For example, as shown in FIG. 18, the ground plane 604 may be a reference plane approximating the ground that supports the patient while standing. In some embodiments, operation 504 may include determining and/or generating the ground plane 604 based on a Y-axis coordinate direction of the volumetric mesh (e.g., from a geometry definition file, etc.), by creating a reference plane that extends perpendicular to the Y-axis, through both feet, and through a lowest vertex of at least one of the left foot or right foot.

Operation 504 may include generating or otherwise determining spatial coordinates of the volumetric mesh. For example, the assess module 214 may be configured to generate a Z-axis 610 having a positive axis direction that is oriented away from a front of the volumetric mesh (e.g., so that the Z-axis 610 points toward where a camera was positioned for imaging the patient). Operation 504 may further include generating a Y-axis 612 that is perpendicular to the Z-axis 610 and having a positive axis direction that is oriented upward from the ground plane 604 toward the patient's head. Operation 504 may further include generating an X-axis 614 that extends from left-to-right with respect to the patient and having a positive axis direction that is oriented laterally out of the page as shown in FIG. 18. It should be appreciated that in some embodiments, the coordinate system and/or ground plane may be established as part of data capture operations performed by the scan module 212 (FIG. 2) instead of, or in combination with, the assess module 214, and may be determined based on spatial coordinates used in a geometry data file that represents or defines the volumetric mesh.

Operation 504 may include determining, by the assess module 214 a reference geometry for the volumetric mesh (e.g., the geometric mesh representation of the patient, etc.) from which measurements may be taken and compared with healthy and/or neutral values of patient posture or form. In the example embodiment of FIG. 18, operation 506 includes computing and/or generating a plumb line 606 that extends in a substantially perpendicular orientation relative to the ground plane 604 and centering the plumb line 606 on a landmark corresponding to a position of the patient's lateral malleolus 608. In other embodiments, operation 504 may include calculating and/or generating other reference lines or surfaces based on previously calculated features (e.g., the ground plane 604, the plumb line 606, etc.). For example, operation 504 may include calculating a reference line that extends through at least a portion of the patient's spine (e.g., through landmarks corresponding with the location of vertebrae, etc.). In some embodiments, operation 506 further includes generating references lines and/or surfaces that correspond with healthy and/or neutral values of patient posture or form. The healthy and/or neutral values may be stored in memory 208 and may be based on empirical data (e.g., average characteristics across multiple patients) and/or values recommended by professionals in the MSK field.

Figure 20:
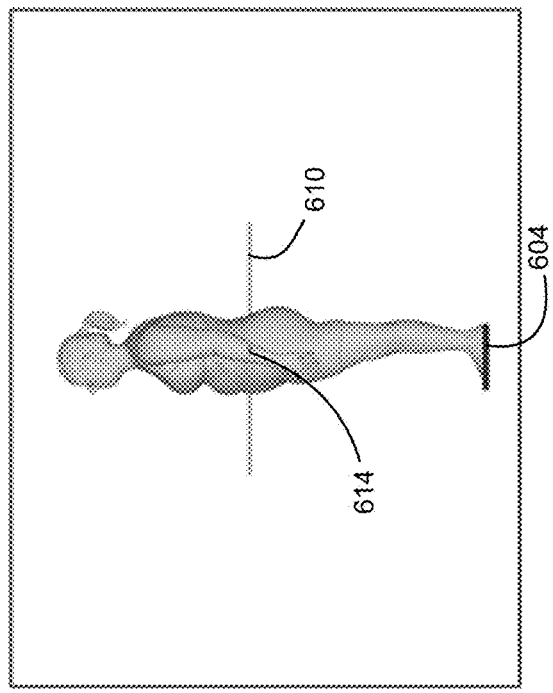
FIG. 20 is a side view of the 3D mesh of FIG. 19.
Figure 19:
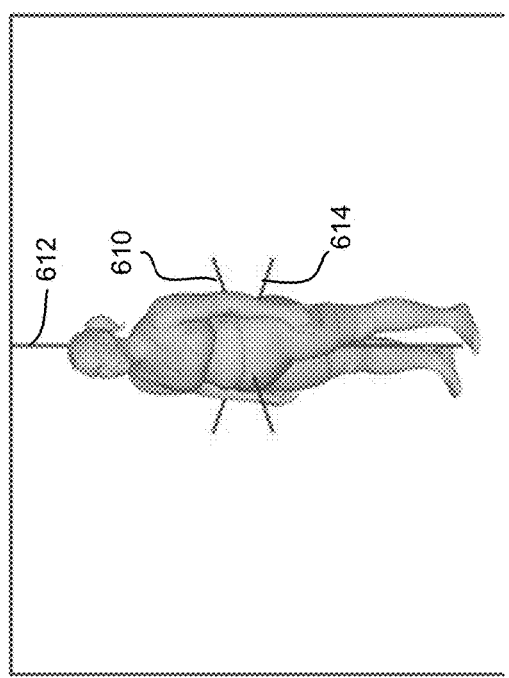
FIG. 19 is a perspective view of a 3D mesh of a human body, according to another embodiment.

In at least one embodiment, operation 504 includes identifying reference geometry (e.g., points, areas, geometric parameters, etc.) along or within the volumetric mesh. For example, operation 504 may include applying numerical integration algorithms to the volumetric mesh to identify a center of volume of the entire mesh and/or selected parts of the mesh. The center of volume may correspond with a three-dimensional centroid of the mesh. Referring to FIGS. 19 and 20, a perspective and side view, respectively of another volumetric mesh of a patient is shown, according to an embodiment. Operation 504 may include determining a center of volume for the entire body from the volumetric mesh, for the feet and/or for the upper and lower parts of the body. Determining the center of volume for feet may include determining, using numerical integration over a volume of the mesh, such as a mesh slicing algorithm (e.g., contour approximation, etc.) the center of volume (e.g., the centroid) of a portion of the mesh that extends upwardly from the ground plane within a range between approximately 1 and 3 cm from the ground plane (e.g., within a range between approximately 1.5 and 2.5 cm from the ground plane, approximately 2 cm from the ground plane of the geometric mesh representation, etc.). For example, determining the center of volume for the patient's feet may include applying a numerical integration algorithm to identify a center of volume of an approximately 2 cm slice of the volumetric mesh at the bottom of the mesh. Operation 504 may include performing integration over faces of the mesh, and averaging the centers of volume of the corresponding 3D simplexes and summing these components, with positive or negative signs determined based on an orientation of each face.

Determining a center of volume of the upper and lower half of the body may further include determining a separation point 614 (e.g., a second reference geometry, etc.) between the upper and lower part (e.g., portion, etc.) of the patient's body. In at least one embodiment, the system determines the separation point based on an average height of a person's belly button as a fraction of an overall height of the mesh (e.g., as measured from the ground plane) for multiple patients (e.g., from a reference set of patient data) and averaging the data.

Figure 21:
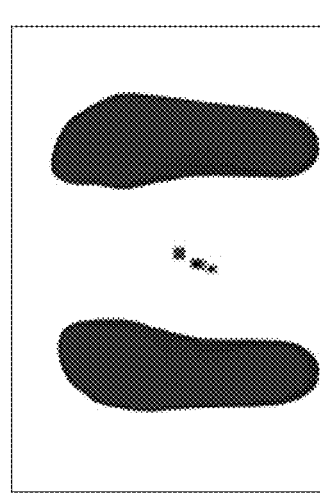
FIG. 21 is a bottom view of a ground plane of a 3D mesh, according to an embodiment.

Operation 504 may further include projecting the center of volume of the entire body, feet, and/or lower and upper parts of the body along the vertical (e.g., Y-axis 612) direction onto the ground plane 604 to facilitate further calculations. For example, FIG. 21 shows a bottom view of the ground plane 604 (see also FIG. 20) at which points corresponding with the center of volume of the entire body, feet, and upper and lower body halves are projected onto the ground plane 604.

At 506, the assess module 214 determines a landmark (e.g., a second reference geometry, etc.) corresponding to one of skeletal or soft tissue anatomy for the patient. As used herein, "landmark" refers to an actual geometry of the volumetric mesh such as a position of a joint, vertebrae, muscle group, etc. In some embodiments, the landmark corresponds to a center of volume of a body area or zone, and may be calculated in a similar manner as described above with respect to operation 504 (e.g., the reference geometry may itself be a landmark).

For example, the landmark may be or include a center of volume of a first body portion of the volumetric mesh (e.g., the geometric mesh representation, etc.) and the reference geometry may be or include a center of volume of a second body portion of the volumetric mesh. In such instances, determining the postural deviation (e.g., at 508) may include projecting (e.g., by a processor, by the assess module 214, etc.) the center of volume of the first body portion and the center of volume of the second body portion onto a ground plane of the spatial coordinates, and determining a shortest distance between the projections.

In other embodiments, the landmark is determined based on statistical analysis of data from the reference set, as will be further described below with respect to various biometric screens and assessments.

At 508, the assess module 214 determines a deviation between landmark geometry in the mesh and the reference geometry. In the embodiment shown in FIG. 21, operation 508 may include determining a balance of the patient's body (e.g., a level of balance, etc.) by comparing ground plane projections of the center of volume for different body areas to a reference set of patient data. The reference set of patient data may be obtained based on measurements of multiple patients and/or healthy values as defined by medical experts (e.g., baseline values indicating healthy balance, nominal values, etc.). For example, operation 508 may include calculating pairwise distances (e.g., along the X-axis 614 and Z-axis 610) between the ground plane projections and determining deviations in balance by comparing the distances with averages established from the reference set or by medical experts.

As used herein, "reference set" refers to a collection of data obtained through analysis of multiple patients. The reference set may include measurement data from different body areas. The system may be configured to use averages from these measurements to identify certain body areas or points along the volumetric mesh that correspond with certain body features. The system may also be configured to determine and use other statistical parameters from data in the reference set, such as a standard deviation of certain measurements.

In some embodiments, operation 508 may include determining a "healthy range" for a measured parameter using data from the reference set. For example, the reference set may include data points corresponding to measured values from 100 patients. Operation 508 may include determining the "healthy range" for the measured parameter by removing a threshold percentage of outliers on each end the reference set (with the remaining measurements being within the "healthy range"). For example, operation 508 may include determining a healthy range of pairwise distances between the ground plane projections by eliminating the outermost 5%, 10%, 15%, etc. of measured values from a reference set. Operation 508 may include classifying the measured values as being healthy, low risk, or high risk depending on deviations from nominal ranges.

In some embodiments, the method 500 may include determining a center of volume of other fragments, portions, and/or areas of the patient's body to facilitate determination of other properties and/or measurements. For example, operation 508 may include identifying vertical stacking and/or vertical loading of the patient's body by determining the center of volume of horizontal slices along the volumetric mesh (e.g., a series of landmarks along the Y-axis direction, etc.). In such instances, operation 506 may include determining (e.g., generating, etc.) horizontal sections (e.g., 2D outlines, surfaces, faces, etc.) from the geometric mesh representation. For example, operation 506 may include determining a first horizontal section (e.g., 2D section, surface, etc.) at a first position of the geometric mesh representation along a first coordinate axis of the spatial coordinates of the mesh, and a second horizontal section of the geometric mesh representation at a second position along the first coordinate axis. In at least one embodiment, operation 506 includes executing a call function from the 3D mesh manipulation library to manipulate and/or re-render the volumetric mesh to include the horizontal section. For example, operation 506 may include executing a mesh slice call function to automatically identify all faces of the mesh at a desired Y-axis position that intersect with an XZ plane, and to generate the horizontal section based on the intersections (where each face-intersection is an interval or edge along the horizontal section). Operation 506 may further include determining and/or generating a horizontal slice of the mesh (e.g., a 3D volumetric section, etc.) bounded by the first and second horizontal sections.

Operation 506 may include determining the center of volume at horizontal slices corresponding to, or centered about, key joints (e.g., ankle, knee, hip, shoulder, ear, etc.) of the patient's body (e.g., at locations determined based on statistical averages of the location of key joints from the reference set, etc.).

In other embodiments, operation 506 may include discretizing the mesh by determining and/or generating horizontal sections in approximately equal intervals (e.g., with a resolution of approximately 0.5 cm, 1 cm, 2 cm, etc.) across an entire height of the mesh, between the ground plane and a largest Y-axis data point of the geometric mesh representation by: (i) identifying all faces of the mesh at each height; (ii) determining the intersection of each face with a reference plane oriented perpendicular to the y-axis at that height. Each horizontal slice is a volume disposed between adjacent horizontal sections (e.g., with a height equal to the spacing between sections).

Figure 22:
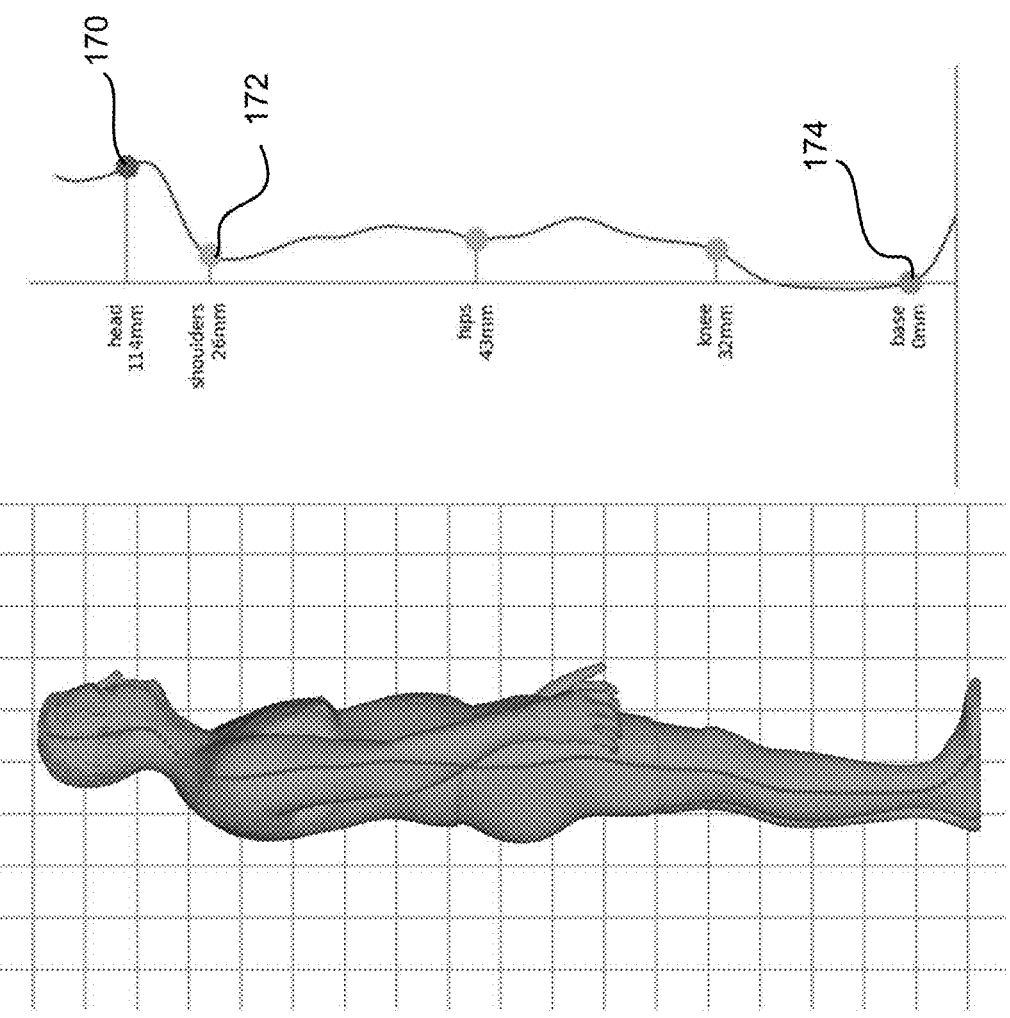

Operation 508 may include projecting these centers of volume onto the YZ-plane (as shown in FIG. 22) that passes through the center of each joint to generate a 2D vertical load line extending along the YZ-plane. In some embodiments, operation 506 may include cross-sectioning the volumetric mesh at multiple heights along the mesh and calculating the two-dimensional geometric center of at each section to generate a line showing a tilt of the body as shown in FIG. 22.

Operation 508 may include determining the distances of the projections (e.g., horizontal distances along the Y-axis direction, etc.) from a vertical line (e.g., a plumb line) going through the ankle as shown in FIG. 22 and comparing the values to averages from the reference set. In some embodiments, the assess module 214 centers the reference line on the lateral malleolus and extends the reference line vertically with respect to the coordinate system for the 3D mesh (with respect to the ground plane). Next, the assess module 214 determines the horizontal distance (left-to-right in FIG. 22) between various points along the 2D vertical load line (e.g., between each one of the plurality of landmarks) and the reference line. The assess module 214 then identifies, from these horizontal distances, which section of the vertical load has the greatest deviation from nominal values (or which section has the largest deviation relative to other sections of the body).

At 510, the assess module 214 displays, by a display of the device, a graphical user interface indicating a characteristic related to the postural deviation. The characteristic may be an amount of postural deviation (e.g., a measured deviation from healthy and/or neutral values of patient posture, etc.), a vulnerability level of a patient to injury in at least one body area that is associated with the postural deviation, or another score or metric that is associated with the postural deviation. In at least one embodiment, operation 510 includes classifying the postural deviation with a risk value based on a comparison between the postural deviation and a healthy and/or neutral range (e.g., a linear alignment, an average value of alignment determined based on the reference set of patient data, etc.). For example, the assess module 214 may be configured to assign a low risk value (e.g., a score of 0, 1, etc.) to a postural deviation based on a determination that postural deviation satisfies the healthy and/or neutral range (e.g., that the postural deviation lies within the healthy range, is below a threshold level for the healthy range, etc.).

The assess module 214 may be configured to display a graphical user interface indicating the characteristic. For example, the assess module 214 may be configured to generate a display screen (e.g., via the display of the user interface) to notify the user and/or clinician of areas that fall within or outside of averages from the reference set or healthy values (or where the body area lies a significant distance away from the vertical line). For example, as shown in FIG. 22, the system may be configured to generate a display screen that shows measurement values of postural deviation from various body areas. FIG. 22 shows measurement values between the vertical line and mesh locations corresponding to the head, shoulders, hips, knee, and base. The display screen shows a point at each body area that is colored to identify relative deviations between the measured value and average or healthy values. For example, the display screen shows a first data point 170 at the head having a red color to identify that the measured distance between the vertical line and the center of volume of the user's head is well outside of average or healthy values. The display screen also includes a second data point 172 at the shoulders having a yellow color to indicate values that are within a range of concern (e.g., just outside of average values or where improvement is needed). The display screen also includes a third data point 174 at the base of the user in green indicating that the measure value falls within the average or lies along the vertical line.

Figure 23:
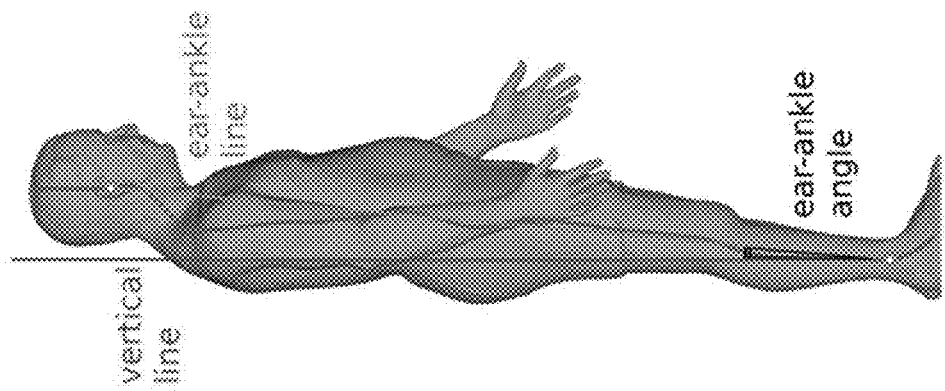
FIGS. 22-25 are display screens for a method of computing vertical load from scan data of a human body, according to at least one embodiment.
Figures 24, 25:
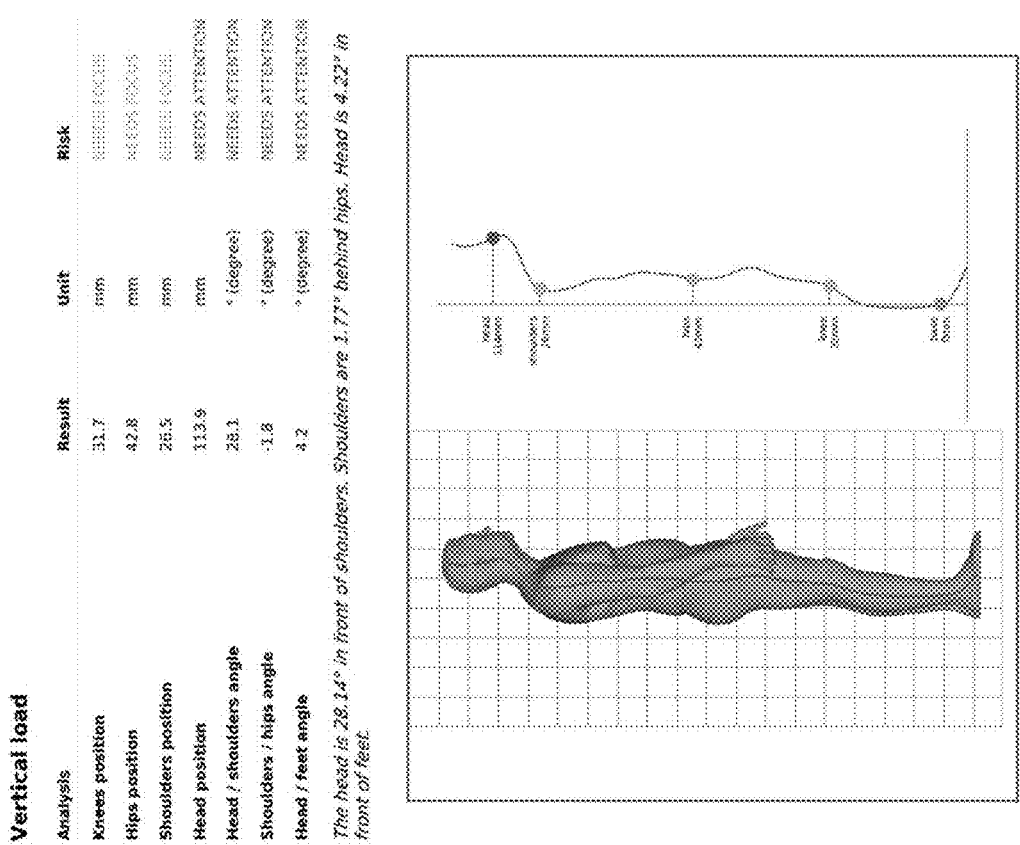

The method of displaying the characteristic may be different in other embodiments. For example, operation 508 may further include determining the angles between the vertical line and reference lines connecting the (projections of) centers of volume for the ankle and the various joints. For example, FIG. 23 shows a head-to ankle angle determined between the vertical line through the patient's ankle and an ear-ankle line that extends linearly between the ankle and the patient's ear. Operation 510 may include determining a health level of the patient (with respect to vertical loading) by comparing the calculated angles to averages and/or a range of values representing healthy bodies from the reference set, generating a visual representation and/or indication of the health level, and overlaying the health level and measurements on a graphical representation of the patient (e.g., on the mesh as shown in FIG. 24). Operation 508 may further include repeating a similar sectioning and center of volume comparison between the right and left sides of the geometric mesh representation (e.g., split along the center of volume of the mesh, etc.). Operation 508 may include determining a difference between the center of volume of the right and left sides to approximate rotation of the patient's body in a neutral pose, as shown in FIG. 25. Beneficially, the software is configured to determine—via vertical load screen shown in FIGS. 22-25—the vertical stacking of the body from the foot up to the head and the integrity of the kinetic chain of the patient while working against gravity.

Operation 510 may further include tabulating the data, transmitting the data to a user device, and presenting the data via the GUI for analysis by a user and/or clinician. The data may be presented through the GUI using a variety of different formats. For example, FIGS. 22-25 show side views of the 3D model with data points overlaid directly onto the model for further review. The GUI may overlay dialog boxes onto the model to provide relevant information to the user including, for example, measurement details (e.g., landmarks corresponding to the end points of the measurement, origin information for the reference geometry, etc.), measurement values, calculated differentials, and/or deviations. The user may interact with the GUI to obtain additional information about the measurements. For example, the user may select the reference geometry, landmarks, or measurement lines, which may cause additional information to be displayed via pop-ups or dialog boxes overlaid onto the 3D mesh.

In some embodiments, the assess module 214 also provide a summary of the measurement and calculation details in tabular form for user review. The assess module 214 may overlay color-coded indicators onto the table to facilitate quick identification of problem areas that are outside of threshold values. The table may also include a summary row and/or column that may provide a general overview of the biometric assessment results (e.g., what the calculated differentials correspond with) and/or details about how the results compare to nominal values for a healthy individual. The assess module 214 may also be configured to generate a guide table that provides additional detail about relevant landmarks for the analysis, which values are measured from the landmarks, how the calculation is performed, and the acceptable and unacceptable ranges for the calculated differential, as described above.

Figure 26:
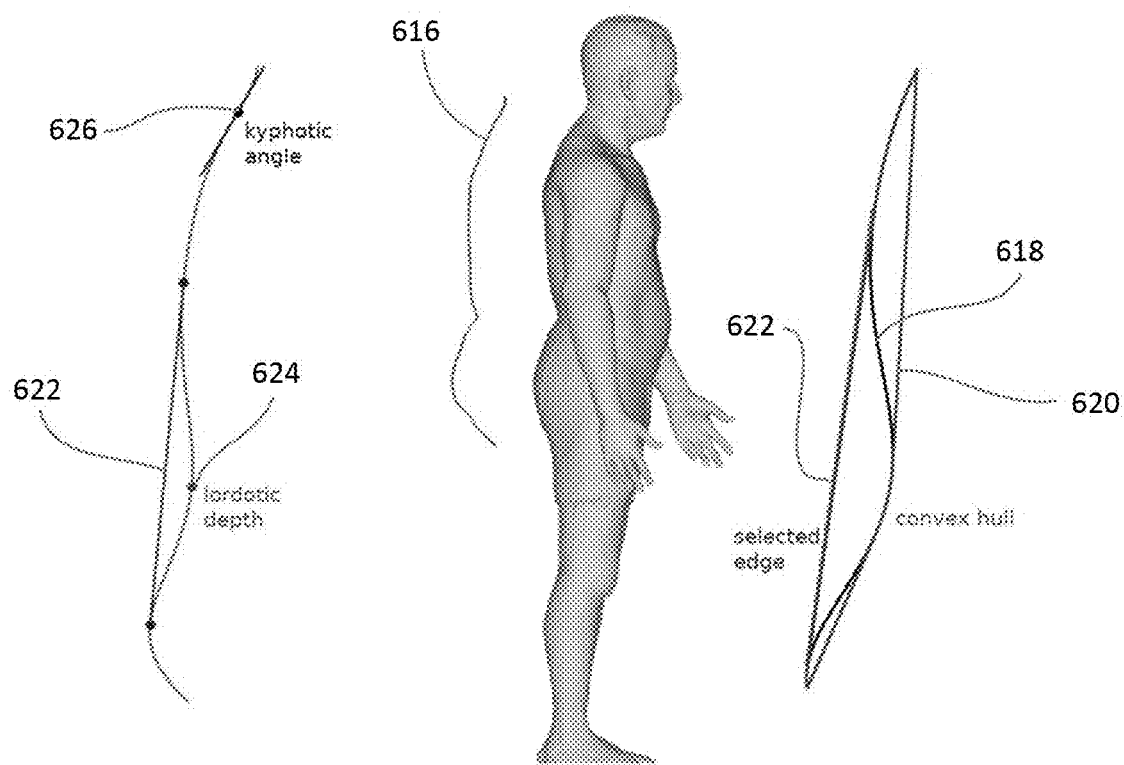
FIGS. 26-27 are display screens for a method of determining spinal mapping from scan data of a human body, according to at least one embodiment.

The software may be configured to perform similar operations to analyze other body areas and/or properties of the volumetric mesh. For example, referring to FIG. 26, the assess module 214 may also be configured to determine a spinal mapping (e.g., to map a patient's spine) by analyzing data from the volumetric mesh. The method may include identifying a fragment of the mesh between the neck and the crotch (e.g., a highest point of the spine along the y-axis and a lowest point of the spine along the Y-axis). For example, the assess module 214 may identify the crotch by traversing the volumetric mesh bottom-up (e.g., starting at the ground plane) and analyzing adjacent cross-sections to identify a point at which the cross-sections change from two distinct shapes (e.g., corresponding to a patient's legs) into one shape (e.g., corresponding to a patient's torso). The assess module 214 may be configured to determine a height of the neck (e.g., C7 vertebrae) based on average values from the reference set (e.g., based on a fraction of a total body height at which the C7 vertebrae is typically located). The method may further include generating horizontal sections (or slices) through the identified fragment of the mesh. The assess module 214 may generate any number of horizontal sections depending on a desired calculation accuracy (e.g., greater than or equal to: 150 slices, 200 slices, 250 slices, etc.). The method may further include determining a position of the patient's spinal canal by analyzing each of the horizontal sections. For example, the assess module 214 may analyze the two-dimensional shape of each section to locate a concave point on that shape near the center of the patient's back (e.g., by traversing vertices of the horizontal section in a defined order to identify local extrema along the Z-axis direction and/or via linear interpolation between points in the mapping).

The method of mapping the spine may further include connecting adjacent concave points with a line, shown as mesh line 616 and smoothing the line defined by the points (e.g., via spline fit or another suitable algorithm). The method may additionally include projecting the smoothed points along the transverse axis of the body (e.g., the X-axis) on a 2D plane (e.g., the XY plane). The method may also include interpolating the projected points by a polynomial function, shown as polynomial line 618, or another suitable curve fit.

The method of mapping the patient's spine may additionally include determining the lordotic depth by identifying a largest distance of the polynomial from a line tangential to the polynomial in the thoracic and pelvic segments. For example, determining the lordotic depth may include determining a convex hull, shown as convex line 620 in FIG. 26, that extends around the polynomial representing the spine, and traversing the vertices $V_1, V_2, \ldots V_p$ of the hull starting at the bottom of the hull and proceeding in a clockwise direction (from the view shown in FIG. 26). The method includes identifying a longest edge, shown as longest edge line 622, connecting the vertices. The method further includes locating a point, shown as lordotic depth point 624 of the polynomial with the largest distance from longest edge line 622, and determining the lordotic depth based on a distance between lordotic depth point 624 and longest edge line 622.

The method may further include determining a kyphotic angle by locating a point along the polynomial with the largest slope in the fragment representing the cervical spine. For example, the method may include determining a first derivative of the polynomial to determine the point of largest slope, shown as kyphotic point 626, along the polynomial in the fragment representing the cervical spine. The method may include determining the relative deviations corresponding with the spinal mapping by comparing the lordotic depth and the kyphotic angle with average values and/or a range of healthy values identified from the reference set.

Figure 27:
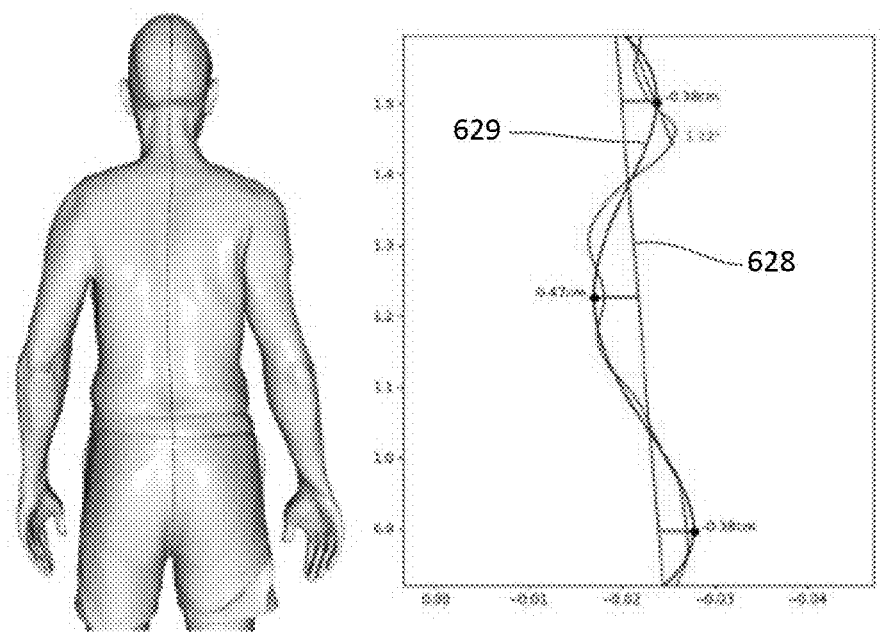

In some embodiments, the method also includes performing a scoliosis analysis to determine deviations between extremes of the polynomial approximation from the spinal mapping from a straight line 628 (e.g., a trend line or reference line determined via linear interpolation of the spine) extending through leading and trailing ends of a polynomial line 629 that approximates the shape of the spine along the XY-plane. For example, as shown in FIG. 27, the method may include calculating a derivative of the polynomial line 629 and determining the distances (e.g., along the X-axis direction) between the straight line 628 and the polynomial line 629 at positions in which the derivative of the polynomial is equal to zero (e.g., by determining a list of points locally most distant from the straight line 628 and displaying an indication of the distances to indicate the shape of the scoliosis).

Figure 28:
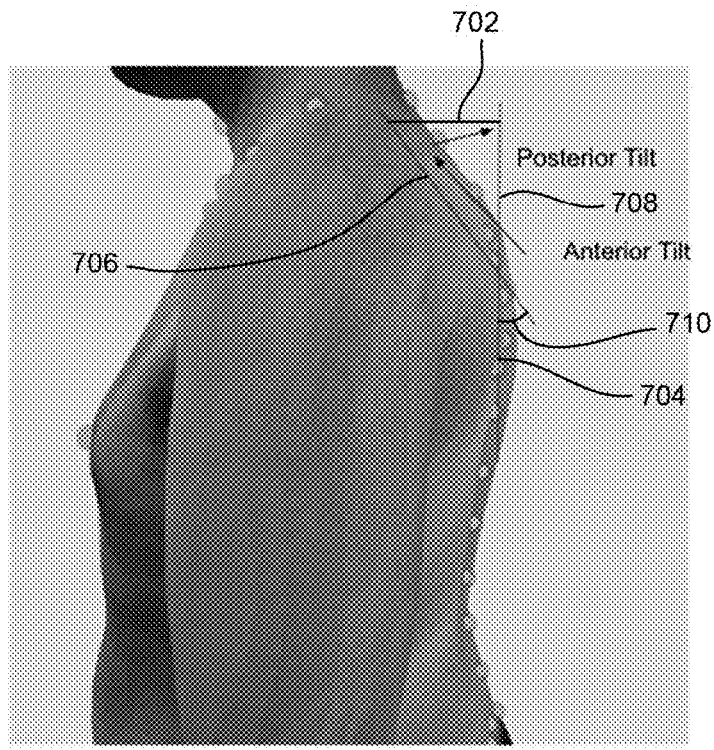
FIGS. 28-31 are display screens for a method of computing scapular tilt from scan data of a human body, according to at least one embodiment.
Figure 29:
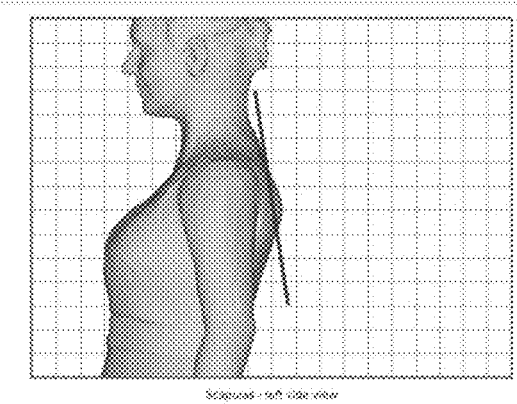

Referring to FIG. 28, a close-up view of the mesh and spinal landmarks (e.g., landmarks indicative of a position of vertebrae along the spine) from the patient data is shown, according to an embodiment. The assess module 214 may be further configured to determine scapular tilt (e.g., scapula angles, etc.) from the mesh and spinal landmarks in FIG. 28 when the patient is positioned at rest. As described above, the assess module 214 may also be configured to determine a straightness of the spine (e.g., mapping the spine), by comparing landmarks for the patient's spine with the plumb line 606 described with reference to FIG. 50, or a line that is substantially parallel to the plumb line 606 and that extends through a rearmost position of the spine. For example, the assess module 214 may be configured to calculate an anterior or posterior tilt of the spine by measuring a horizontal distance 702 between a first reference line 704 and a second reference line 706 at a vertical distance 708 above an intersection between the first reference line 704 and the second reference line 706, and calculating an angle of anterior or posterior tilt of the spine based on the horizontal distance 702 and the vertical distance 708. The software may be configured to generate the first reference line by determining a center position of the scapula, for example, by determining a height of a center of the scapular (e.g., based on a statistical average value from the reference set), and a distance between the center of the scapula and the spine. The software may be configured to measure horizontal and vertical angles around the center of the scapula (e.g., tilt angle 710) by uniformly sampling points from the mesh surface (e.g., defined by the mesh faces) around the center of the scapula, and performing 2D linear interpolation to estimate the surface direction to and determine a scapula plane. The assess module 214 may also be configured to calculate a first postural deviation of the spine and/or scapular tilt by comparing the calculated anterior or posterior tilt with healthy and/or neutral values for an average patient. The software may be configured to repeat these operations for both a left and right scapula of the patient. The software may also be configured to generate and overlay a graphical depiction of the scapula plane onto the mesh, as shown in FIG. 29.

The software may be configured to determine landmarks from the scapular tilt assessment to determine a deviation in scapular position (e.g., shoulder elevation) from a neutral position (e.g., frontal plane measurement from an AC joint or highest part of the traps left shoulder to a corresponding position on the right shoulder relative to a balance or symmetry line that extends substantially horizontally). The software may be configured to determine (1) a proximity of the scapula to the thoracic T7 vertebrae to thereby provide an indication of whether a scapula is in a protracted or retracted position; (2) a distance between the inferior angle/bottom of the scapula to the floor to thereby provide an indication of whether a patient's scapula is elevated or depressed; (3) a positional relationship between the patient's left and right scapula; and (4) an angle of the scapula tilt showing its relationship to body alignment, and positioning of the thoracic spine and the shoulder girdle.

Figure 30:
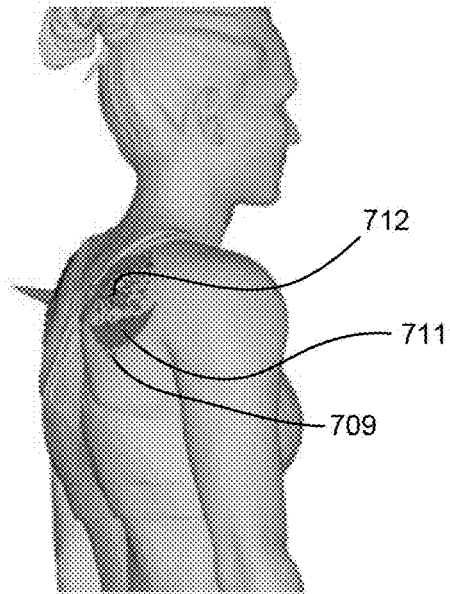
Figure 31:
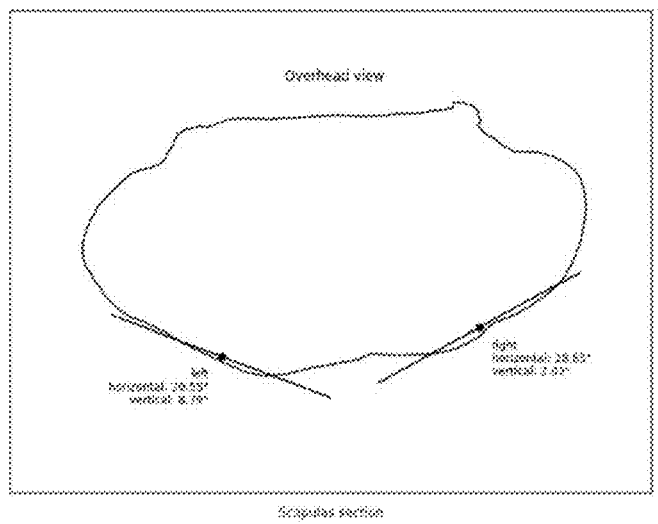

FIGS. 30-31 show another example biometric screen performed by the assess module 214 to determine a deviation in scapular position. The assess module 214 may be configured to identify a position and rotation of the patient's scapula based on the volumetric mesh. For example, the assess module 214 may be configured to identify a direction in which a fragment of the mesh in the area of the scapula is pointing by approximating the fragment with a 2D reference plane. The method may include sampling a surface of the fragment of the mesh and obtaining a set of points from the surface, generating a plane that best fits these points, and calculating a normal vector of the resulting plane. In such an embodiment, the assess module 214 may be configured to identify the fragment of the mesh that represents the scapula body by determining a location of the spine and the shoulder (e.g., the AC joint) as described above (e.g., the scapula body being defined by a portion of the mesh between the spine and the shoulder). The assess module 214 may be configured to sample the surface of the mesh between the spine and the shoulder on each side of the body and to determine the horizontal and vertical rotations of the scapula based on the direction of the calculated normal vector. For example, the assess module 214 may be configured to execute a call function from the 3D mesh manipulation library to determine, and/or re-render the volumetric mesh to include, a set of data points along a surface of the mesh within a threshold range of the fragment or scapular landmark. As shown in FIG. 30, the call function may be a sampling function that randomly generates the set of data points 709, or that generates data points having a normal distribution about the fragment. The assess module 214 may then execute a second call function from the 3D mesh manipulation library to determine and/or generate a reference plane 711 that approximates the set of points (e.g., a scapular orientation plane using a best fit or other statistical approximation). As shown in FIG. 30, the assess module 214 may be configured to determine a normal vector 712 based on the position and/or orientation of the reference plane 711 and may be configured to overlay the normal vector onto the mesh to visually indicate levels of scapular tilt. In other embodiments, the assess module 214 may use a similar method to identify rotation of other parts of the patient's body, such as the patient's hands.

Figure 32:
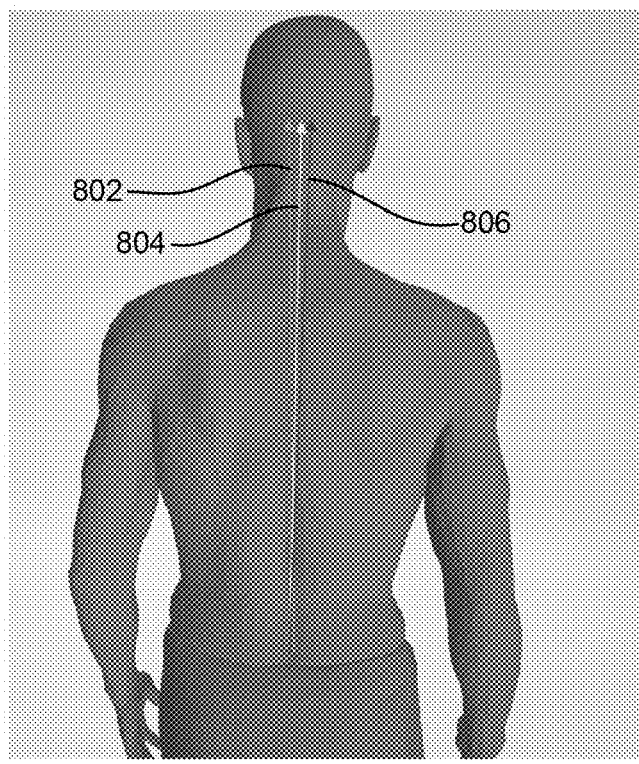
FIGS. 32-33 are display screens for a method of computing spinal mapping from scan data of a human body, according to at least one embodiment.
Figure 33:
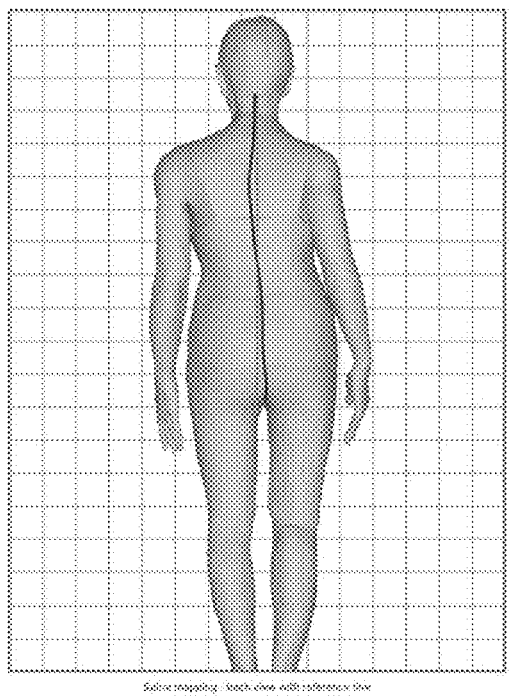
Figure 34:
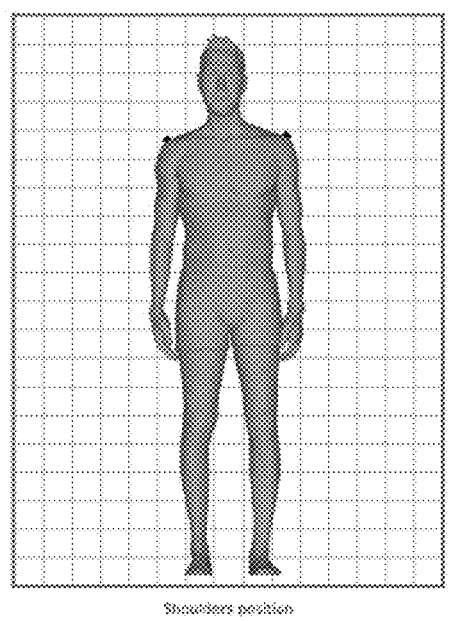
FIG. 34 is a display screen for a method of determining shoulder height, according to at least one embodiment.

FIGS. 32-33 show an example view of a mesh and spinal landmarks that can be used to determine an alignment of the spine along the sagittal plane between left and right sides of the body. The software may be configured to generate reference lines corresponding with a location of the sagittal plane 802, a moderate deviation 804 from the sagittal plane 802, and an extreme deviation 806 from the sagittal plane 802 based on measurements from the spinal mapping assessment (e.g., which can be performed in a similar manner as described above with respect to the spinal mapping in FIGS. 22-25). For example, the as shown in FIG. 32, the software may be configured to generate reference lines indicating that a patient's upper thoracic spine and cervical spine is offset from the sagittal plane 802 and has lateral flexion toward the right side of the figure based on the spinal mapping measurements. A line passing through landmarks corresponding with the patient's spine (e.g., occipital bone C5 and C7, T7 and T12, and L3 and L5) is oriented several degrees from the sagittal plane 802 (e.g., corresponding with extreme deviation 806 from the sagittal plane 802).

FIG. 33 is a display screen for a method of computing spinal mapping from scan data of a human body along a coronal plane (e.g., along an XY plane as described with respect to the coordinate system in FIG. 18), according to at least one embodiment. The software may be configured to use the spinal mapping assessment to determine alignment of the spinal column from the cervical/head to the coccyx at the patient's tailbone. The software may also be configured to use the spinal mapping assessment to determine deviations and/or imbalances that may exist in the spine from the left and right sides of the patient's body. The software can use the spinal mapping assessment, as illustrated in FIG. 32, to determine a stacking of the spine and relative positioning of at least the following landmarks: C1, C7, T7, L1, L3, L5 thoracic, and gluteal notch (top, middle, and bottom) with medical-grade accuracy, which can indicate whether there is functional scoliosis, a true scoliosis, kyphosis, lordosis, sway back, and/or a flat spine that may reduce mobility (e.g., bending over a touching toes, back bending, side bending, and/or rotations). The software may be configured to generate and present a graphical overlay of the spinal mapping relative to reference geometry (e.g., a plumb line, etc.) onto the graphical mesh representation of the patient, along with a summary of measured postural deviations along the spine, in a similar manner as described with respect to FIGS. 24-25.

The assess module 214 may be further configured to identify a position of the patient's shoulder(s) and to determine if one of the shoulders is elevated. For example, the assess module 214 may be configured to analyze a fragment of the mesh that extends upwardly from the ground plane to a position that corresponds with the patient's neck (e.g., the software may be configured to crop or otherwise remove mesh data above a location of a C4 vertebrae as determined based on an average fraction of total body height at which the C4 vertebrae is located in the reference set of patient data). In at least one embodiment, the assess module 214 is configured to automatically determine the approximate location of the patient's neck automatically based on a machine learning algorithm, such as by using patient data from previous scans as a training set for the model. It should be appreciated that, for any of the analyses described herein, any point along the 3D mesh may be automatically identified using a machine learning algorithm, which can improve repeatability and accuracy as compared with manual identification and selection techniques.

In some embodiments, the assess module 214 may determine the approximate location of the patient's neck based on average values from the reference set. For example, the software may determine a reference geometry and/or landmark by identifying the patient's Achilles tendon (e.g., based on an average fraction of a total body height at which the Achilles tendon is located in the reference set). The assess module 214 may then analyze the mesh to determine the most extreme points along a diagonal axes (e.g., an XY-plane along both the positive and negative X-axis directions). For example, the assess module 214 may define a new coordinate system, in which the XY plane is rotated by approximately 45 degrees counterclockwise while maintaining a constant position of the Z-axis, resulting in new axes X' and Y'. The assess module 214 may be configured to identify the shoulders by determining the points of the volumetric mesh with the largest values of the X' and Y' coordinates. The assess module 214 may be configured to diagnose an elevated shoulder by comparing the original Y-axis coordinates of each shoulder to see which is located at the largest position along the Y-axis (e.g., by determining a difference between a height of the reference points corresponding to the left and right shoulders).

Figure 35:
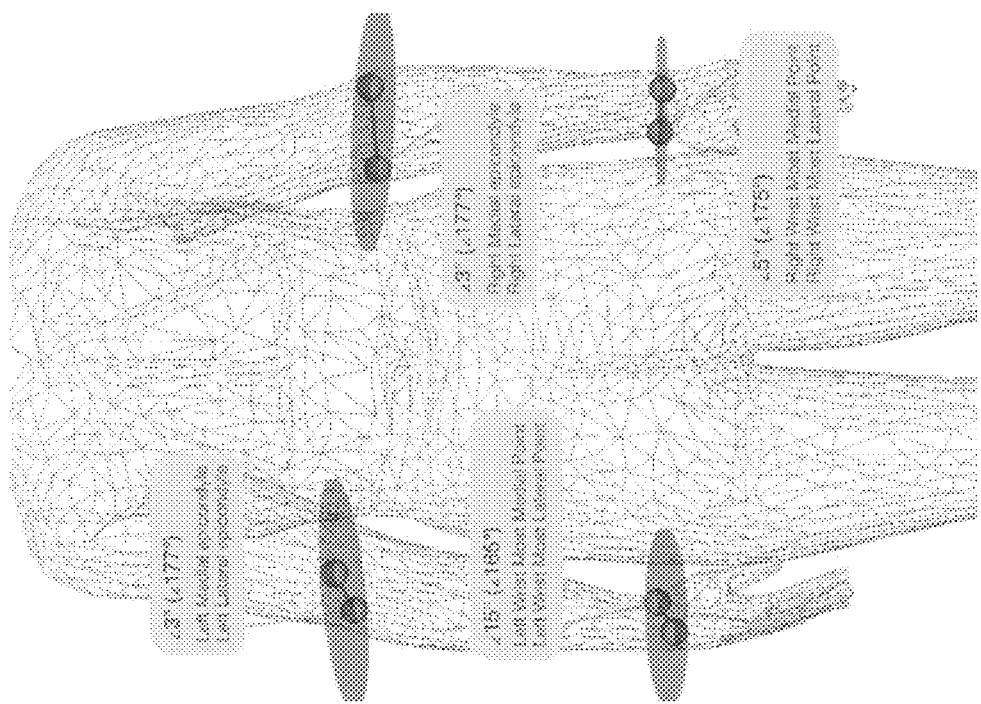
FIG. 35 is a rear view of a 3D model of a human body being used to determine and compare wrist and elbow alignment on both sides of a human body from scan data of the human body, according to an embodiment.

FIG. 35 shows a biometric screen used to evaluate a position of the patient's elbows and/or wrists through all anatomical planes. The biometric screen include generating a reference disc passing through reference geometry along certain body portions (e.g., wrist joint, elbow joint, etc.) to facilitate visualization of tilt and alignment between the patient's left and right sides. This biometric screen may determine the outer and inner angles of a disc that sits between the medial epicondyle and lateral epicondyle landmarks on the 3D model. The biometric screen may also determine outer and inner angles of a disc that sits between the wrist most medial point and the wrist most lateral point for both the patient's arms.

Figures 36, 37:
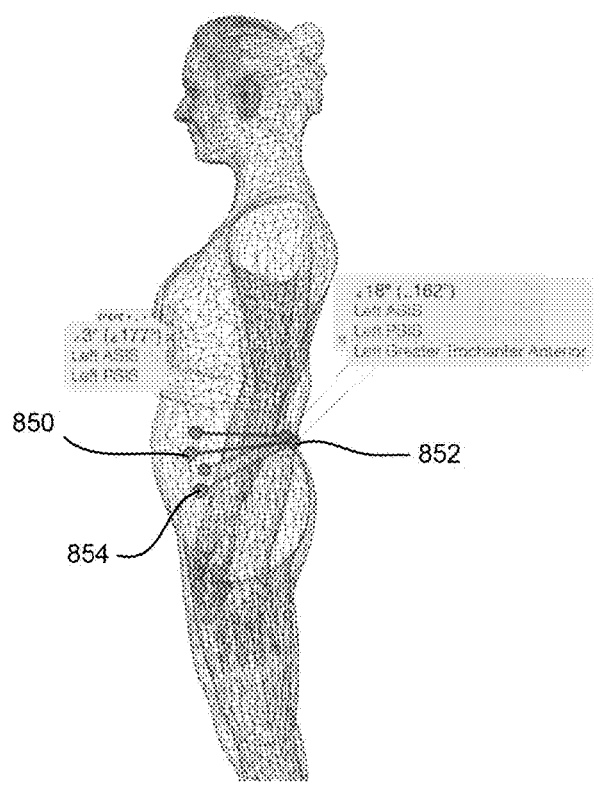
FIG. 36 is a display screen for a method of computing pelvic position and deviation from scan data of a human body, according to at least one embodiment.
FIG. 37 is a display screen showing measured postural deviations based on the pelvic position and deviation scan of FIG. 36, according to at least one embodiment.
Figure 38:
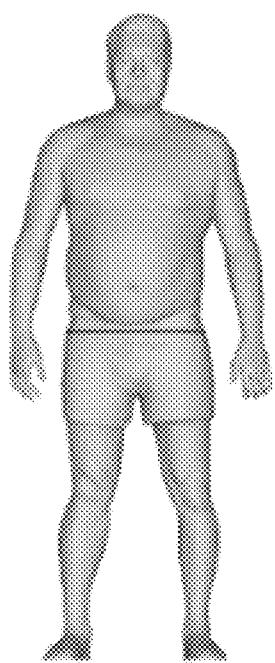
FIGS. 38-41 are display screens for methods of computing body area rotations, according to at least one embodiment.

FIG. 36 shows a biometric screen used to compute pelvic position, angle, and deviation from the 3D model data. The screen may include calculating inner and outer angles between the three points, including: the ASIS 850, the PSIS 852, and the greater trochanter 854 of the femur. The pelvic angle screen may focus on the position of the pelvis front-to-back to indicate the position of the spine as well as the pelvis and spine in relationship to the femur bone. As shown in FIG. 38, the software may be configured to generate a table summarizing the measurements from the pelvic screen, and may include graphical indicators (e.g., color-coded table cells, etc.) to provide a visual indication of postural deviations that exceed threshold values.

FIGS. 38-41 show views of biometric screens used to determine levels of rotation in different body areas (e.g., the hips and rib cage, respectively). The assess module 214 may be configured to identify body rotations by analyzing two-dimensional cross-sections (e.g., horizontal sections, etc.) in different regions along the volumetric mesh. For example, the assess module 214 may be configured to determine a horizontal cross-section along the XZ-plane, and to identify an axis (i.e., a reference line that intersects the cross-section) that has a minimal moment of inertia within the plane. For each section, the software may be configured to determine a number of coherent components and to identify the component with the largest area to ensure that the entire cross-section is considered in the analysis. The assess module 214 may be further configured to determine a rotation of the body area at the cross-section by determining an angle between the axis with minimal moment of inertial and the X-axis of the coordinate system.

Figure 39:
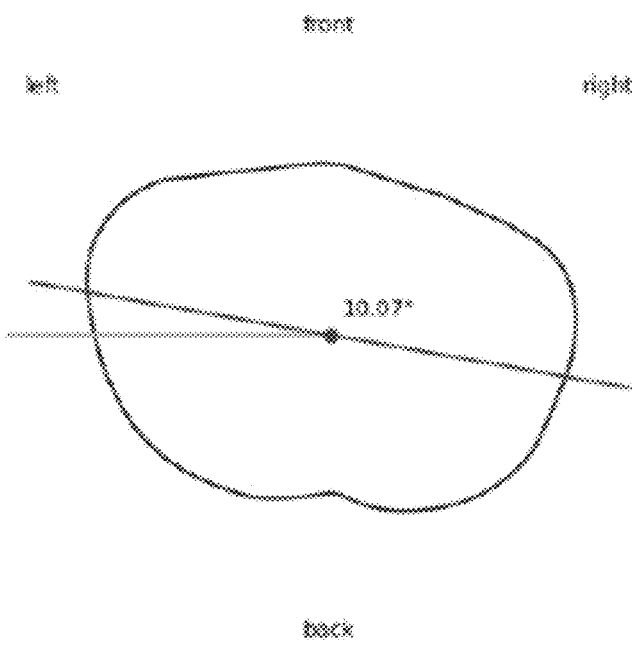

In the embodiment of FIGS. 38-39, the assess module 214 is configured to determine an amount and/or level of hip area rotation. In such an embodiment, the assess module 214 is configured to apply the foregoing method to two separate cross-sections, including a first cross-section at the level of the greater trochanter and a second cross-section at the level of iliac crest (e.g., at heights corresponding to a pelvic level and a femur level, etc.). The assess module 214 may be configured to determine a relative deviation in the measured hip area rotation by comparing the two rotations to average values obtained by applying a similar method/analysis to multiple patients.

Figure 40:
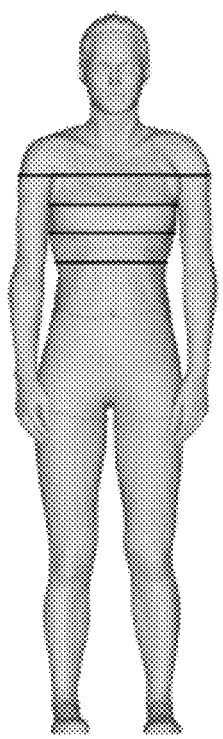
Figure 41:
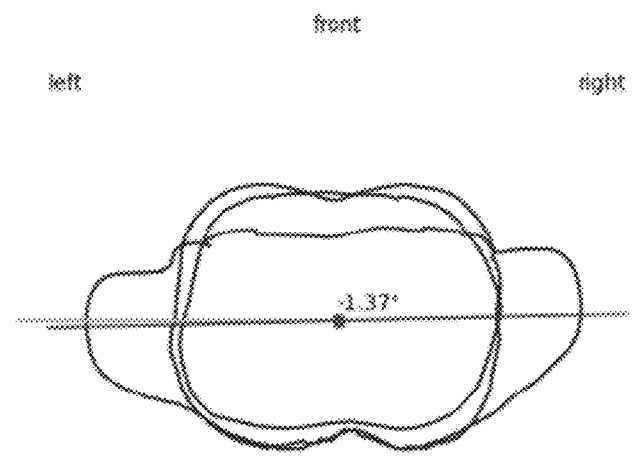

In another embodiment, as shown in FIGS. 40-41, the assess module 214 is configured to determine an amount and/or level of rib cage rotation. In such an embodiment, the assess module 214 is configured to apply the foregoing method to a plurality of cross-sections, which may include, but is not limited to, a first cross-section at the $11^{th}$ rib, a second cross-section at the nipple (e.g., a $6^{th}/7^{th}$ thoracic vertebrae, etc.), a third cross-section at the sternum, and a fourth cross-section at the clavicular notch. The assess module 214 may be configured to determine a relative deviation of the measured rib cage rotation by comparing the four rotations to average values obtained by applying a similar method/analysis to multiple patients.

In another embodiment, a biometric screen for determining pelvic rotation and/or hip elevation includes calculating the outer and inner angles between the right and left lilac crests, as well as the outer and inner angles between the medial malleolus and lateral malleolus on each leg and/or ankle. The screen may also include generating a disc geometry (e.g., reference disc) that conforms to the pelvis and ankles left to right on specific landmarks to show the angle of the pelvis and ankles. The disc(s) also show whether one side of the patient's body is elevated in the frontal and/or coronal anatomical plane. In another embodiment, the biometric screen includes (1) calculating the outer and inner angles between the ASIS and PSIS landmarks on the right and left sides of the patient's body, and (2) generating a disc indicating the calculation by showing a position of the pelvis from front to back in the sagittal anatomical plane of motion. Among other benefits, the disc helps visualize unilaterally whether one side of the spine/pelvis is lordotic, neutral, or posterior tilted. In yet another embodiment, the biometric screen includes calculating the outer and inner angles of discs between the ASIS and PSIS landmarks on the front and back sides of the patient's body. In this instance, the disc may show the position of the pelvis in the frontal and/or coronal anatomical plane to help visualize the tilt of the pelvis from left to right.

Figure 42:
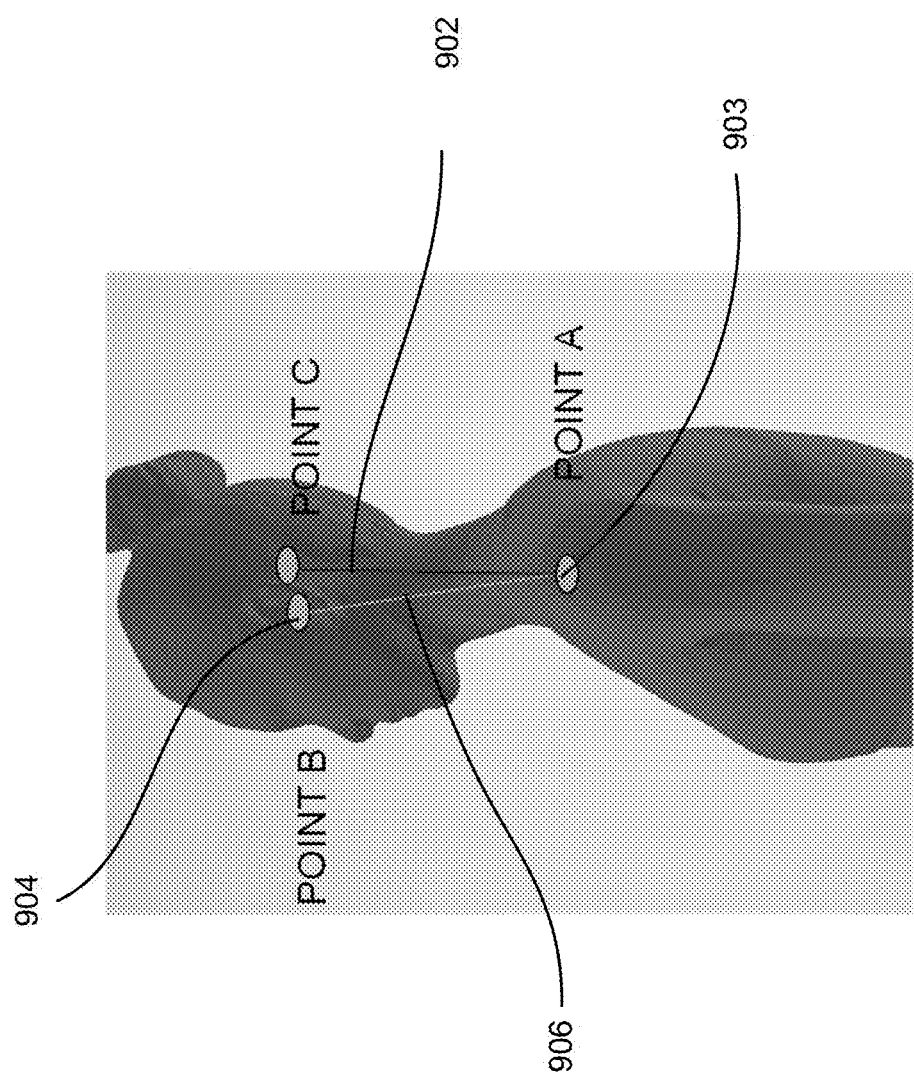
FIG. 42 is a display screen for a method of computing head position and deviation from scan data of a human body, according to at least one embodiment.

FIG. 42 is a display screen for a method of computing head position and deviation from the 3D model data. The head position screen determines the position of the head in relationship to the shoulder, which can help determine how aligned or unaligned someone's head or cervical spine may be. For example, FIG. 42 shows reference lines used to determine a deviation in head posture from the sagittal plane, where a first reference line 902 in FIG. 42 represents healthy and/or neutral alignment between the shoulder AC joint 903 and a patient's ear canal 904, and a second reference line 906 in FIG. 42 represents actual alignment between landmarks corresponding to the patient's AC joint 903 and ear canal 904. The software may also be configured to determine an angle between the first reference line 902 and the second reference line 906 on each side of the mesh, which can provide an indication of overall head position/alignment.

In yet another embodiment, the assess module 214 is configured to determine foot position and an amount and/or level of foot rotation. In such an embodiment, the assess module 214 is configured to apply the foregoing method at a threshold height above the ground plane (e.g., a threshold height corresponding with a central position through the patient's foot, etc.) for each foot. The assess module 214 may be configured to determine a relative deviation of the measured foot rotation by comparing the two rotations to average values obtained by applying a similar method/analysis to multiple patients. The assess module 214 may also be configured to classify the foot rotation (e.g., as one of pigeon toed, duck footed, or neutral) based on the relative deviation and/or known ranges that correspond with different classifications.

Figure 43:
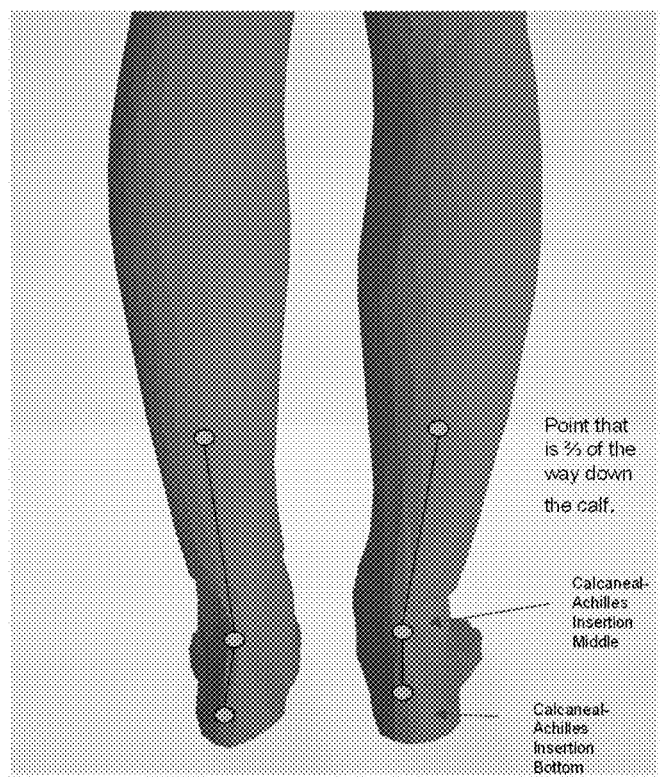
FIGS. 43-44 are display screens for a method of computing foot position and deviation from scan data of a human body, according to at least one embodiment.
Figure 44:
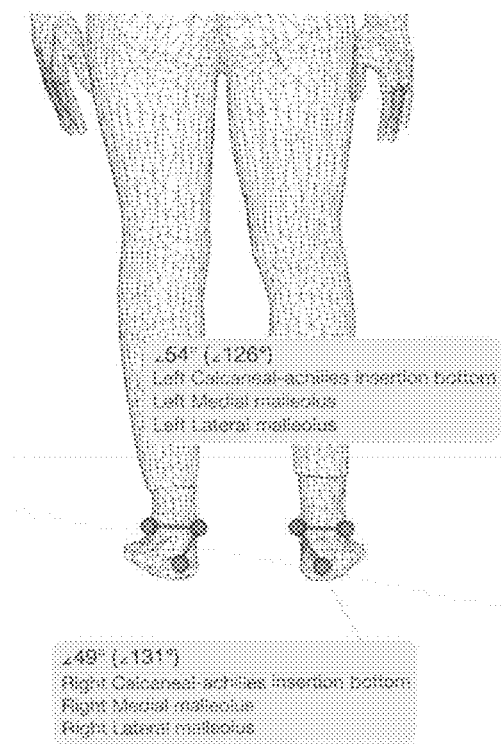

For example, FIGS. 43-44 show a biometric screen for computing foot position and deviation from 3D model data. In one embodiment, the foot position screen may include calculating outer and inner angles between (1) a line from the calcaneal-achilles insertion bottom to the calcaneal-achilles insertion middle; and (2) a line from the calcaneal-achilles insertion middle to a gastroc two thirds of a distance down the calf. This measurement may be repeated for both legs and may provide an indication of the angle of the foot (e.g., to show if an ankle and/or foot is in a pronation, neutral, or supinated position). The software may be configured to perform a similar analysis, using landmark positions, to determine an amount of out-toeing or postural deviation of a patient's stance based on the location of the patient's tibia medial malleolus and big toe joint.

In another embodiment, the foot position screen may include calculating an inner and outer angle between the calcaneal-achilles insertion bottom, medial malleolus, and lateral malleolus points to show if the patient's ankle and/or foot is in a pronation, neutral, or supinated position.

Figure 45:
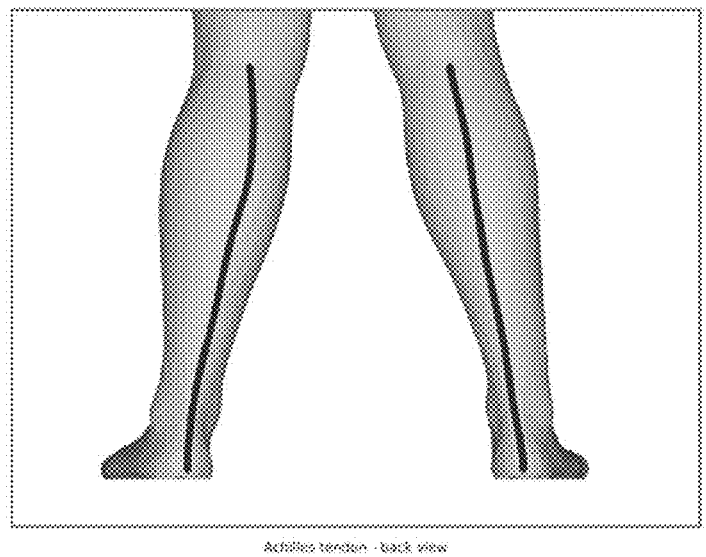
FIG. 45 is a display screen for mapping an Achilles tendon, according to an embodiment.

FIG. 45 illustrates a biometric screen for determining foot pronation and supination, according to another embodiment. The method includes splitting the mesh into left and right side portions, for example, along a YZ-plane at a location corresponding with a global center of volume. The method may further include identifying, via the assess module 214, a location of a center of the foot along a Y-axis direction (e.g., a location of the Achilles tendon). For example, the assess module 214 may be configured to determine a location of the Achilles tendon from the ground plane up to a middle point along the calf based on average values from the reference set (e.g., based on a fraction of a total body height at which the Achilles tendon is typically located). The software may be configured to determine a center of the foot along an XZ-plane. For example, the assess module 215 may be configured to calculate multiple horizontal cross-sections (e.g., horizontal sections) along the XZ-plane taken at approximately equal intervals between the ground plane and the middle point along the calf. In some embodiments, the method includes determining a centroid of the horizontal section at the Achilles tendon and determining an angle of the foot based on an axis of minimal inertia, similar to the method of determining body are rotations as described with reference to FIGS. 38-41. As shown in FIG. 45, the software may be configured to generate a reference line (e.g., a polynomial approximation, etc.) extending along the centroid of each horizontal section and overlay the reference line onto mesh. The software may be configured to determine, based on this information, a rotation of each foot, a distance between centers of each foot, and/or a shift (e.g., a distance along the Z-axis) between centers of each foot.

Figure 46:
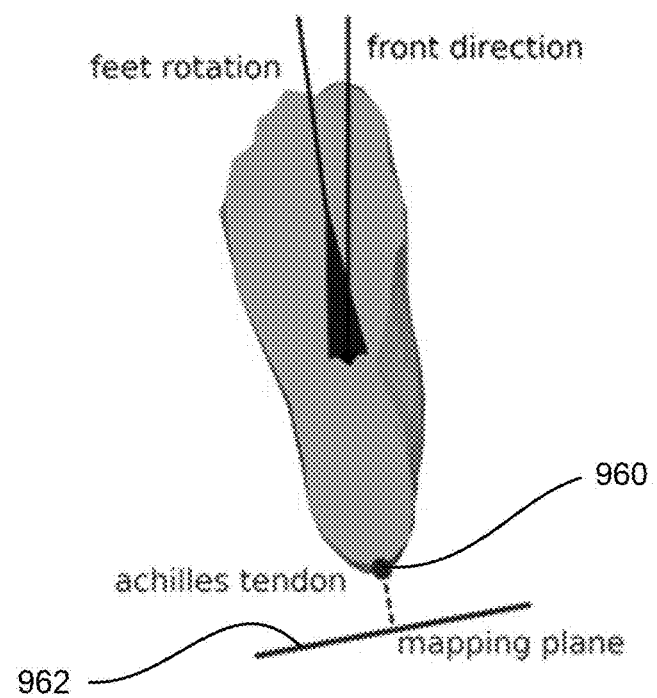
FIG. 46 is a display screen for a method of determining foot pronation and supination, according to an embodiment.

In other embodiments, the method includes identifying a point along each cross-section that is farthest back along the foot direction axis, shown as foot axis 960 in FIG. 46. The method may also include projecting these points on a reference plane, shown as mapping plane 962 that is arranged orthogonal to the foot axis 960. The assess module 215 may be configured to approximate these projections with a polynomial or another suitable curve fit. The assess module 214 may be further configured to determine foot pronation and supination based on the curvature of the polynomial function (e.g., based on the sign and value of the coefficient of the quadratic term of the polynomial function).

Figure 47:
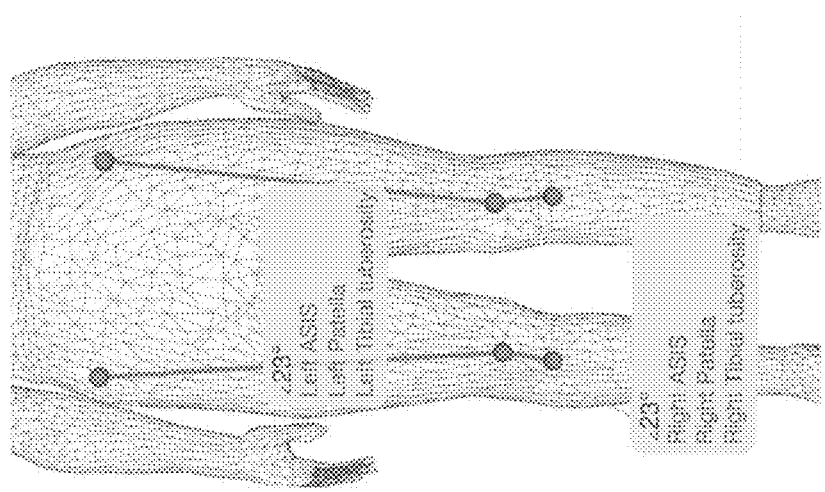
FIG. 47 is a display screen for a method of screening Q angle from scan data of a human body, according to at least one embodiment.

FIG. 47 shows a biometric screen for assessing Q angle from 3D model data from landmarks along the mesh. The Q angle assessment may include determining two angles, one for each leg, using (1) a line from the ASIS to a center of the patella, and (2) a line from the center of the patella to the tibial tuberosity. In the embodiment shown, the Q angle assessment measures the angle of the quadriceps muscle group to show the position of the femur in relationship to the patella and tibia bone. The software may be configured to generate and overlay references lines that are used to determine valgus stress at the patient's knees (e.g., deviations in an angle between the patient's femur and tibia, Q-angle, etc.) onto the mesh.

Figure 48:
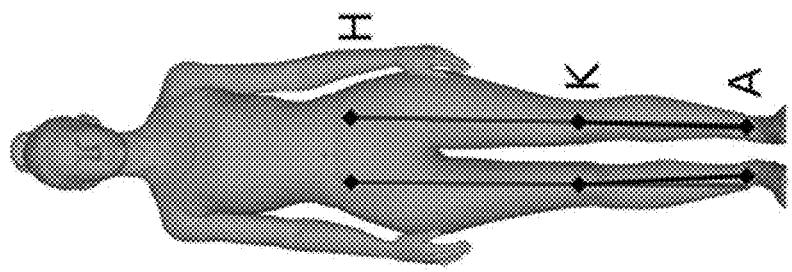
FIG. 48 is a display screen for a method of determining leg curvature, according to at least one embodiment.

FIG. 48 illustrates a biometric screen for determining leg curvature and diagnosing valgus and varus stress. The biometric screen includes identifying, for each leg, three points used for the measurement, including the ankle, the knee, and the head of femur. The assess module 214 may be configured to identify these points based on their statistical heights across multiple patients from the reference set (e.g., based on a fraction of a total body height at which these body features are typically located). The biometric screen includes calculating cross-sections, shown as sections A, K, and H in FIG. 48, of the volumetric mesh at the height of each of the three points. The biometric screen further includes determining the center of volume CA, CK, and CH of each of the cross-sections A, K, and H, respectively, and projecting the centers of volume onto the XZ-plane. The assess module 214 may be configured to determine an angle between the lines defined by the projections CA–CK and CK–CH. The assess module 214 may be further configured to classify the angle as representing valgus/varus stress or normal curvature based on information from the reference set and/or interpretations by medical experts.

Figure 49:
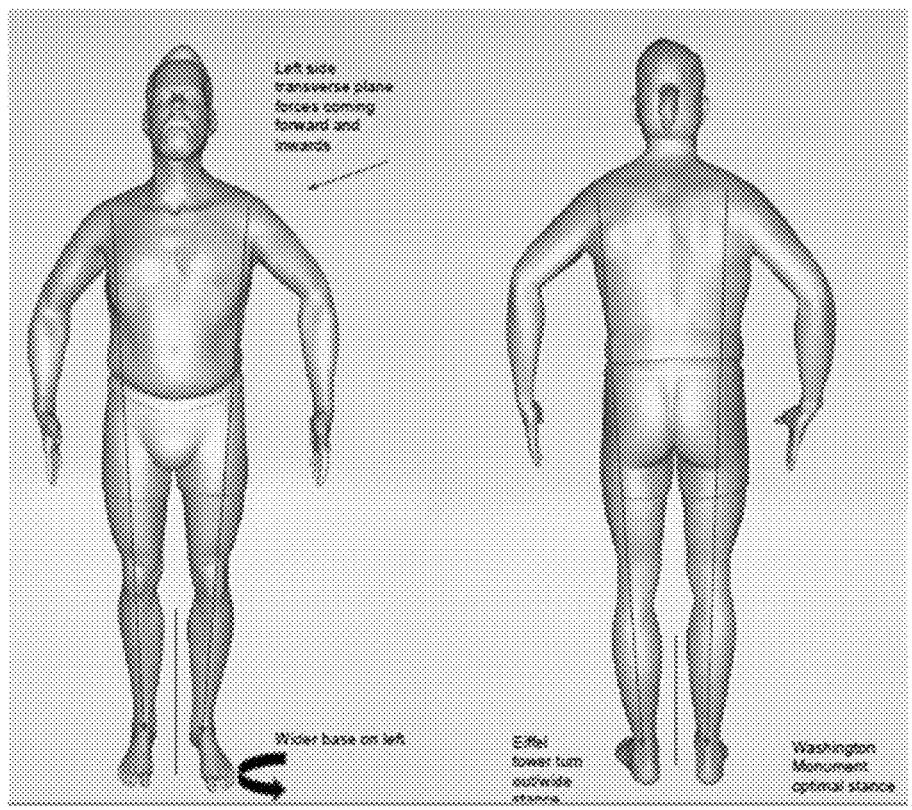
FIG. 49 is a display screen for a method of computing a patient's stance from scan data of a human body, according to at least one embodiment.
Figure 50:
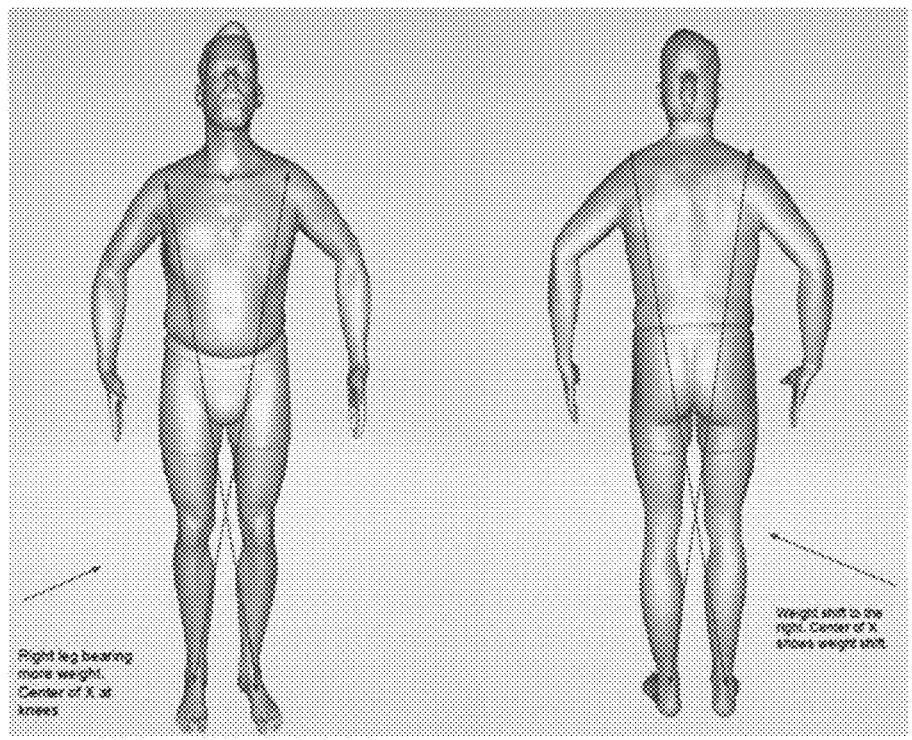
FIG. 50 is a display screen for a method of computing cross pattern postural vectors from scan data of a human body, according to at least one embodiment.

FIGS. 49-50 show biometric screens for computing a patient's stance and cross pattern postural vectors, respectively, from 3D model data, which may facilitate determination of which leg is bearing more weight. FIG. 49 shows reference lines used to evaluate deviations in a patient's stance and FIG. 50 shows reference lines used to evaluate a patient's cross pattern postural vectors. The stance and cross-pattern screens may be used to determine weight distribution between the patient's legs (e.g., an intersection between functional fascial lines extending between the patient's shoulder AC joint and their foot joint show a slight tendency to shift his/her weight to the right).

The software may be configured to generate a table that summarizes the results of various biometric screens performed by the assess module 214 (e.g., any of the biometric screens described above). Among other benefits, the biometric screens described above provide a curated overview of information (e.g., static postural deviations) that helps the patient understand and engage with the static patterns of their body. The biometric screens also provide useful data to the clinician overseeing diagnosis and treatment of the patient.

In addition to the pre-configured operations described above, the system 100 (FIG. 1) may also be configured to allow user interaction with the volumetric mesh and/or pre-configured algorithms via the GUI. For example, the system 100 may be configured to allow a user, via a user interface, to take specify measurements using tools in the GUI, as will be further described, and allow the user to specify their own calculations based on available reference geometry and anatomical landmarks, such as a distance between points in the mesh, angles between any collection of landmarks, and the like. Among other benefits, these mesh-based measurements allow the user to determine circumferences and distances along the body surface in unique areas. A clinician could utilize the measurement features to determine levels and/or amounts of soft tissue swelling in different body areas (e.g., fluid buildup). Various user-defined tracking measurements could be setup that are unique to the patient.

Figure 51:
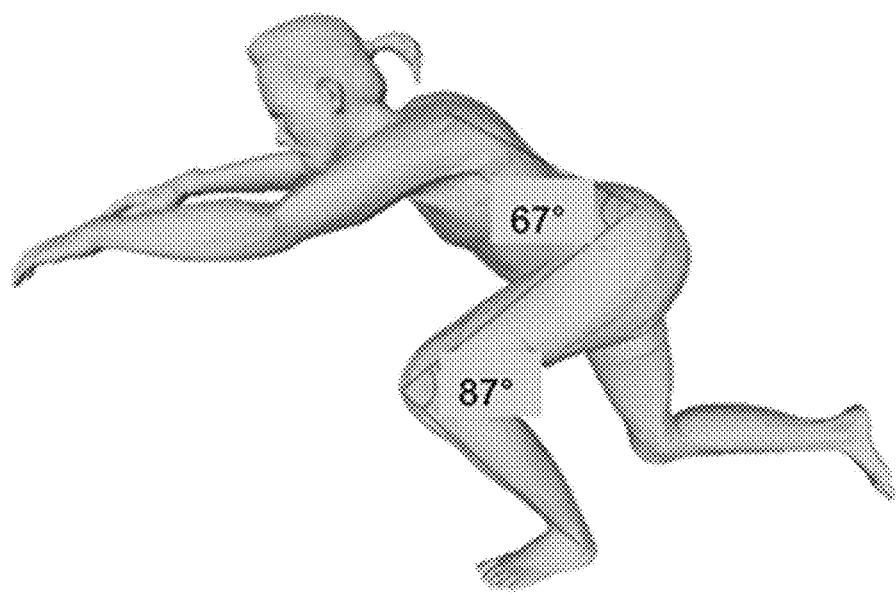
FIG. 51 is a left side view of a 3D mesh of a human body in motion, according to an embodiment.
Figure 52:
FIG. 52 is a front view of a 3D mesh of a human body in motion, according to an embodiment.

Additionally, the system 100 may be configured to generate and assess a moving mesh that corresponds to changes in a patient's body surface and musculoskeletal landmarks while the patient is performing an exercise or movement. For example, FIGS. 51-52 show display screens at a single time instant for a moving mesh, including MSK landmarks (e.g., during a forward lunge—as shown in FIG. 51—and during walking—as shown in FIG. 52). The system 100 may be configured determine changes in landmark position during scanned movements. The system 100 may be configured to map changes in position of the landmarks while performing an exercise and to compare these changes between different patients. Additionally, the system may be configured to output a video of the moving mesh and landmarks to facilitate user analysis. In this way, the system 100 is configured to analyze dynamic patterns of the patient's body, such as a patient's range of motion in various body areas.

Among other benefits, the clinical movement screens provide a level of alignment and automation that cannot be achieved using 2D measurement tools and techniques. The system 100 is configured to identify minutiae in each direction of movement that may be affecting the patient's range of motion (e.g., artificially limiting or extending the range), which is very difficult to detect at the required resolution and accuracy using conventional methods. Moreover, exercises can be prescribed based on the analysis to match specific deviations and patterns of deviations observed during the clinical movement screens and static biometric screens. A clinician (e.g., physical therapist, doctor, etc.) can review the scan and analysis data (e.g., patient health scores, calculated deviations, vulnerability levels, etc.), perform measurements, add notes, and conduct video conferences within the environment of the software application, eliminating the need for in-person assessments.

The system 100 (FIG. 1) may also be configured to perform clinical diagnostic screens that focus on specific areas of performance and/or injury for the patient. For example, the system 100 may be configured to implement algorithms to determine a patient's performance potential in performing specific tasks such as running, jumping, and/or with respect to performance in certain sports activities. The system 100 may also be configured to implement algorithms focused on analyzing physiological issues and injuries such as spinal issues (e.g., scoliosis), lower back pain, osteoarthritis, anterior cruciate ligament (ACL) injuries, tibial slope issues, and others. For example, the system 100 may implement deviation algorithms to identify postural deviations that may be associated with lower back pain such as poor spinal alignment, poor form during movement, and the like. The system 100 may also be configured to identify secondary issues and/or to perform root cause analysis based on the calculated deviations, health scores, and vulnerability levels in multiple body areas. Among other benefits, these clinical diagnostic screens provide the ability to assess large numbers of patients who demonstrate potential for physical therapy or other paid therapies, and to compare results from clinical diagnostic screens in patients with similar issues. The screens also indicate suitability for treatment by a physical therapist and can therefore be used as a low-cost approach for physical therapists to identify potential patients without requiring in-person visits. Additionally, targeted clinical diagnostic screens provide an inducement for individuals to be evaluated who might not otherwise choose to get screened (e.g., due to the ease of remote screening, and the ability of the system to quickly identify issues affecting patient performance in key areas, etc.).

In at least one embodiment, the assess module 214 is configured to generate a GUI that indicates postural deviations to the user (e.g., patient or clinician) and how these deviations compare with healthy and/or neutral values. For example, the GUI may present a visual representation of the mesh with reference lines illustrating the details of each calculation (e.g., similar to any of the 3D models for the biometric screens described above). In another embodiment, the GUI may include geometric indicators that are overlaid onto a visual representation of the patient (e.g., onto the volumetric mesh of the body surface).

The GUI may be configured to present an assessment summary to the user (e.g., patient, clinician, etc.) that includes results from each of the static and dynamic screens. The assessment summary may include a pose identifier (e.g., relaxed pose, etc.) and a listing of analysis results for each measurement type (e.g., scapular position, spinal mapping, vertical load, etc.). The GUI may present visually-perceptible icons for each measurement type that, when selected, redirect the user to a summary page that provides more specific details of the measurement. The assessment summary and/or summary pages may also include color bars, and/or other indicators that present vulnerability levels and/or patient health scores corresponding with the calculated deviations.

In some embodiments, the system 100 (FIG. 1) is configured to determine a health rating and/or score (e.g., a performance rating, a postural rating, etc.) based on the measured structural alignment in various zones of the patient's body. The scores may also take into account reported levels of patient discomfort (e.g., pain) from survey data. The zones may correspond with major joint assemblies in the patient's body, such as the head, shoulders (left and right), the forearms (left and right), cervical spine, thoracic spine and ribs, lumbar spine, hips (left and right), knees (left and right), and the patient's ankles and feet (left and right). In other embodiments, additional, fewer, and/or different zones may be considered. In at least one embodiment, the heath rating is a postural alignment and stability rating that is based on the measured deviations of these various body zones from healthy and/or neutral positions. The system 100 is configured to determine the health ratings in each zone in parallel, which saves time in comparison to a manual (e.g., in person) clinical evaluation. Additionally, the system 100 recalculates the measured deviations and health ratings whenever a scan is performed, giving the user a more holistic understanding of how different therapies are affecting various body areas and/or zones. In other words, the scoring takes into account whole-body structural patterns that are determined from the 3D mesh and captures changes in whole-body structural patterns each time a scan is performed. The system 100 is configured to establish and update scoring standards over time based on accumulated patient data (e.g., using machine learning techniques), as described above. Unlike existing methods, the system computes biophysics-based stresses and strains on patient joints from an accurate 3D mesh representation of the body surface, resulting in a more accurate and reproducible analysis.

In some embodiments, the system 100 is also configured to determine a dynamic movement and strength rating based on the analysis results from dynamic screens (e.g., range of motion, etc.). For example, the system 100 may be configured to determine hip and ankle flexion and range of motion based on dynamic screens that capture patient movement. The software can combine this data with information regarding the patient's weight and/or other physiological values to generate a holistic assessment of patient performance.

Figure 55:
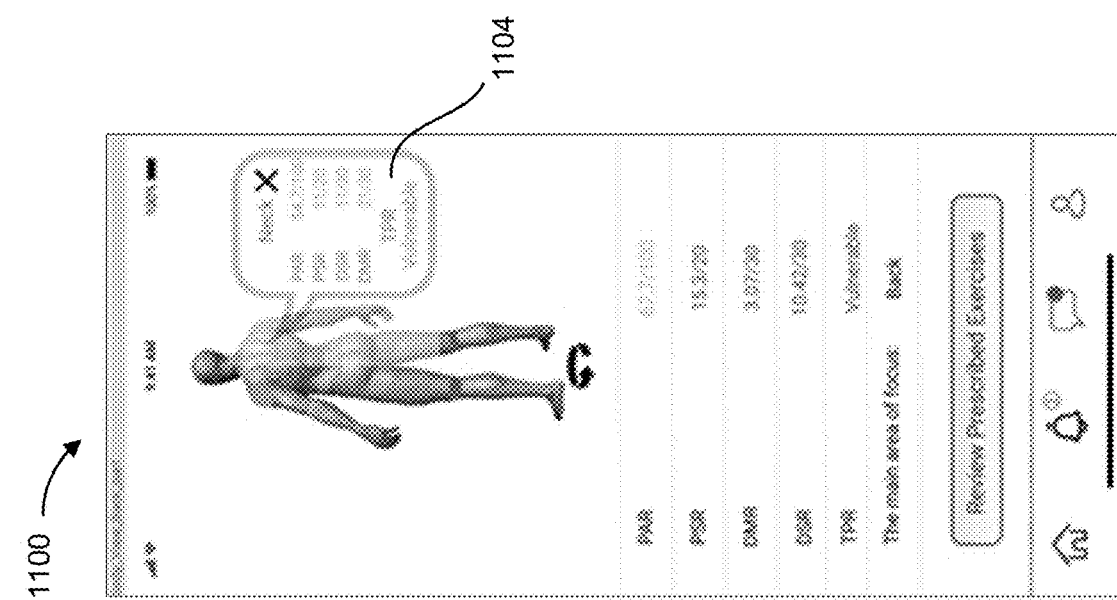
FIGS. 53-55 are display screens of a GUI that includes a visual representation of a human body, according to at least one embodiment.
Figure 54:
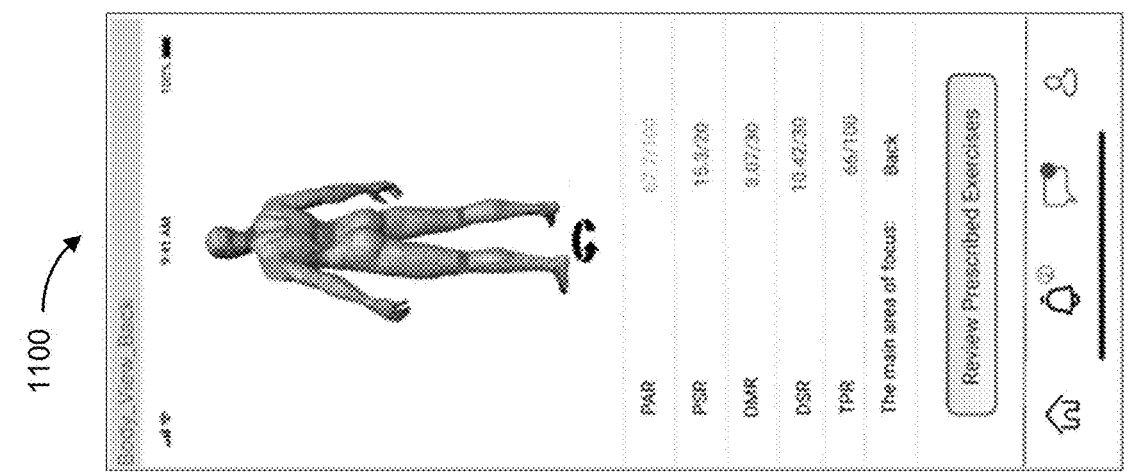
Figure 53:
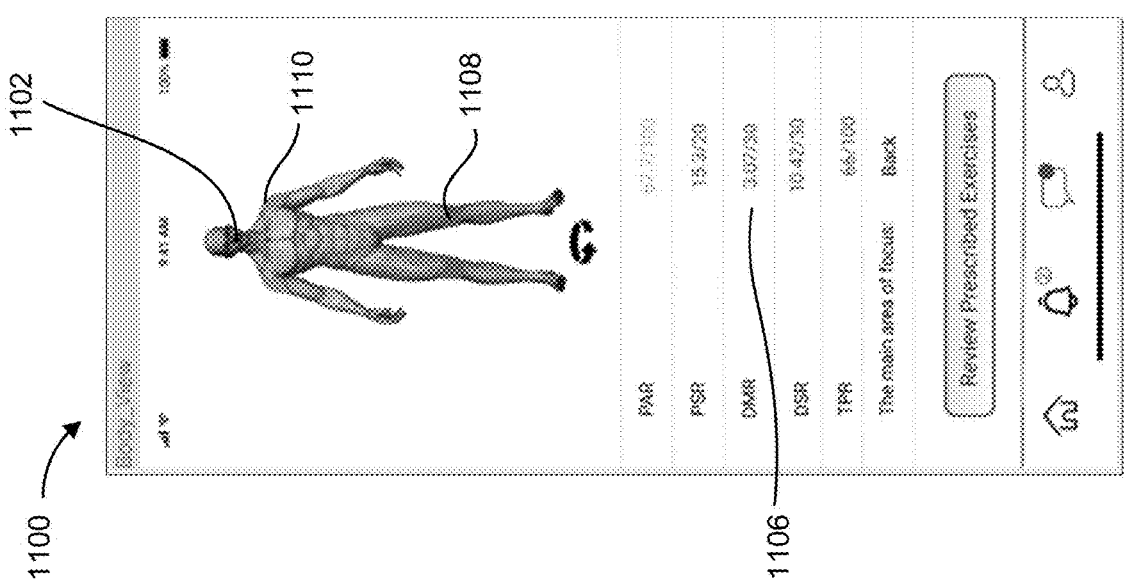

The system 100 is also configured to determine an omnibus health rating based on the individual health ratings in each zone (e.g., a total postural rating based on the individual postural ratings, a total dynamic rating based on the individual dynamic ratings, and omnibus rating based on a combination of the individual postural ratings and the individual dynamic ratings, etc.). In at least one embodiment, the system 100 is configured to overlay the health ratings for each zone, and the omnibus health rating onto a 3D representation of the patient (e.g., the volumetric mesh). For example, as shown in FIGS. 53-55, the system 100 is configured to generate a GUI 1100 with an image of the patient's volumetric mesh 1102. The GUI 1100 may be the same as or similar to (e.g., a modified patient and/or clinician oriented version of) the point picker GUI. The GUI 1100 is configured to allow a user to manipulate a position and/or orientation of the volumetric mesh 1102, for example, in response to user commands received through the user interface. For example, the user may be able to swipe their finger across a location on the touchscreen that corresponds with the volumetric mesh 1102 to rotate the volumetric mesh 1102 in the GUI 1100 (see FIGS. 180-181). The user may also be able to select various body areas (e.g., zones) on the mesh 1102, using the touchscreen or keypad (e.g., by interacting with visually perceptible icons, level indicators, adjustment bars, etc.), to obtain more detailed information about a specific body area. For example, FIG. 55 shows the GUI 1100 after a user has selected a neck area of the volumetric mesh 1102. In response to the user selection, the GUI 1100 presents a dialog box 1104 (e.g., text box, visually-perceptible window, etc.) with additional details and zone ratings that correspond with the neck area. The dialog box 1104 also provides a visual indication of the relative vulnerability of the neck area based on the measured deviations. In the embodiment of FIG. 55, the dialog box 1104 indicates a high vulnerability level for the neck area, suggesting that physical therapy is needed to align and/or strengthen the patient's body in the selected zone.

As shown in FIGS. 53-55, different areas of the body (e.g., zones) may be color coded to quickly indicate problem areas to the user that require further attention. For example, the color red 1108 may indicate extreme vulnerability of the body area/zone, and/or areas where measured deviations exceed threshold values for extreme vulnerability (e.g., threshold values stored in device memory, etc.). The color green 1110 may indicate that the measured deviations within the body area/zone are within nominal thresholds of the healthy and/or neutral position. Other colors (e.g., yellow, orange, etc.) may correspond with measured deviations that indicate moderate levels of vulnerability. As shown in FIGS. 53-55, the GUI 1100 may also include a listing of health ratings 1106 for designated body areas below the volumetric mesh 1102.

Referring to FIGS. 56-62, another example GUI 1200 is shown, according to an embodiment. The GUI 1200 presents a detailed and curated overview of outputs from the patient evaluation (e.g., the biometric screen, the clinical movement screen, the clinical diagnostic screen, etc.). The GUI 1200 also provides a plurality of tools to facilitate user interaction with the volumetric mesh 1202 and analysis results.

As shown in FIG. 56, the GUI 1200 includes a planar assessment view mode in which reference planes 1204 are displayed at each joint that visually indicate the measured amount of structural misalignment (e.g., deviations relative to healthy and/or neutral values) in various areas of the patient's body. The GUI 1200 also includes an alignment rating mode in which the GUI 1200 displays the health rating associated with each body area/zone (e.g., as a text indicator adjacent to each body area/zone). At least one of the planar assessment mode and/or alignment rating mode may include color coded identifiers on various areas of the 3D mesh to notify the user of regions where structural misalignment exceeds threshold values. In the embodiment of FIG. 56, the user navigates between the planar assessment mode and the alignment rating mode by selecting, via the user interface, a visually-perceptible icon (e.g., toggle, button, etc.) in a lower right hand corner of the GUI 1200.

The GUI 1200 is configured to allow the user to access additional details about key areas/zones by interacting with the 3D mesh. As shown in FIGS. 57-58, the user may select a specific area of the mesh to inspect measurements for a body zone in further detail. For example, in response to user input indicating the selection of a right shoulder area of the mesh (e.g., by tapping on a touchscreen in the area of the patient's shoulder), the GUI 1200 is configured to display a detailed view screen that provides information about measured structural misalignment and the relative risk associated with the misalignment. In a scenario where multiple scans of a patient have been taken over time, the GUI 1200 may display a progress history icon 1208 that allow the user to access charts and/or other graphical depictions of the accumulated scan history over time.

Figures 59, 60, 61, 62:
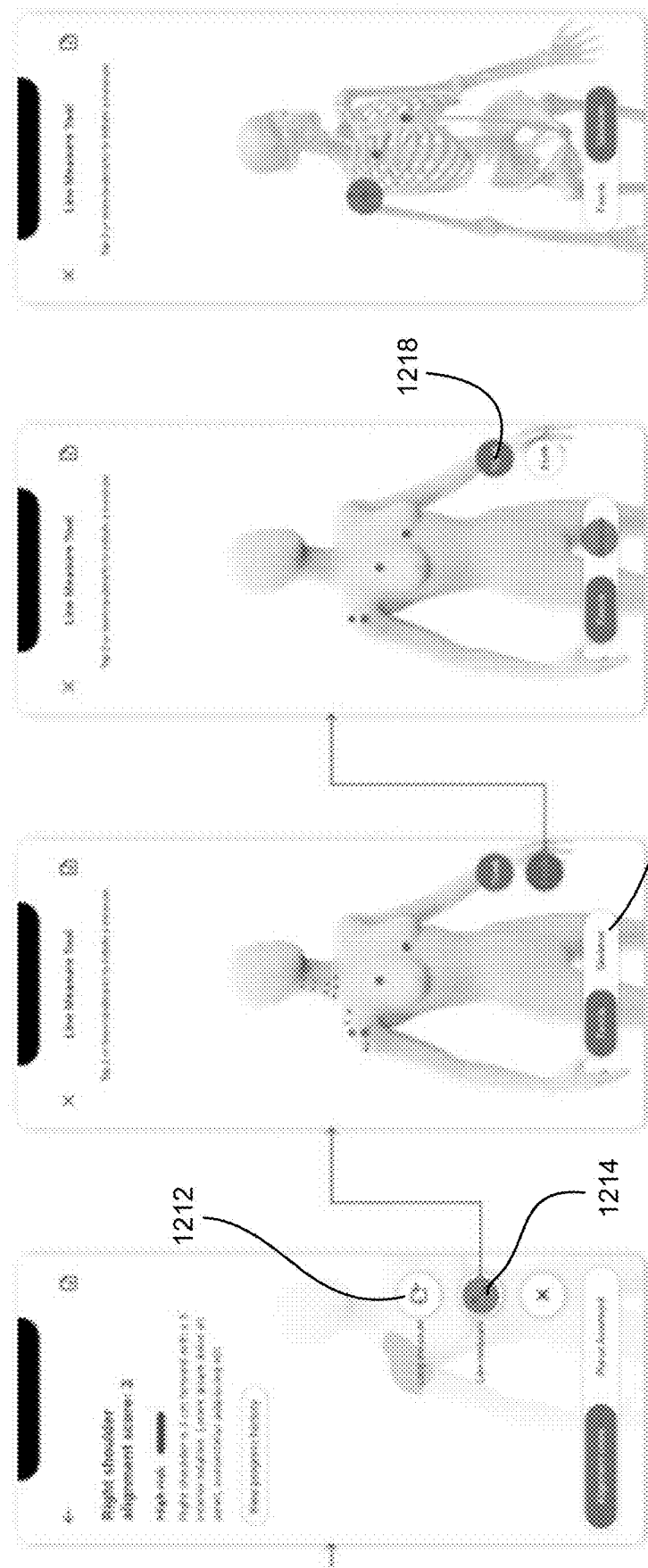

The GUI 1200 may also present tools that allow the user to take manual measurements from the 3D mesh. In the example of FIGS. 58-59, the GUI 1200 includes a tools icon 1210 that, when selected, displays various measurement tools that may be enabled for the user. The tools may include any form of selection and/or measurement tool, such as a loop measurement tool 1212 that allows the user to determine the distance along a path or loop of multiple points (e.g., a circumference of a patient's leg, etc.) and/or a line measurement tool 1214 that allows the user to determine a length between two points and/or landmarks on the 3D mesh. FIGS. 59-60 illustrate the operation of the line measurement tool 1214. As shown in FIG. 60, once selected, the GUI 1200 displays a measuring mode with icons 1216 that allow a user to navigate between data points and/or landmarks on the fascia or skeleton. The GUI 1200 may also be configured to allow selection of any data points along the 3D mesh. As shown in FIGS. 61-62, the GUI 1200 also includes view icons 1218 that are configured to allow a user to navigate between different view modes for the 3D mesh (e.g., to view a patient's body surface or skeleton). Selecting two points using the line tool generates a straight line between the two points, from which the system can determine a distance between the two points. In other embodiments, the GUI 1200 may include additional tools such as an angle measurement tool, plane and/or line creation tool, and the like.

FIG. 63 shows another example embodiment of an assessment report and/or assessment GUI 1250 that may be generated by the system 100. The assessment report may include one or more views of the patient (e.g., volumetric mesh) and may include visually-perceptible icons overlaid onto different body areas that indicate risk values and/or scores associated with their respective body areas. The visually-perceptible icons may provide the actual risk value and/or score and may also be color coded based on the relative level of risk so that a user can quickly identify areas to focus on (e.g., red for high risk or "needs attention", yellow for medium risk or "needs focus", and green to indicate areas with minimal risk or "optimal", etc.). The assessment report may also include a table that lists risk levels and/or values for each body zone or area, as shown in FIG. 64.

In at least one embodiment, the system 100 determines the risk values based on one, or a combination of, user input (e.g., subjective measurements), assessments from professionals in the field, and scan data (e.g., objective measurements from biometric screens performed by the assess module). The risk levels may be determined based on the risk value and/or score. For example, the system 100 may be configured to access a lookup table that includes normative ranges of the risk value and/or score for different body zones, and to determine the risk level by comparing the risk value with the normative ranges.

Referring to FIG. 65, a method 1270 of determining a combined risk score for a body area, according to at least one embodiment. At 1272, the software performs a biometric assessment screen to determine a plurality of postural deviations for a corresponding plurality of body zones. Operation 1272 may include performing any one of the biometric assessments described above (e.g., a spinal mapping assessment, a hip rotation assessment, a vertical loading assessment, etc.).

At 1274, the software determines a plurality of zone risk scores based on a comparison between each one of the plurality of postural deviations and a list of threshold ranges that correspond to the postural deviation. For example, operation 1274 may include iterating through a lookup table to identify the list of threshold ranges that correspond to the postural deviation. The list may include a plurality of ranges of postural deviations, where each range is associated with a different zone risk score. Operation 1274 may include determining the risk score based on (or that satisfies) the range that corresponds with the postural deviation (e.g., a risk score of 0 if the postural deviation is within or outside of a low risk range or low risk threshold corresponding to healthy values of postural deviation, a risk score of 1 if the postural deviation is within a range corresponding to moderate risk levels of postural deviation, a risk score of 2 if the postural deviation is within or outside of a high risk range or high risk threshold, etc.). Operation 1274 may include generating a graphical representation of the zone risk scores and overlaying the zone risk scores on a GUI (such as GUI 1217 of FIG. 63) and/or populating a table that summarizes the zone risk scores as shown in FIG. 64. The GUI 1217 may include color-coded text or visually-perceptible icons 1218 that provide an indication of the risk levels (e.g., green for low risk, yellow for moderate risk, red for high risk, etc.).

At 1276, the software determines the combined risk score for a body area based on the plurality of zone risk scores. Operation 1270 may include retrieving the plurality of zone risk scores that are associated with the body area. For example, the body area may be a hip/pelvis region of the mesh (e.g., the patient's body). Operation 1270 may include combining (e.g., summing, etc.) zone risk scores from a pelvic position screen and/or from the vertical load screen (e.g., a postural deviation of the patient's lateral malleolus to the hip position, etc.). In some embodiments, operation 1270 may include adjusting at least one of the zone risk scores by a weighting factor depending on a relative importance of the biometric screens for that body area. Operation 1270 may include determining the combined risk score by normalizing the combined zone risk scores by a worst case risk score for that body area. The software may be configured to generate a risk score table that summarizes the combined risk score for user review (as shown in FIG. 64).

Method 1270 may be repeated for different body areas. In some embodiments, method 1270 may further include determining an overall risk score for a patient that is indicative of an overall level of risk for the patient. For example, method 1270 may include combining a plurality of combined risk scores for different body areas to generate the overall risk score (in a similar manner as is used to determine the combined risk score from the zone risk scores, etc.). In other embodiments, method 1270 may include additional, fewer, and/or different operations.

Prescribe Operations

In the prescribe block 108 (FIG. 1), the system 100 determines an exercise regimen based on at least one of (1) data from patient survey results, (2) measurements of structural misalignment and/or patterns of structural misalignment that are received from the assess block 106, and/or (3) health ratings and/or scores (e.g., from clinicians and/or other professionals in the field). The exercise regimen may be transmitted to a second user device (e.g., a clinician/reviewer device, etc.) and presented to the clinician (e.g., a physical therapy coach, sports medicine provider, etc.). The clinician may then review the exercise regimen and make adjustments if needed (e.g., reorder exercises, add exercises, remove exercises, etc.). In at least one embodiment, the system 100 includes a library of exercises that the system 100 may select and/or may be prescribed by a clinician. The exercises may be stored in a database in device memory (e.g., memory 208 of FIG. 2), and may include information about how to perform the exercise, and what areas and/or conditions the exercise may be used to treat.

In at least one embodiment, the system 100 implements detailed prescription algorithms (e.g., exercise progression selection logic, routine selection logic, etc.) to select and prioritize exercises and/or exercise routines based on the patient's unique combination of reported pain, measured structural misalignment, health ratings, vulnerabilities, and/or needs. For example, the system 100 may be configured to recommend a specific exercise progression with certain patterns of pain across the 14 body zones (described above) to reduce levels of reported pain. Once the pain level has been reduced, the system 100 may select and prescribe specific exercise progressions to address structural misalignment (e.g., to reduce measured deviations from the clinical movement screens that may not necessarily cause any pain, etc.). The system 100 may prescribe routines by day or by week, add or remove exercises based on reported pain levels, vulnerabilities, and health scores, and also allows for manual review and adjustment by a clinician before initiating the prescription.

Figure 66:
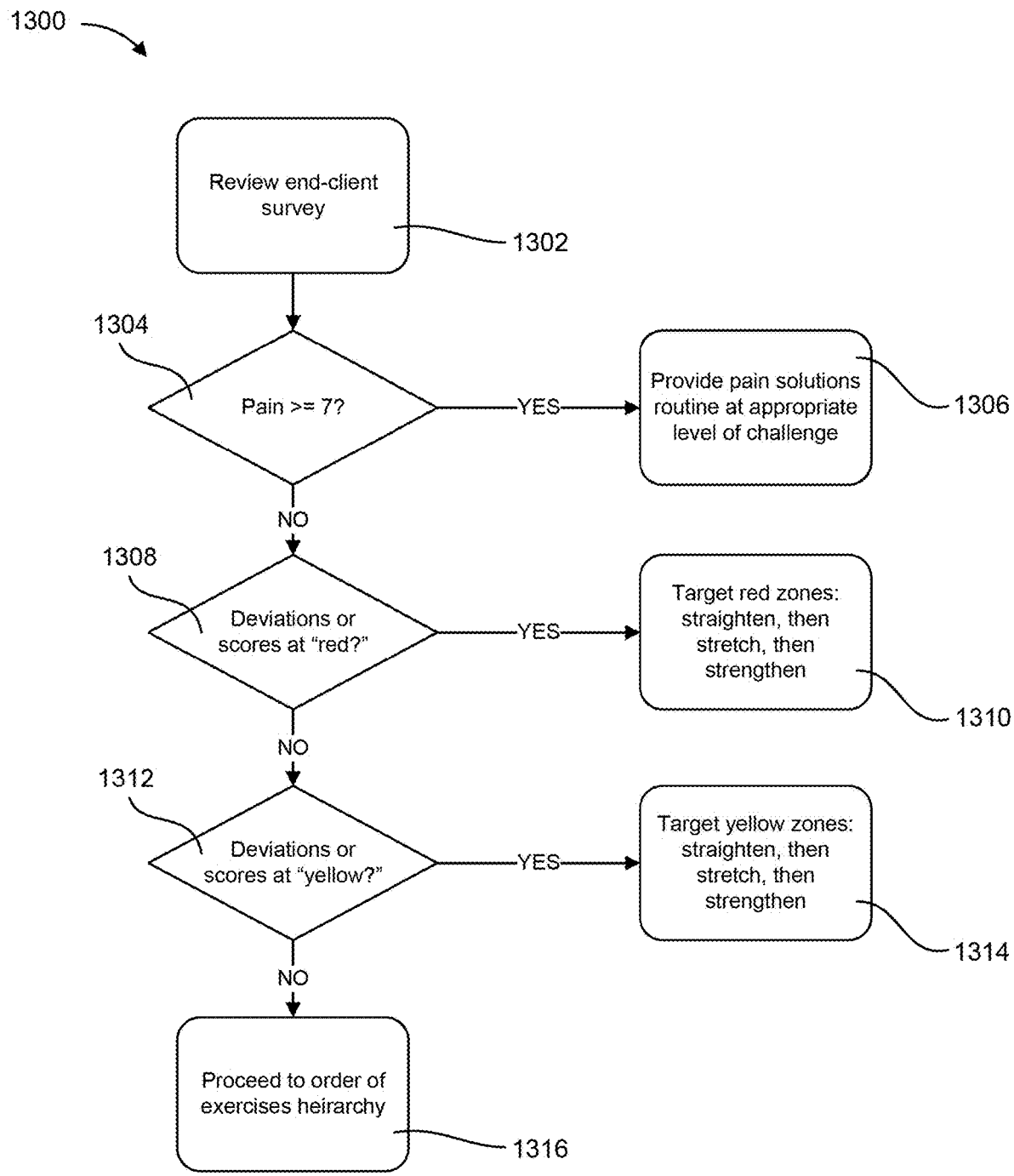
FIG. 66 is a flow diagram of a method of prescribing exercises based on a patient's pain and/or measured structural misalignment, according to an embodiment.

Referring to FIG. 66, a flow diagram of a method 1300 of prescribing exercises based on the patient's pain and/or structural misalignments is shown, according to an embodiment. The method 1300 may be implemented by the device 200 of FIG. 2, for example, through a software application installed on the device 200 (e.g., through the prescribe module 216). As such, reference will be made to the device 200 when describing method 1300. In another embodiment, the method 1300 may include additional, fewer, and/or different operations. It will be appreciated that the use of a flow diagram and arrows is not meant to be limiting with respect to the order of flow operations. For example, in one embodiment, two or more of the operations of method 1300 may be performed simultaneously.

At 1302, the prescribe module 216 reviews patient survey data and/or values of structural misalignment received from the assess module 214. The patient survey data may include information about the levels of pain that a patient is experiencing in different body areas/zones. For example, the pain levels may be expressed using a numerical value between 0 and 10, with 0 indicating no pain and 10 indicating the highest levels of pain. Operation 1302 may include accessing survey data (e.g., the pain levels) from memory 208. At 1304, the prescribe module 216 compares the pain levels for each body zone/area with pain thresholds stored in memory 208 (e.g., pain levels associated with diminished quality of life, unbearable pain, etc.). If the pain level for a given body area/zone satisfies the pain threshold corresponding to that area (e.g., if the pain level is greater than or equal to the pain threshold for that area), the prescribe module 216 identifies and prioritizes exercises that are tailored to reducing pain in that particular body zone/area (at 1306). The prescribe module 216 may also be configured to determine an appropriate level of challenge for the exercises, such as a type of exercise for treating the affected area, an intensity (e.g., more difficult exercises, etc.), and/or a duration over which the exercise(s) should be performed.

In some embodiments, the prescribe module 216 is configured to determine exercise routines based on patient data. The prescribe module 216 may be configured to access a series of exercise prescription tables (e.g., exercise tables, routine selection tables, etc.) stored in memory 208 to determine an exercise regimen based on the pain levels that are reported by the patient. The exercise prescription tables provide an ordered listing of exercises that are crafted to reduce pain and/or improve strength of the patient so that the patient can progress to a more intense exercise regimen.

Each table may include a body area identifier that corresponds with one or more body areas or zones for the patient. The table may separate the exercises into three groupings or sets arranged along a primary row of the prescription table. Pain identifiers that correspond with each grouping may be arranged along a first column of the prescription table. The pain levels may be qualitative values, but may correspond with a range of numerical values in some embodiments (e.g., low pain levels from 1-3, medium pain levels from 4-6, and high pain levels from 7-10, or another set of values depending on what pain levels the exercises are tailored to).

In response to a reported pain level in a patient's foot, the prescribe module 216 may iterate through the prescription tables to match the corresponding body area identifier (e.g., foot zone) with the reported body area. The prescribe module 216 may then iterate through the table to retrieve the list of exercises corresponding to the reported pain level. The exercise intensity may scale with reported levels of pain. In other embodiments, the exercise regimens provided in the prescription tables may scale with a vulnerability level of the body area to injury, and/or based on target areas specified by the user (e.g., clinician, etc.). The clinician may also have the ability to review and/or modify the prescribed exercises manually before they are transmitted to the patient, as will be further described. It will be appreciated that other factors can also be built into the prescription tables including, but not limited to, data regarding user compliance with the prescribed treatment, measured results over time, changes in survey results over time, and the like. In at least one embodiment, the system may be configured to input this data as a training set into a machine learning algorithm to improve exercise prescription and reduce the time required to advance the patient to more aggressive levels of treatment.

Returning to FIG. 66, if the pain level does not satisfy the pain threshold, then the method 1300 proceeds to 1308. At 1308, the prescribe module 216 reviews measured misalignment and/or deviations between actual structural alignment in a given body area/zone and healthy/neutral values. If the deviations satisfy extreme vulnerability thresholds (e.g., red regions in the 3D mesh), than the prescribe module 216 prioritizes exercises that treat those areas, at 1310. Operation 1310 may include selecting exercises in a specific progression to reduce vulnerabilities in the affected area/zone. For example, operation 1310 may first include selecting exercises to straighten the affected area (e.g., a patient's spine, etc.). The straightening exercises may be followed by exercises to stretch the affected area and thereby reduce the likelihood of subsequent injury. Finally, operation 1310 may include selecting exercises to strengthen the affected area over time, or adjacent areas to reduce the strain and/or stress on the affected area.

Once all of the extreme patient vulnerabilities have been addressed (e.g., reduced below extreme vulnerability thresholds), the prescribe module 216 selects exercises to treat any lower priority deviations (e.g., deviations and/or structural misalignments that satisfy moderate vulnerability thresholds, etc.), at 1312 and 1314. Operation 1314 may be similar in operation to 1310, and includes selecting exercises in a specific progression to further reduce patient vulnerabilities.

Figure 67:
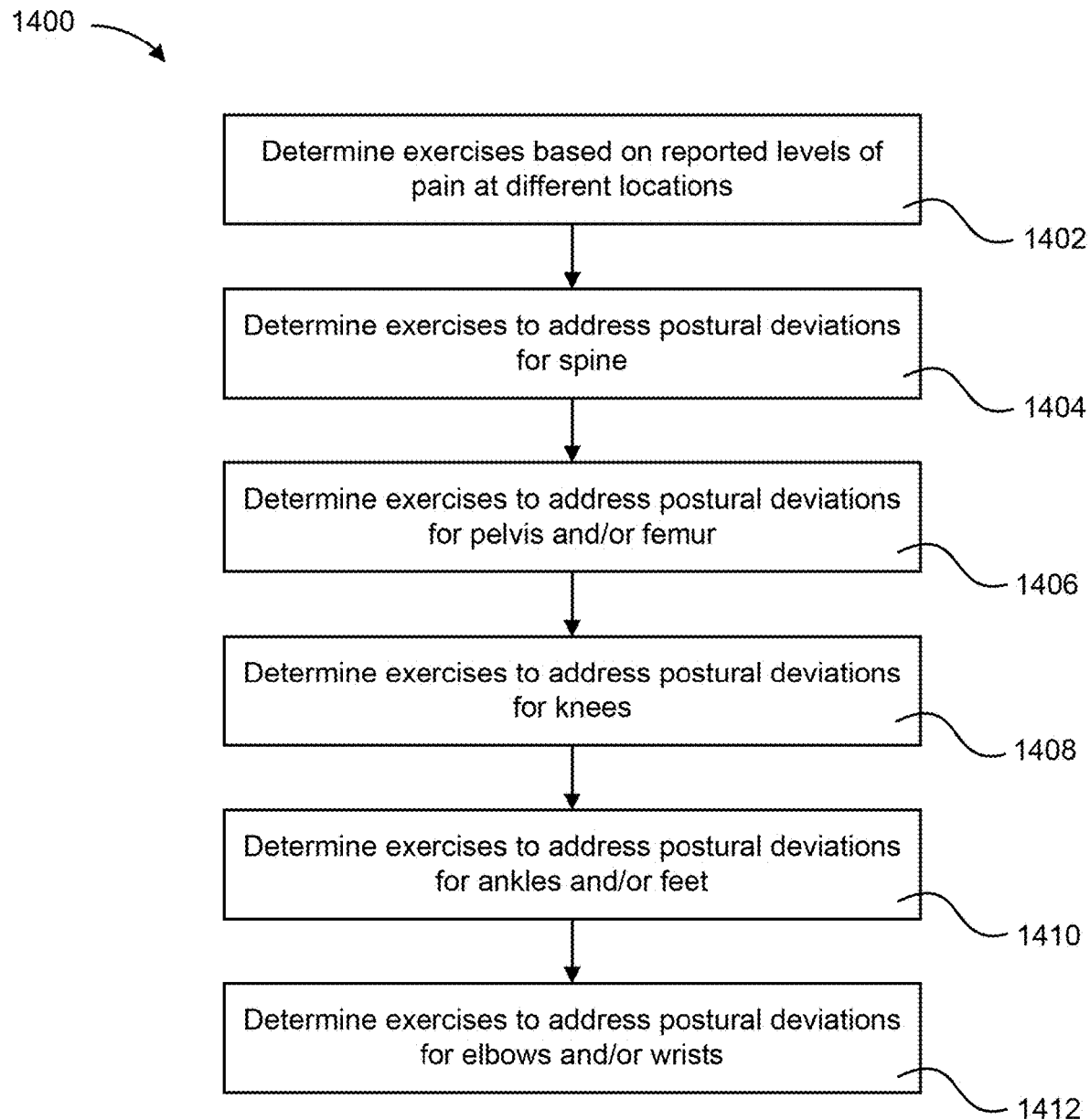
FIG. 67 is a flow diagram of an exercise prescription hierarchy, according to an embodiment.

At 1316, after the patient's pain and vulnerabilities levels have been sufficiently reduced, the prescribe module 216 selects an order of exercises in a hierarchy that builds up the most critical foundations of the patient's body first (e.g., the core, spine, etc.), followed by other less critical areas (e.g., outer extremities, etc.) that can be more easily treated once the critical foundations have been developed. Referring to FIG. 67, a flow diagram of an example exercise hierarchy 1400 is shown, according to an embodiment. At 1402, the prescribe module 216 determines (e.g., selects and prescribes) exercises that further reduce any pain that the patient is experiencing, such as any pain reported on the survey but not exceeding any prescribed pain thresholds. Next, at 1404, the prescribe module 216 determines exercises that address postural deviations in a patient's core areas such as (1) the spine and/or (2) the pelvis and/or femur (at 1406), followed by exercises that reduce postural deviations in the patient's outer extremities such as the knees (at 1408), ankles and/or feet (at 1410), and finally by exercises to reduce postural deviations in the elbows and/or wrists (at 1412).

Figure 70:
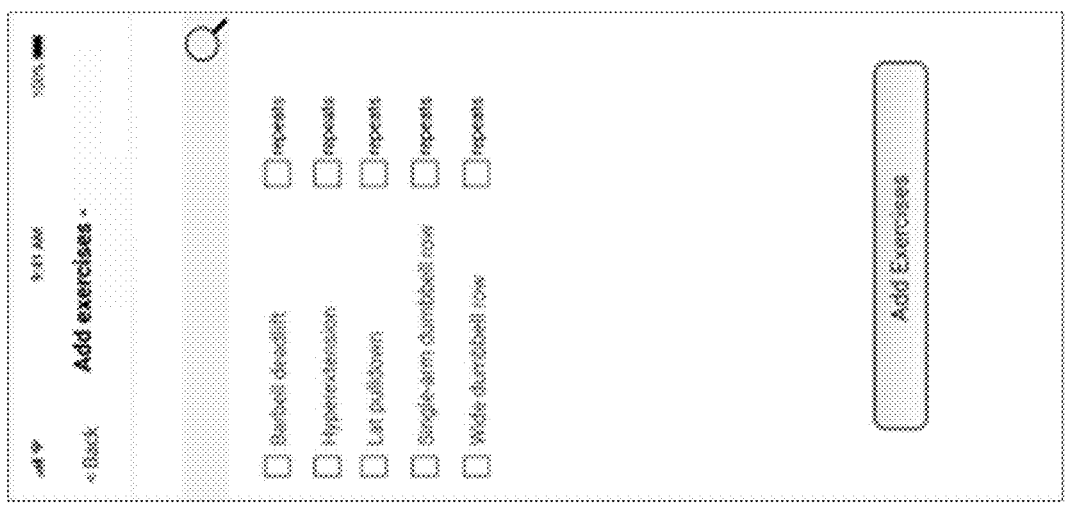
FIGS. 68-75 are display screens of a GUI that facilitates exercise prescription and management, according to at least one embodiment.
Figure 69:
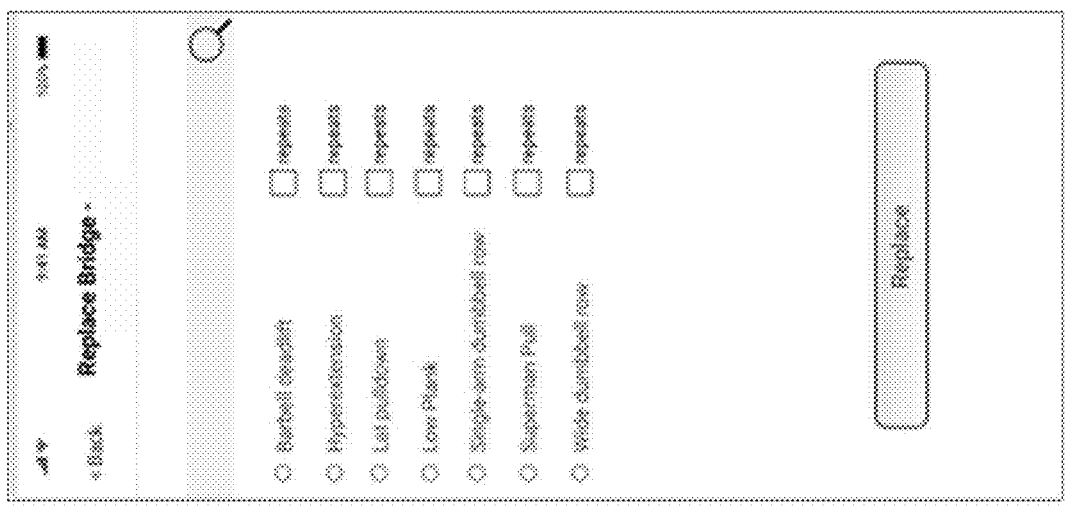
Figure 68:
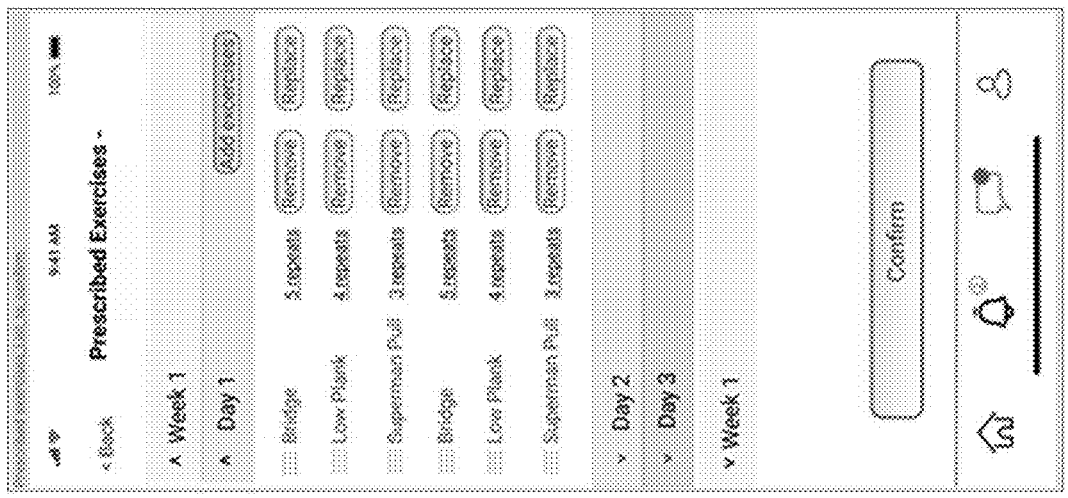

The system 100 (e.g., prescribe module 216) is configured to populate the prescribed exercises from methods 1300 and/or 1400 into a calendared list and present the list in an easy-to-interpret format through the GUI. Referring to FIGS. 68-70, a GUI 1500 is shown that displays a list of exercises for user review is shown, according to an embodiment. In at least one embodiment, before transmitting the list to the patient, the list of exercises is transmitted by the system 100 (FIG. 1) to a second user device (e.g., a clinician computing device that is remote from the patient's computing device) so that a doctor, physical therapist, or other clinician can review and update the list and finalize the prescription. As shown in FIG. 201, the list may include groupings of exercises for each day of the week or over another suitable time period. Details about each individual exercise may also be shown, such as a number of repetitions for each exercise type. As shown in FIGS. 69-70, the clinician may edit the list of exercises to add, remove, and/or replace exercises on the list.

Figure 71:
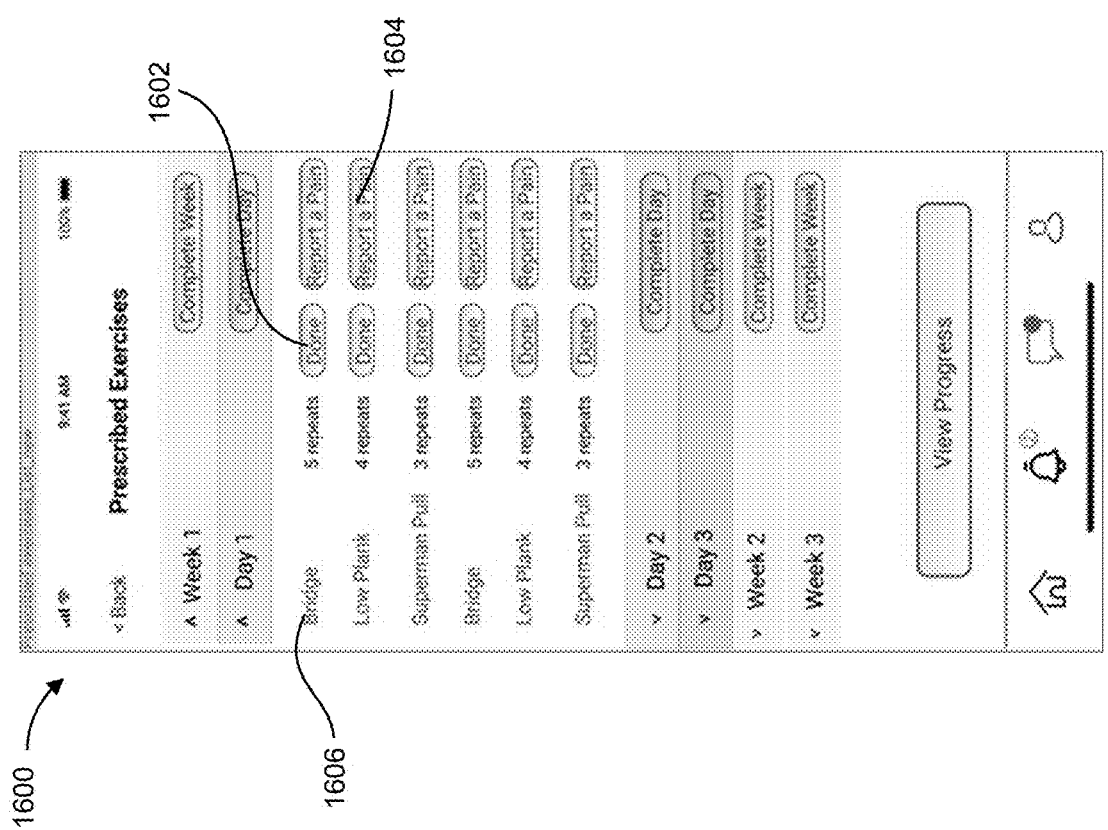
Figures 72, 73, 74, 75:
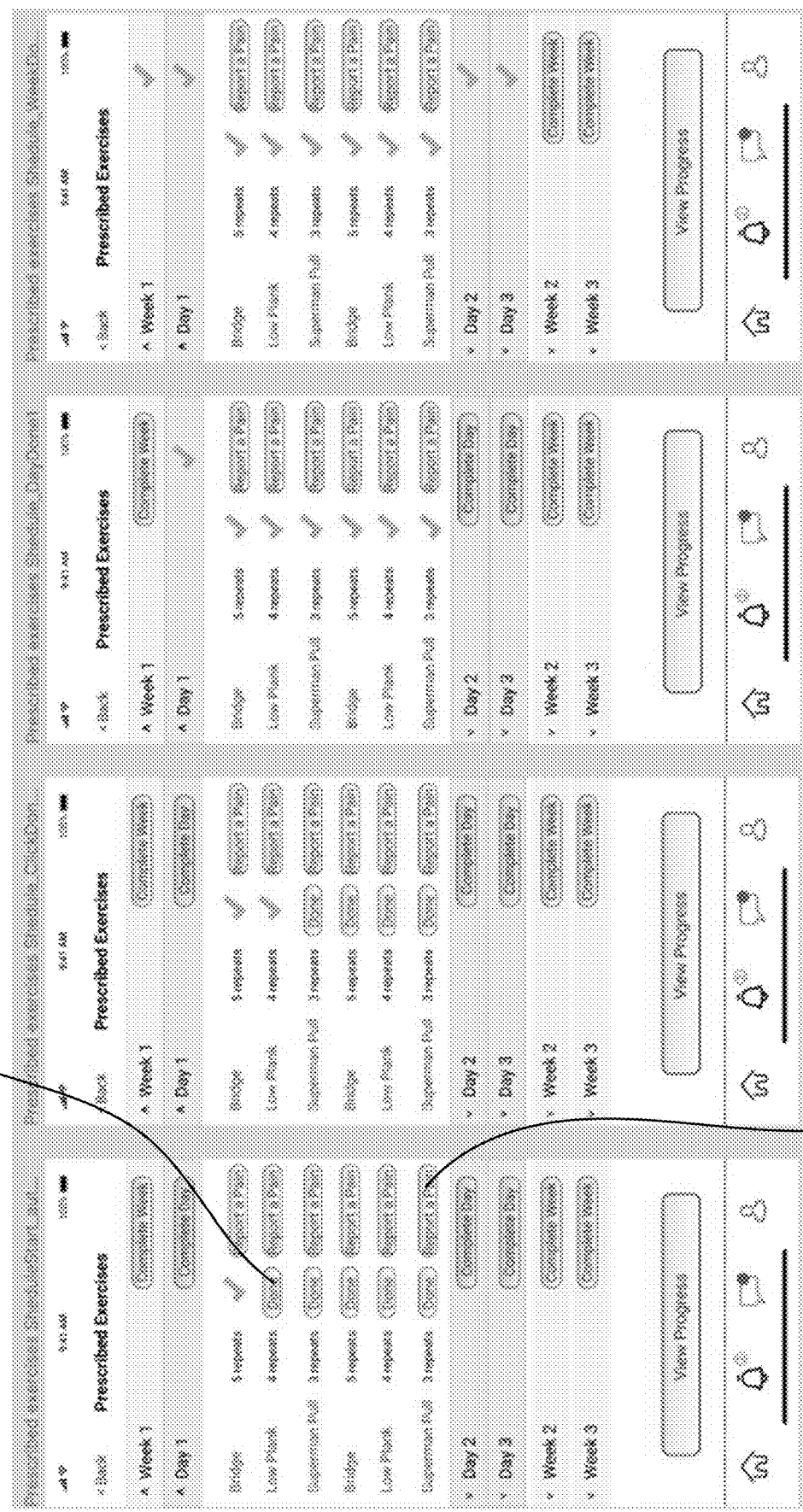

After the clinician reviews and updates the list to their satisfaction, the finalized prescription is transmitted to the patient (e.g., to a patient's mobile device). Referring to FIG. 71, a GUI 1600 is shown that displays details of the prescription to the patient. As shown in FIG. 71, the GUI 1600 includes a list of exercises in groupings for each day of the week, along with progress icons 1602 and reporting icons 1604 for each exercise. The GUI 1600 also includes selectable links 1606 that prompt the GUI 1600 to display additional details about various exercises. In some embodiments, the details for each exercise include a brief video illustrating how the exercise is performed (e.g., proper form for the exercise, etc.). The details may also include a description of the area of the body that the exercise will affect, as well as difficulty and risk levels associated with the exercise. As shown in FIGS. 72-75, a user may report progress through the GUI 1600 (e.g., via the progress icon 1602), and the progress may be transmitted to the clinician device for further review and analysis. Treatment progress may also be saved to memory for further analysis by the system (e.g., the predict block 110 of FIG. 1). In the event that the user experiences any pain during the exercise, the user may report this pain and any related details to their clinician through the GUI 1600 (e.g., by selecting the reporting icon 1604).

Predict Operations

In the predict block 110 (FIG. 1), the system 100 is configured to tabulate historical data (e.g., biometric data on patient progression) and report the data to the user. For example, the system 100 may be configured to compile multiple scans of the patient into system memory (e.g., device memory 208 of FIG. 2), to compare data between scans, and to display the results to the user through an interactive GUI.

Figure 78:
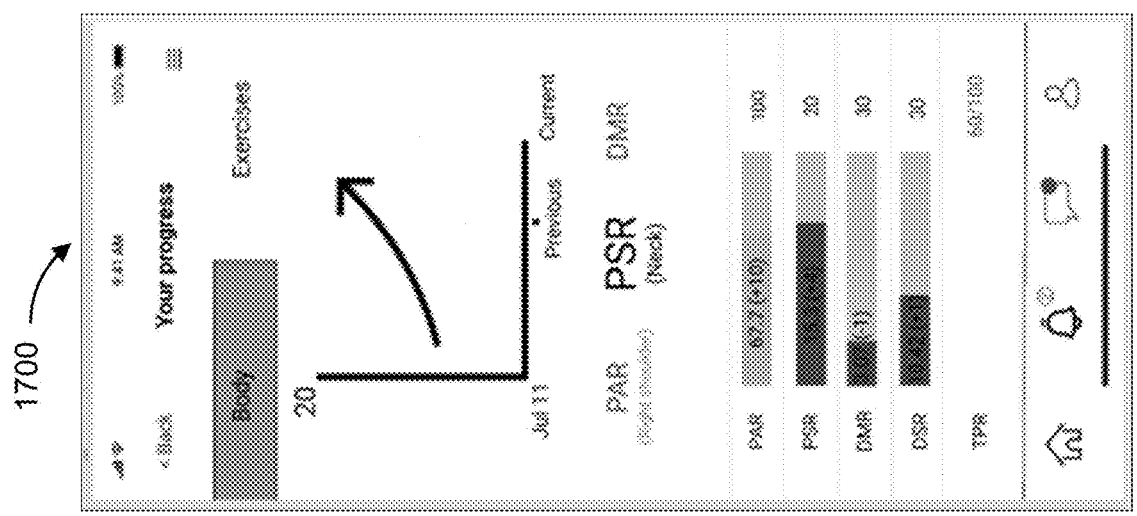
FIGS. 76-78 are display screens of a GUI for tracking treatment progress of physical therapies, according to at least one embodiment.
Figure 77:
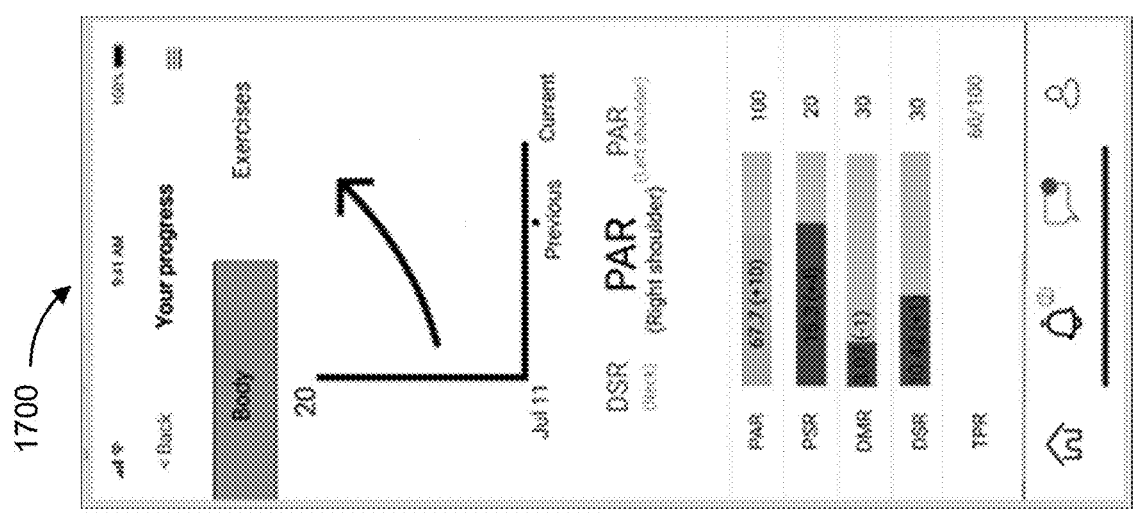
Figure 76:
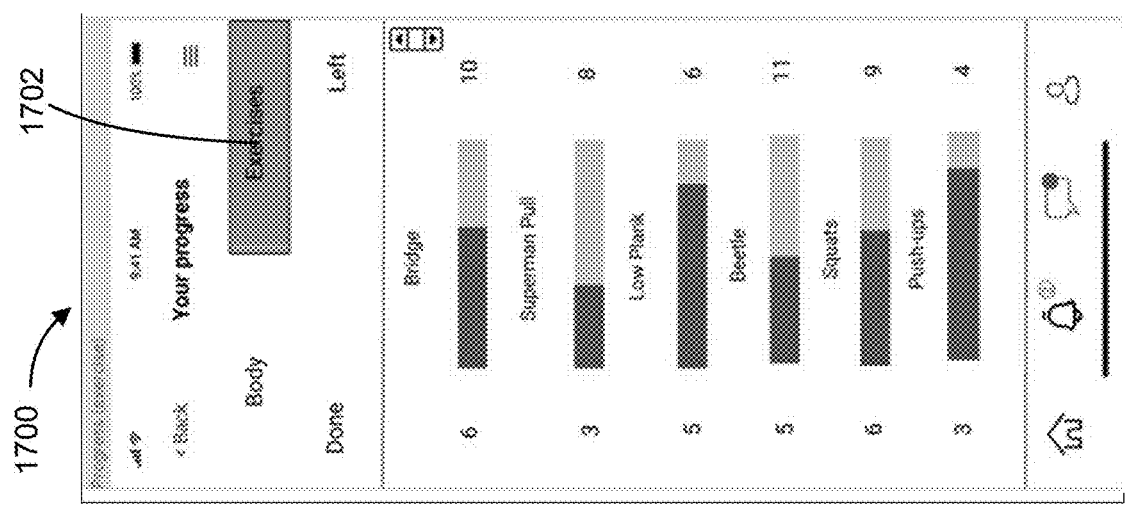

Referring to FIGS. 76-78, a GUI 1700 that displays a visual representation of treatment progress is shown, according to an embodiment. As shown in FIG. 76, a first display mode of the GUI 1700 displays the user's progression through the prescribed exercise regimen (e.g., progression through an overall number of exercises for the entire treatment period). Progress is indicated for each exercise type using a horizontal progress bar in the GUI 1700. Among other benefits, the GUI 1700 can be used by a physical therapist or clinician to track patient adherence to the prescription and to detect potential vulnerabilities (e.g., vulnerability to injury) based on changes in the patient's condition throughout the treatment period. As shown in FIGS. 77-78, a second display mode of the GUI 1700 displays changes in the patient's postural deviations, health ratings, and/or omnibus rating over the treatment period. A user can navigate between modes of operation by selecting a mode icons 1702 near an upper edge of the GUI 1700. It will be appreciated that the number, type, and size of visual indicators may be different in various embodiments.

The system may be configured to update the GUI 1700 each time a scan is performed or a survey is collected. Among other benefits, this allows the user to track their progress in real time, and without input from their physical therapist, providing encouragement to the patient throughout the treatment period. The GUI 1700 includes a chart that shows trends in how the patient's health rating has changed over time, and horizontal indicator bars that correspond with real-time values of the patient's health ratings.

In at least one embodiment, the system is configured to update risk models for the assess block 106 to improve exercise prescription for the patient. For example, as described above, the system may input historical data into a machine learning algorithm that can identify meaningful trends based on various potential correlations, between individual landmarks, areas of pain, measurements based on specific landmarks or combinations of landmarks in one or more body areas or zones, changes in landmark position over the treatment regimen, compliance reporting, and the like.

The system (e.g., machine learning algorithm) may also be configured to estimate future performance based on historical trends and/or data from similar treatment experienced by other patients with similar physiological conditions (e.g., over populations of patients with similar body types, pain levels, vulnerabilities, and/or populations of patients participating in similar treatment regimens). Similar machine learning techniques may be employed in other areas of the clinical screening and assessment system to facilitate, for example, landmark placement (e.g., improved identification of landmarks and changes in body position over the course of treatment), identification of potential areas of vulnerability, exercise prescription, risk assessment, projected outcomes based on user inputs (e.g., survey data), and many more.

The system may also be configured to transmit data to third parties for further review and/or comparison. In this way, the system could share adherence, activity, and/or outcome data with other organizations.

While the instant disclosure has been described above according to its preferred embodiments, it can be modified within the spirit and scope of this disclosure. This application is therefore intended to cover any variations, uses, or adaptations of the instant disclosure using the general principles disclosed herein. Further, the instant application is intended to cover such departures from the present disclosure as come within the known or customary practice in the art to which this disclosure pertains.

Notwithstanding the embodiments described above in FIGS. 1-78, various modifications and inclusions to those embodiments are contemplated and considered within the scope of the present disclosure. Any of the operations described herein can be implemented as computer-readable instructions stored on a non-transitory computer-readable medium such as a computer memory.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Moreover, although the figures show a specific order of method operations, the order of the operations may differ from what is depicted. Also, two or more operations may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection operations, processing operations, comparison operations, and decision operations.

It is important to note that any element disclosed in one embodiment may be incorporated or utilized with any other embodiment disclosed herein.

What is claimed is:

1. A method of extracting and displaying postural measurements from patient data, comprising:
    retrieving, by a processor of a computing device, the patient data from memory, the patient data comprising a geometric mesh representation of a patient, the geometric mesh representation including a plurality of data points corresponding to spatial coordinates of a plurality of vertices in three dimensions;
    determining, by the processor, at least one reference geometry along the geometric mesh representation at a fixed position with respect to the spatial coordinates;
    determining, by the processor, a plurality of landmarks corresponding to one of skeletal or soft tissue anatomy for the patient;
    determining, by the processor, a plurality of postural deviations of the patient by comparing the at least one reference geometry and the plurality of landmarks, at least one of the plurality of postural deviations being an amount of structural misalignment of at least a portion of the geometric mesh representation;
    determining, by the processor, a first body risk score from a first subset of the plurality of postural deviations corresponding to a first body area, and a second body risk score from a second subset of the plurality of postural deviations corresponding to a second body area;
    adjusting at least one of the first body risk score or the second body risk score by a weighting factor;
    determining, by the processor, a combined risk score from the first body risk score and the second body risk score, comprising normalizing at least one of the first body risk score or the second body risk score by a worst case body risk score corresponding to the first body area or the second body area; and
    displaying, by a display of the computing device, a graphical user interface indicating the combined risk score.

2. The method of claim 1, wherein determining the at least one of the plurality of landmarks comprises:
    determining, by the processor, using a call function from a 3D mesh manipulation library, a first horizontal section at a first position of the geometric mesh representation along a first coordinate axis of the spatial coordinates and a second horizontal section of the geometric mesh representation at a second position along the first coordinate axis; and
    determining a center of volume of a volumetric slice of the mesh between the first horizontal section and the second horizontal section.

3. The method of claim 1, wherein determining the at least one reference geometry comprises:
    determining, by the processor, using a first call function from a 3D mesh manipulation library, a set of at least three points on the geometric mesh representation within a threshold range of at least one of the plurality of landmarks;
    determining, by the processor, using a second call function from the 3D mesh manipulation library, a reference plane that fits the set of at least three points, the reference plane approximating a surface fragment of a body area of the 3D mesh; and
    determining an orientation of the surface fragment comprising determining a normal vector of the reference plane.

4. The method of claim 1, wherein determining at least one postural deviation of the plurality of postural deviations comprises:
    determining a healthy range of postural deviation by removing a threshold percentage of outliers from a reference set of patient data, the reference set including measurement data from a plurality of patients; and
    classifying the at least one postural deviation with a risk value based on a comparison between the at least one postural deviation and the healthy range.

5. The method of claim 1, further comprising determining, by the processor, from scan data of the patient comprising a plurality of images of the patient from at least two sides of the patient, a geometry file corresponding to the geometric mesh representation, the geometry file including a list of the plurality of vertices and a list of a plurality of faces forming a three dimensional geometric representation of the patient, each face of the list of faces including three vertex indices from the plurality of vertices, wherein retrieving the geometric mesh representation of the patient comprises retrieving the geometry file.

6. The method of claim 1, wherein determining the at least one reference geometry comprises generating at least one of a reference line or a surface that corresponds with neutral values of patient posture.

7. The method of claim 1, wherein at least one of the plurality of landmarks comprises a center of volume of a first body portion of the geometric mesh representation, wherein the at least one reference geometry comprises a center of volume of a second body portion of the geometric mesh representation, and wherein determining at least one of the plurality of postural deviations comprises:

projecting, by the processor, the center of volume of the first body portion and the center of volume of the second body portion onto a ground plane of the spatial coordinates; and determining a shortest distance between the projections.

8. The method of claim 7, wherein determining the at least one reference geometry comprises:

identifying, by the processor, from the patient data, a first reference point along a height of the geometric mesh representation relative to the ground plane based on an average value taken from a reference set of patient data; and determining, by the processor, a center of volume of a slice of the patient data at the first reference point using a numerical integration algorithm from a 3D mesh manipulation library.

9. The method of claim 1, wherein the combined risk score is a vulnerability level associated with a risk of injury to the patient.

10. A system for evaluating patient data, comprising:

a memory storing the patient data, the patient data comprising a geometric mesh representation of a patient, the geometric mesh representation including a plurality of data points corresponding to spatial coordinates of a plurality of vertices in three dimensions;

a display; and a processing circuit communicably coupled to the memory and the display, the processing circuit configured to:

determine at least one reference geometry along the geometric mesh representation at a fixed position with respect to the spatial coordinates;

determine a plurality of landmarks corresponding to one of skeletal or soft tissue anatomy for the patient;

determine a plurality of postural deviations of the patient by comparing the at least one reference geometry and the plurality of landmarks, at least one of the plurality of postural deviations being an amount of structural misalignment of at least a portion of the geometric mesh representation;

determine a first body risk score from a first subset of the plurality of postural deviations corresponding to a first body area, and a second body risk score from a second subset of the plurality of postural deviations corresponding to a second body area;

adjusting at least one of the first body risk score or the second body risk score by a weighting factor;

determine a combined risk score from the first body risk score and the second body risk score, comprising normalizing at least one of the first body risk score or the second body risk score by a worst case body risk score corresponding to the first body area or the second body area; and displaying, on the display, the combined risk score.

11. The system of claim 10, further comprising a scan device communicably coupled to the processing circuit, the scan device configured to capture scan data of a body of the patient, wherein the processing circuit is configured to determine the geometric mesh representation from the scan data.

12. The system of claim 11, wherein the scan data comprises a plurality of images of the body from at least two sides of the body, wherein the processing circuit is further configured to determine, from the plurality of images, a geometry file corresponding to the geometric mesh representation, the geometry file including a list of the plurality of vertices and a list of a plurality of faces forming a three dimensional geometric representation of the patient, each face of the list of faces including three vertex indices from the plurality of vertices, and wherein retrieving the geometric mesh representation of the patient comprises retrieving the geometry file.

13. The system of claim 10, wherein determining at least one of the plurality of landmarks comprises:

determining, using a call function from a 3D mesh manipulation library stored in memory, a first horizontal section at a first position of the geometric mesh representation along a first coordinate axis of the spatial coordinates and a second horizontal section of the geometric mesh representation at a second position along the first coordinate axis; and determining a center of volume of a volumetric slice of the mesh between the first horizontal section and the second horizontal section.

14. The system of claim 10, wherein determining the at least one reference geometry comprises:

determining, using a first call function from a 3D mesh manipulation library stored in memory, a set of at least three points on the geometric mesh representation within a threshold range of at least one of the plurality of landmarks;

determining, using a second call function from the 3D mesh manipulation library, a reference plane that fits the set of at least three points, the reference plane approximating a surface fragment of a body area of the 3D mesh; and determining an orientation of the surface fragment comprising determining a normal vector of the reference plane.

15. The system of claim 10, wherein presenting the combined risk score comprises displaying a visually-perceptible indication of a vulnerability level associated with a risk of injury to the patient.

16. A non-transitory computer-readable medium having instructions stored thereon that, upon execution by a computing device, cause the computing device to perform operations comprising:

retrieving patient data comprising a geometric mesh representation of a patient, the geometric mesh representation including a plurality of data points corresponding to spatial coordinates of a plurality of vertices in three dimensions;

determining at least one reference geometry along the geometric mesh representation at a fixed position with respect to the spatial coordinates;

determining a plurality of landmarks corresponding to one of skeletal or soft tissue anatomy for the patient;

determining a plurality of postural deviations of the patient by comparing the at least one reference geometry and the plurality of landmarks, at least one of the plurality of postural deviations being an amount of structural misalignment of at least a portion of the geometric mesh representation;

determining a first body risk score from a first subset of the plurality of postural deviations corresponding to a first body area, and a second body risk score from a second subset of the plurality of postural deviations corresponding to a second body area;

adjusting at least one of the first body risk score or the second body risk score by a weighting factor;

determining a combined risk score from the first body risk score and the second body risk score, comprising normalizing at least one of the first body risk score or the second body risk score by a worst case body risk score corresponding to the first body area or the second body area; and transmitting, to a display of the computing device, the combined risk score.

17. The non-transitory computer-readable medium of claim 16, wherein determining at least one of the plurality of landmarks comprises:

executing a call function from a 3D mesh manipulation library to determine a first horizontal section at a first position of the geometric mesh representation along a first coordinate axis of the spatial coordinates and a second horizontal section of the geometric mesh representation at a second position along the first coordinate axis; and determining a center of volume of a volumetric slice of the mesh between the first horizontal section and the second horizontal section.

18. The non-transitory computer-readable medium of claim 16, wherein determining the at least one reference geometry comprises:

executing a first call function from a 3D mesh manipulation library to determine a set of at least three points on the geometric mesh representation within a threshold range of at least one of the plurality of landmarks;

executing a second call function from the 3D mesh manipulation library to determine a reference plane that approximates the set of at least three points, the reference plane approximating a surface fragment of a body area of the 3D mesh; and determining an orientation of the surface fragment comprising determining a normal vector of the reference plane.

19. The non-transitory computer-readable medium of claim 16, wherein generating the at least one reference geometry comprises generating at least one of a reference line or a surface that corresponds with neutral values of patient posture.

* * * * *